(12) United States Patent
Lantto et al.

(10) Patent No.: US 10,058,610 B2
(45) Date of Patent: Aug. 28, 2018

(54) METHODS FOR TREATING CANCER BY ADMINISTERING HUMANIZED PAN-HER ANTIBODY COMPOSITIONS

(71) Applicant: Symphogen A/S, Ballerup (DK)

(72) Inventors: Johan Lantto, Lund (SE); Kim Vilbour Andersen, Brønshøj (DK); Peter Sejer Andersen, Vanløse (DK); Magnus Strandh, Malmö (SE); Klaus Koefoed, København S (DK); Lars Søgaard Nielsen, Nivå (DK); Mikkel Wandahl Pedersen, Alleroed (DK); Helle Jacobsen, Virum (DK); Michael Kragh, Copenhagen (DK); Ida Kjaer, Copenhagen (DK); Thomas Tuxen Poulsen, Dyssegaard (DK)

(73) Assignee: Symphogen A/S, Ballerup (DK)

( * ) Notice: Subject to any disclaimer, the term of this patent is extended or adjusted under 35 U.S.C. 154(b) by 0 days.

(21) Appl. No.: 15/350,801

(22) Filed: Nov. 14, 2016

(65) Prior Publication Data

US 2017/0165365 A1 Jun. 15, 2017

Related U.S. Application Data

(62) Division of application No. 14/398,441, filed as application No. PCT/IB2013/001027 on May 2, 2013, now Pat. No. 9,527,913.

(60) Provisional application No. 61/809,159, filed on Apr. 5, 2013, provisional application No. 61/641,756, filed on May 2, 2012.

(51) Int. Cl.
| | |
|---|---|
| *A61K 39/395* | (2006.01) |
| *C07K 16/32* | (2006.01) |
| *C07K 16/30* | (2006.01) |
| *A61K 47/48* | (2006.01) |
| *A61K 39/00* | (2006.01) |

(52) U.S. Cl.
CPC ...... *A61K 39/39558* (2013.01); *A61K 47/486* (2013.01); *A61K 47/48384* (2013.01); *A61K 47/48569* (2013.01); *C07K 16/30* (2013.01); *C07K 16/303* (2013.01); *C07K 16/32* (2013.01); *A61K 2039/507* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/76* (2013.01); *C07K 2317/77* (2013.01); *C07K 2317/92* (2013.01)

(58) Field of Classification Search
CPC ........ A61K 39/39558; A61K 47/48384; A61K 47/48569; A61K 47/486; A61K 2039/507; C07K 16/30; C07K 16/303; C07K 16/32; C07K 2317/24; C07K 2317/33; C07K 2317/34; C07K 2317/51; C07K 2317/515; C07K 2317/46; C07K 2317/76; C07K 2317/77; C07K 2317/92

See application file for complete search history.

(56) References Cited

U.S. PATENT DOCUMENTS

| | | |
|---|---|---|
| 7,749,697 B2 | 7/2010 | Oleksiewicz et al. |
| 7,887,805 B2 | 2/2011 | Pedersen et al. |
| 8,414,896 B2 | 4/2013 | Pedersen et al. |
| 8,609,095 B2 | 12/2013 | Pedersen et al. |
| 8,663,640 B2 | 3/2014 | Pedersen et al. |
| 8,691,225 B2 | 4/2014 | Schoeberl et al. |
| 9,155,802 B2 | 10/2015 | Pedersen et al. |
| 9,217,039 B2 | 12/2015 | Pedersen et al. |
| 2007/0178102 A1 | 8/2007 | Yarden et al. |
| 2008/0227660 A1 | 9/2008 | Kastrup et al. |
| 2008/0299581 A1 | 12/2008 | Nielsen et al. |
| 2010/0310558 A1 | 12/2010 | Oleksiewicz et al. |
| 2011/0129588 A1 | 6/2011 | Pedersen et al. |
| 2011/0129855 A1 | 6/2011 | Pedersen et al. |
| 2011/0135636 A1 | 6/2011 | Pedersen et al. |
| 2011/0217305 A1 | 9/2011 | Pedersen et al. |
| 2011/0229463 A1 | 9/2011 | Pedersen et al. |
| 2013/0287684 A1 | 10/2013 | Pedersen et al. |
| 2017/0152322 A1 | 6/2017 | Pedersen et al. |

FOREIGN PATENT DOCUMENTS

| | | |
|---|---|---|
| CN | 100408097 C | 8/2008 |
| CN | 1703243 B | 5/2011 |
| WO | 2000078347 | 12/2000 |
| WO | 2004008099 | 1/2004 |

(Continued)

OTHER PUBLICATIONS

Arpino et al., "Treatment of human epidermal growth factor receptor 2-overexpressing breast cancer xenografts with multiagent HER-targeted therapy," Journal of National Cancer Institute, 99(6):694-705 (2007).

(Continued)

*Primary Examiner* — Robert S Landsman
(74) *Attorney, Agent, or Firm* — Steptoe & Johnson LLP; Z. Ying Li; Wyan-Ching M. Lee

(57) ABSTRACT

The invention relates to humanized recombinant antibodies targeting the EGFR family receptors EGFR, HER2 and HER3, compositions comprising at least one humanized anti-EGFR antibody, at least one humanized anti-HER2 antibody and at least one humanized anti-HER3 antibody, and use of the antibody compositions for treatment of cancer. The invention also relates to the use of antibodies targeting multiple EGFR-family receptors to treat cancer (e.g., pancreatic cancer) and cancer that has acquired resistance to previous therapies.

20 Claims, 46 Drawing Sheets

Specification includes a Sequence Listing.

(56) References Cited

FOREIGN PATENT DOCUMENTS

| WO | 2004/032960 | 4/2004 |
|---|---|---|
| WO | 2004/032961 | 4/2004 |
| WO | 2005099756 | 10/2005 |
| WO | 2007/077028 | 7/2007 |
| WO | 2007076923 | 7/2007 |
| WO | 2008031531 | 3/2008 |
| WO | 2008104183 | 9/2008 |
| WO | 2010/022736 | 3/2010 |
| WO | 2010/108127 | 9/2010 |
| WO | 2011/060206 A2 | 5/2011 |
| WO | 2011/107957 | 9/2011 |
| WO | 2012/059857 | 5/2012 |
| WO | 2012125573 | 9/2013 |

OTHER PUBLICATIONS

Baselga et al., "Novel anticancer targets: revisiting ERBB2 and discovering ERBB3," Nature Reviews-Cancer, 9:463-475 (2009).

Ben-Kasus et al., "Persistent elimination of ErbB-2/HER2-overexpressing tumors using combinations of monoclonal antibodies: Relevance of receptor endocytosis," Proceedings of the National Academy of Sciences, 106(9):3294-3299 (2009).

Bhattacharyy et al., "Nanoconjugation modulates the trafficking and mechanism of antibody induced receptor endocytosis," PNAS 107(33): 14541-14546 (2010).

Friedman et al., "Synergistic down-regulation of receptor tyrosine kinases by combinations of mAbs: implications for cancer immunotherapy," Proceedings of the National Academy of Sciences, 102(6):1915-1920 (2005).

Half et al., "Anti-EGFR and ErbB-2 antibodies attenuate cyclooxygenase-2 expression and cooperatively inhibit survival of human colon cancer cells," Cancer Letters, 251(2):237-246 (2006).

Huhalov et al., "MM-111, an Erb82/Erb83 bispecific antibody with potent activity in Erb82-overexpressing cells, positively combines with trastuzumab to inhibit growth of breast cancer cells driven by the Erb82/Erb83 oncogenic unit," MCR, Annual Meeting, Presentation Abstract, 2 pages, American Association for Cancer Research, United States (2010).

Kawaguchi et al., "Targeting EGFR and HER-2 with cetuximab- and trastuzumab-mediated immunotherapy in oesophageal squamous cell carcinoma," British Journal of Cancer, 97:494-501 (2007).

Maneyval et al., "Pan-HER Biologics (Hermodulins) for the Treatment of Cancer," Drug Development Research, 69:472-479 (2008).

Meira et al., "Combination of cetuximab with chemoradiation, trastuzumab or MAPK inhibitors: mechanisms of sensitisation of cervical cancer cells," British Journal of Cancer, 101:782-791 (2009).

Narayan et al., "Trastuzumab-Induced Her Reprogramming in 'Resistant' Breast Carcinoma Cells," Cancer Research, 69(6):2191-2194 (2009).

Normanno et al., "Cooperative inhibitory effect of ZD1839 (Iressa) in combination with trastuzumab (Herceptin) on human breast cancer cell growth," Annals of Oncology,13:65-72 (2002).

Pedersen et al., "Sym004: A Novel Synergistic Anti-Epidermal Growth Factor Receptor Antibody Mixture with Superior Anticancer Efficacy," Cancer Research, 70(2):588-597 (2010).

Ye et al., "Augmentation of a humanized Anti-HER2 mAb 4D5 induced growth inhibition by a human-mouse chimeric anti-EGF receptor mAb C225," Oncogene, 18:731-738 (1999).

Yoshida et al., "Matuzumab and cetuximab activate the epidermal growth factor receptor but fail to trigger downstream signaling by Akt or Erk," International Journal of Cancer, 122:1530-1538 (2008).

Zhu et al., "Controlled internalization of Her-2/neu receptors by cross-linking for targeted delivery," Cancer Biology & Therapy, 6(12):1960-1966 (2007).

Coyne et al., "Dual potency anti-HER2/neu and anti-EGFR anthracycline immunoconjugates in chemotherapeutic resistant mammary carcinoma combined with cyclosporin A and verapamil P-glycoprotein inhibition," Journal of Drug Targeting 17(6):474-489 (2009).

Huang et al., "A pan-HER approach for cancer therapy: background, current status and future development," Expert Opinion on Biological Therapy 9(1):97-110 (2009).

Khan et al., "Microbead arrays for the analysis of ErbB receptor tyrosine kinase activation and dimerization in breast cancer cells," Assay and Drug Development Technologies, 8(1):27-36 (2010).

Kuwada et al., "Effects of Trastuzumab on Epidermal Growth Factor Receptor-Dependent and -Independent Human Colon Cancer Cells," International Journal of Cancer 109(2):291-301 (2004).

Larbouret et al., "In vivo therapeutic synergism of anti-epidermal growth factor receptor and anti-HER2 monoclonal antibodies against pancreatic carcinomas," Clinical Cancer Research 13(11):3356-3362 (2007).

Larbouret et al., "Combined cetuximab and trastuzumab are superior to gemcitabine in the treatment of human pancreatic carcinoma xenografts," Annals of Oncology 21(1):98-103 (2010).

Larbouret et al., "In pancreatic carcinoma, dual EGFR/HER2 targeting with cetuximab/trastuzumab is more effective than treatment with trastuzumab/erlotinib or lapatinib alone: implication of receptors' down-regulation and dimers' disruption," Neoplasia, 14(2):121-130 (2012).

Patel et al., "Anti-epidermal growth factor receptor monoclonal antibody cetuximab inhibits EGFR/HER-2 heterodimerization and activation," International Journal of Oncology 34(1) (2009).

Schoeberl et al., "An ErbB3 antibody, MM-121, is active in cancers with ligand-dependent activation," Cancer Research 70(6):2845-2494 (2010).

United States Patent and Trademark Office, "Corrected Notice of Allowability," U.S. Appl. No. 14/398,441, filed Nov. 15, 2016.

Figure 1

```
                                    20         CDR1              40
                                     |           |                |
1277_CDRgrafted-H  EVQLVESGGGLVQPGGSLRLSCAASGFAFSYSDMSWVRQAPGKGL  45
        10292     ..............................................R.  45
 10460 & 11294    ..............................................R.  45
                        CDR2    60                      80
                         |       |                       |
1277_CDRgrafted-H  EWVSYMSSAGDVTFYSDTVKGRFTISRDNAKNSLYLQMNSLRAED  90
        10292     .............................................V......  90
 10460 & 11294    .............................................V......  90
                            100
                       CDR3 |
1277_CDRgrafted-H  TAVYYCVRHRDVAMDYWGQGTTVTVSS  117
        10292     ...........................  117
 10460 & 11294    ..............I............  117
```

```
                                    20          CDR1             40
                                     |            |                |
1277_CDRgrafted-L  DIQMTQSPSSLSASVGDRVTITCRSSQSLVHSNGNTYLHWYQQKP  45
        10292     ........................A....................  45
                        CDR2    60                      80
                         |       |                       |
1277_CDRgrafted-L  GKAPKLLIYKVSNRFSGVPSRFSGSGSGTDFTLTISSLQPEDFAT  90
        10292     ..............................................  90
                        CDR3    100
                         |       |
1277_CDRgrafted-L  YYCSQSTHVPTFGGGTKVEIK  111
        10292     .F...................  111
```

```
                                    20          CDR1             40
                                     |            |                |
1277A_CDRgrafted-L  DVVMTQSPLSLPVTLGQPASISCRSSQSLVHSNGNTYLHWFQQRP  45
        10460      .........................................Y....  45
        11294      ........................................L..Y....  45
                         CDR2    60                      80
                          |       |                       |
1277A_CDRgrafted-L  GQSPRRLIYKVSNRFSGVPDRFSGSGSGTDFTLKISRVEAEDVGV  90
        10460      .....L..........................................  90
        11294      .....L..........................................  90
                         CDR3    100
                          |       |
1277A_CDRgrafted-L  YYCSQSTHVPTFGGGTKVEIK  111
        10460      .F..............L....  111
        11294      .F...................  111
```

Figure 2

```
                                 20              CDR1              40
                                  |                |                |
1565_CDRgrafted-H  QVQLVQSGAEVKKPGASVKVSCKASGYTFTSYWMQWVRQAPGQGL 45

10560      . . . . . . . . . . . . . . . L . . . . . . . . . . . . . . 45

11302      . . . . . . . . . . . . . . . L . . . . . . . . . . . . . . 45

CDR2        60                        80
                         |          |                         |
1565_CDRgrafted-H  EWMGNINPSNGDTSFNEEFKSRVTMTRDTSTSTVYMELSSLRSED 90

10560      . . I . . . . . . . . . . . . . . A . . . . . . . . . . . . 90

11302      . . I . . . . . L . . . . . . . . A . . . . . . . . . . . . 90

CDR3   100              120
                              |     |                |
1565_CDRgrafted-H  TAVYYCARDGGLYDGYYFDRWGQGTLVTVSS 121

10560      . . . . . . . . . . . . . . . . . . . . . . . . . . . . . 121

11302      . . . . . . . . . . . . . . . . . . . . . . . . . . . . . 121
```

```
                                 20              CDR1              40
                                  |                |                |
1565_CDRgrafted-L  AIQLTQSPSSLSASVGDRVTITCKASQDVGTAVAWYQQKPGKAPK 45

10560 & 11302  . . . . . . . . . . . . . . . . . . . . . . . . . . . . . . 45

CDR2        60                        80       CDR3
                         |          |                         |         |
1565_CDRgrafted-L  LLIYWASTRHTGVPSRFSGSGSGTDFTLTISSLQPEDFATYYCQQ 90

10560 & 11302  . . . . . . . . . . . . . . . . . . . . . V . . . . . . F . . . 90

CDR3   100
                      |     |
1565_CDRgrafted-L  YSSYPLTFGGGTKVEIK 107

```
                              20              CDR1           40
                               ↓                              ↓
4384_CDRgrafted-H  QVQLVQSGAEVKKPGASVKVSCKASGYTFTSHWMHWVRQAPGQGL  45

10704       ............................................  45

11249       ............................................  45

CDR2          60                 80
                        ↓             ↓                  ↓
4384_CDRgrafted-H  EWMGNINPSNGGTNYNEKFKSRVTMTRDTSTSTVYMELSSLRSED  90

10704       .......S.............L.V.K....A..............  90

11249       .......S.............V.......................  90

CDR3  100
                          ↓     ↓
4384_CDRgrafted-H  TAVYYCARATYDFSWFYYWGQGTLVTVSS  119

10704       .............................  119

11249       .............................  119
```

```
                              20              CDR1           40
                               ↓                              ↓
4384_CDRgrafted-L  DIQMTQSPSSLSASVGDRVTITCRSSQDISNYLNWYQQKPGKAPK  45

10704       ...........................................V.  45

11249       ..............................................  45

CDR2              60              80       CDR3
                       ↓                 ↓               ↓         ↓
4384_CDRgrafted-L  LLIYSRLHSGVPSRFSGSGSGTDFTFTISSLQPEDIATYYCQQX  90

10704       ..M.......................Y.................  90

11249       ..M.......................Y.................  90

CDR3  100
                    ↓     ↓
4384_CDRgrafted-L  NTLPLTFGGGTKVEIK  106

```
                                   20              CDR1              40
                                    |                                 |
4517_CDRgrafted-H  EVQLVESGGGLVKPGGSLRLSCAASGFTFSSYGMSWVRQAPGKGL  45

1114S   ............................................  45
                           CDR2          60                   80
                                          |                    |
4517_CDRgrafted-H  EWVSTISGGGSYIYYPDSVKGRFTISRDNAKNSLYLQMNSLRAED  90

1114S   ...A......................I...S.............  90
                           100                         120
                         CDR3                           |
4517_CDRgrafted-H  TAVYYCARKGNYGNYGKLAYWGQGTTVTVSS  121

1114S   ...............................  121
```

```
                                   20              CDR1              40
                                    |                                 |
4517_CDRgrafted-L  DIQMTQSPSSLSASVGDRVTITCRASENIYSNLAWYQQKPGKAPK  45

1114S   ............................................  45
                           CDR2         60                    80
                                          |                    |      CDR3
4517_CDRgrafted-L  LLIYAATNLADGVPSRFSGSGSGTDFTLTISSLQPEDFATYYCQH  90

1114S   ......T..................Y..............S...  90
                     CDR3       100
                                 |
4517_CDRgrafted-L  FWGTPWTFGQGTKVEIK  107

```
                                    20              CDR1              40
                                     |               |                 |
5038_CDRgrafted-H  QVQLQESGPGLVKPSQTLSLTCTVSGYSITSGFYWTWIRQHPGKG  45

10738  ............................................. 45

10810  ...........................................N. 45

CDR2            60                80
                          |               |                 |
5038_CDRgrafted-H  LEWIGFISYDGSNNYNPSLKNRVTISVDTSKNQFSLKLSSVTAAD  90

10738  ...M.....S..............I................... 90

10810  .........S.................................. 90

CDR3 100                    120
                               |                           |
5038_CDRgrafted-H  TAVYYCARGGGYYGNLFDYWGQGTLVTVSS 120

10738  .............................. 120

10810  ..T........................... 120
```

```
                                    20              CDR1              40
                                     |               |                 |
5038_CDRgrafted-L  DIQMTQSPSSLSASVGDRVTITCRPSQDISNYVNWYQQKPGKAPK 45

10738  ...........................F............V.  45

10810  ...........................F..............  45

CDR2           60                 80              CDR3
                          |              |                  |                |
5038_CDRgrafted-L  LLIYHTSRLHSGVPSRFSGSGSGTDFTFTISSLQPEDIATYYCQQ 90

10738  ...F................................I....... 90

10810  ...F...........................L............ 90

CDR3    100
                    |       |
5038_CDRgrafted-L  GITLPWTFGQGTKVEIK 107

```
                                      20           CDR1              40
                                       |            |                 |
5082_CDRgrafted-H  QVQLQESGPGLVKPSQTLSLTCTVSGYSITSAYYWNWIRQHPGKG  45

11006    ...........................................  45

11052    ......................................F....  45

CDR2        60                    80
                        |           |                     |
5082_CDRgrafted-H  LEWIGYIGYDGRNTYNPSLKNRVTISVDTSKNQFSLKLSSVTAAD  90

11006    V..M....S...................R...............  90

11052    V..M....S...................R...............  90

CDR3  100
                               |     |
5082_CDRgrafted-H  TAVYYCSREGDYGYSDYWGQGTLVTVSS  118

11006    ............................  118

11052    ............................  118
```

```
                                      20           CDR1              40
                                       |            |                 |
5082_CDRgrafted-L  DIQMTQSPSSLSASVGDRVTITCRASQDINNYLNWYQQKPGKAPK  45

11006    .....................V.......T.............V.  45

11052    .....................V.......................V.  45

CDR2          60                   80      CDR3
                        |             |                    |        |
5082_CDRgrafted-L  LLIYYTSRLQSGVPSRFSGSGSGTDFTLTISSLQPEDFATYYCQQ  90

11006    ...........................................F...  90

11052    ...................................Y.......F...  90

CDR3      100
                    |         |
5082_CDRgrafted-L  SETLPWTFGQGTKVEIK  107

11006    .................  107

11052    .........L.......  107
```

Figure 7
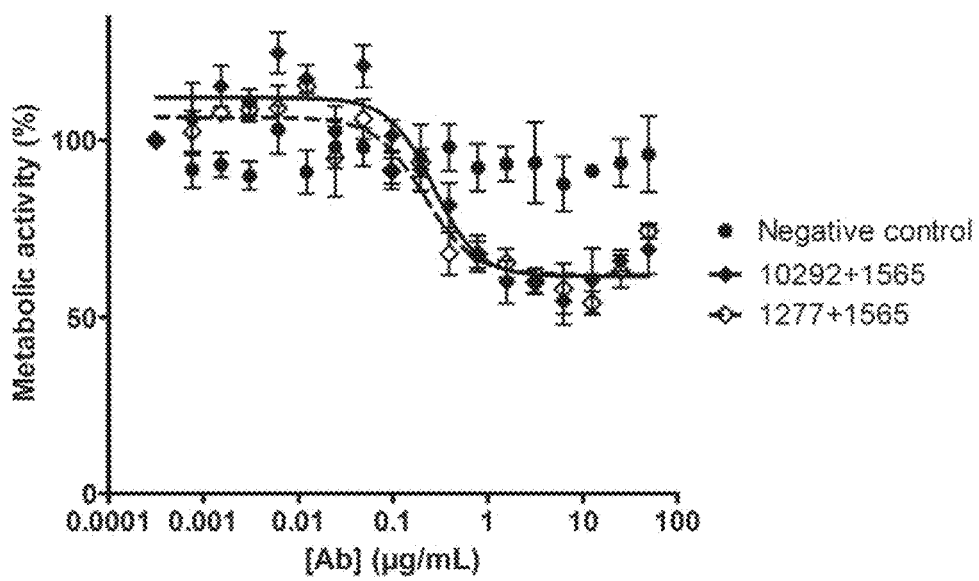
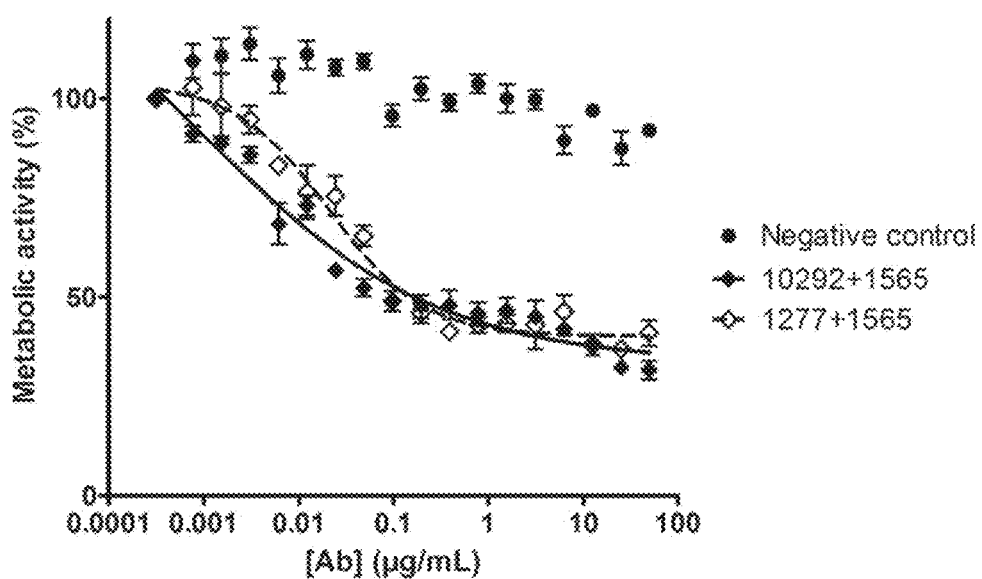

Figure 8
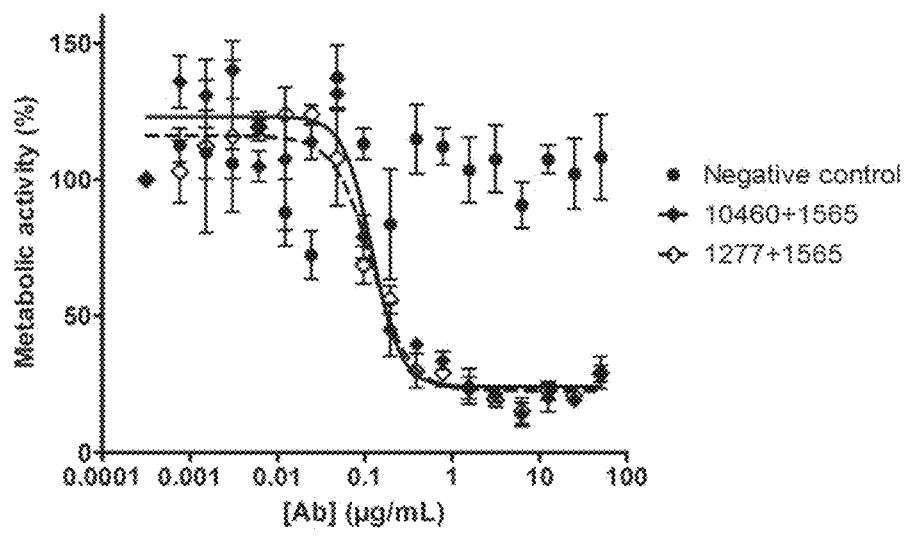
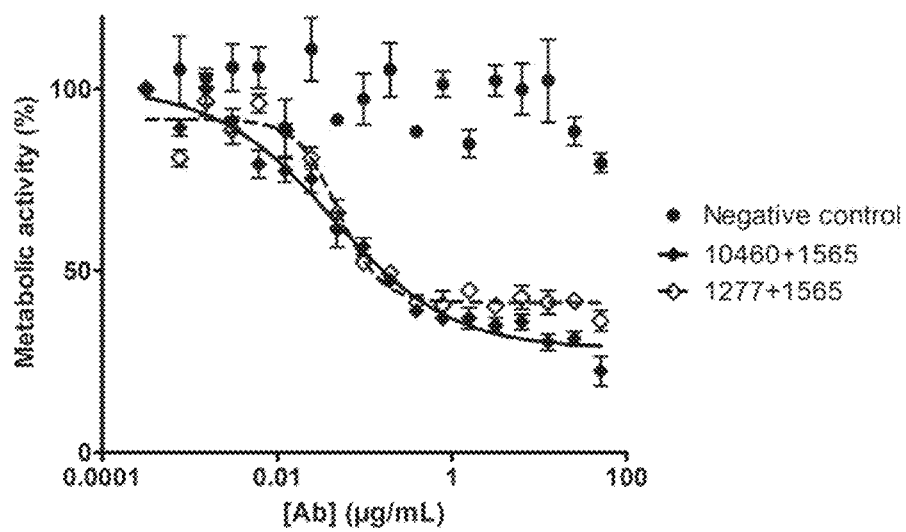

Figure 9
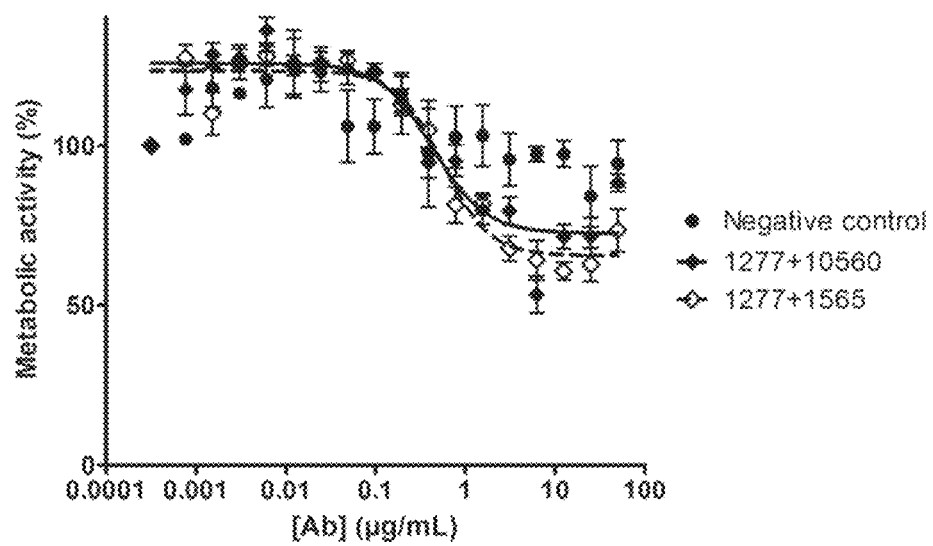
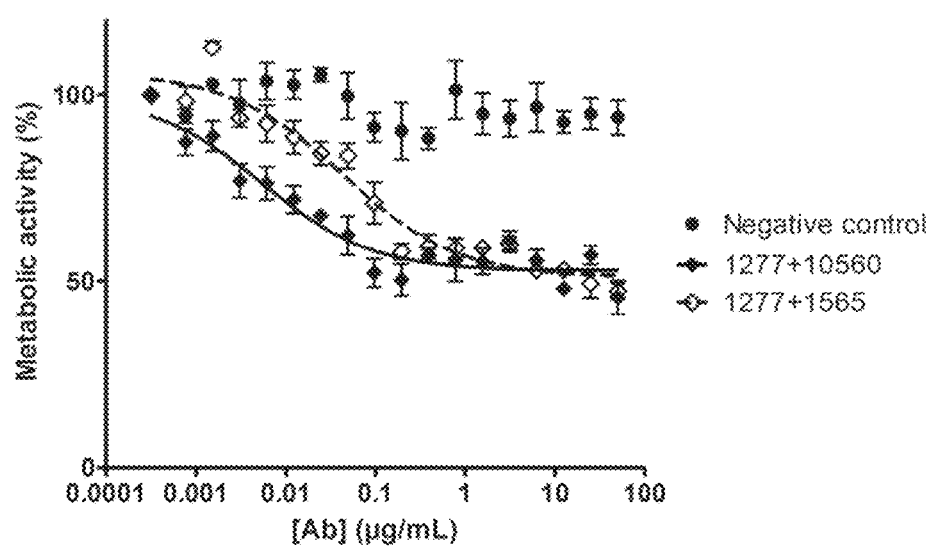

Figure 10
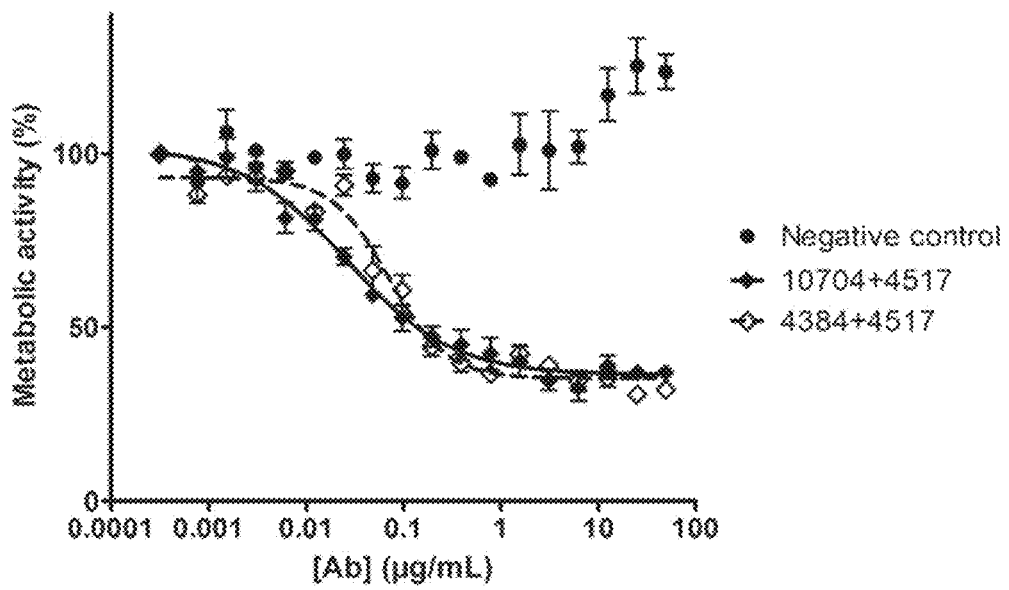
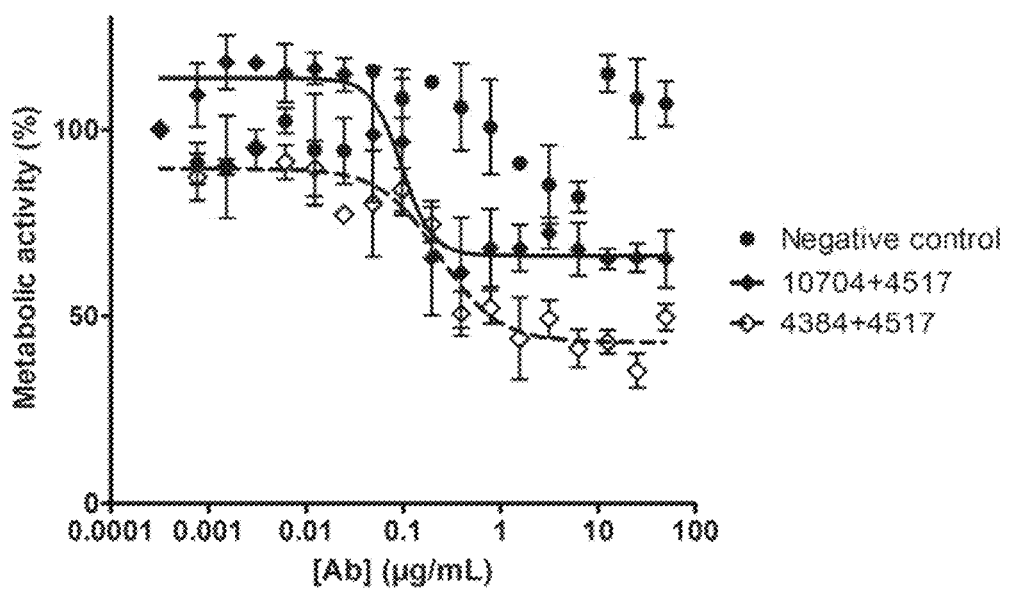

Figure 11
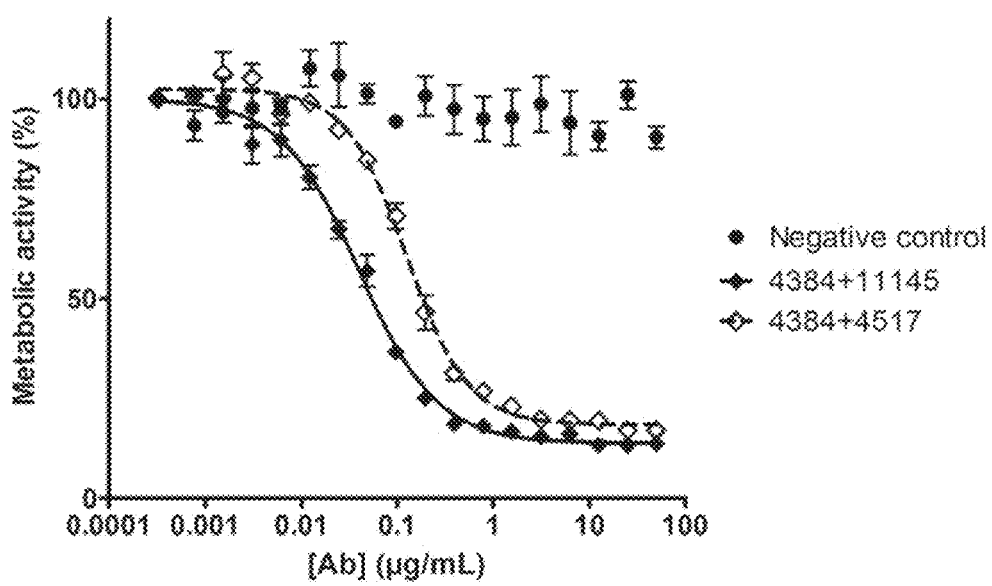
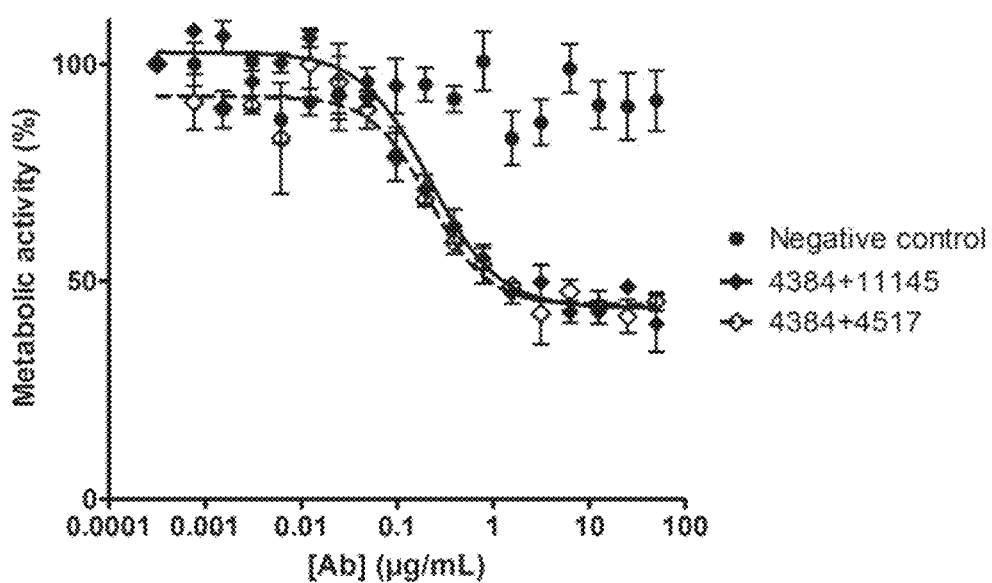

Figure 12
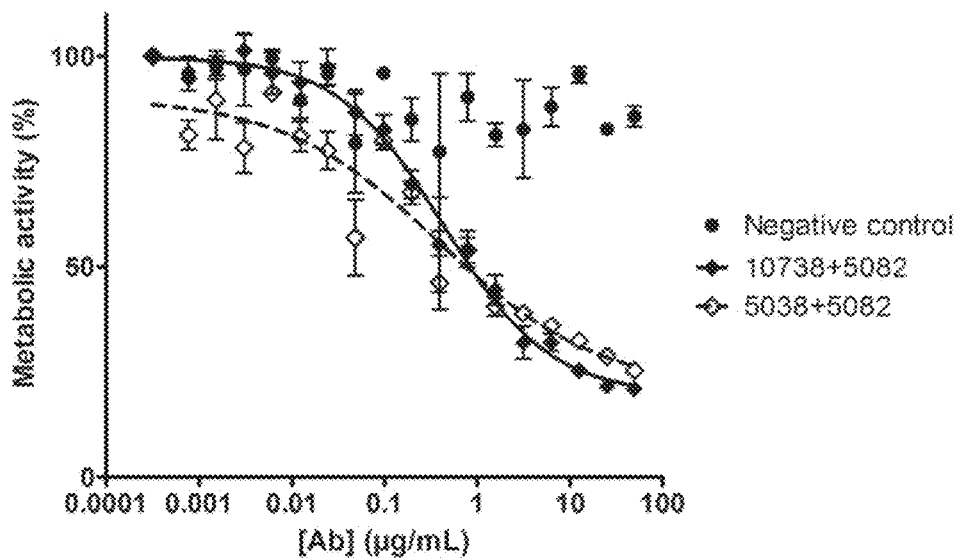
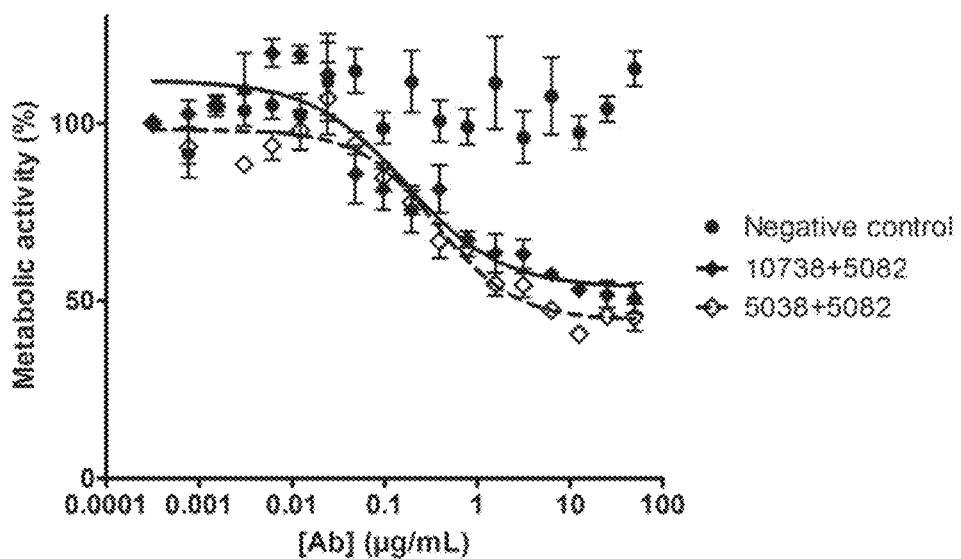

Figure 13
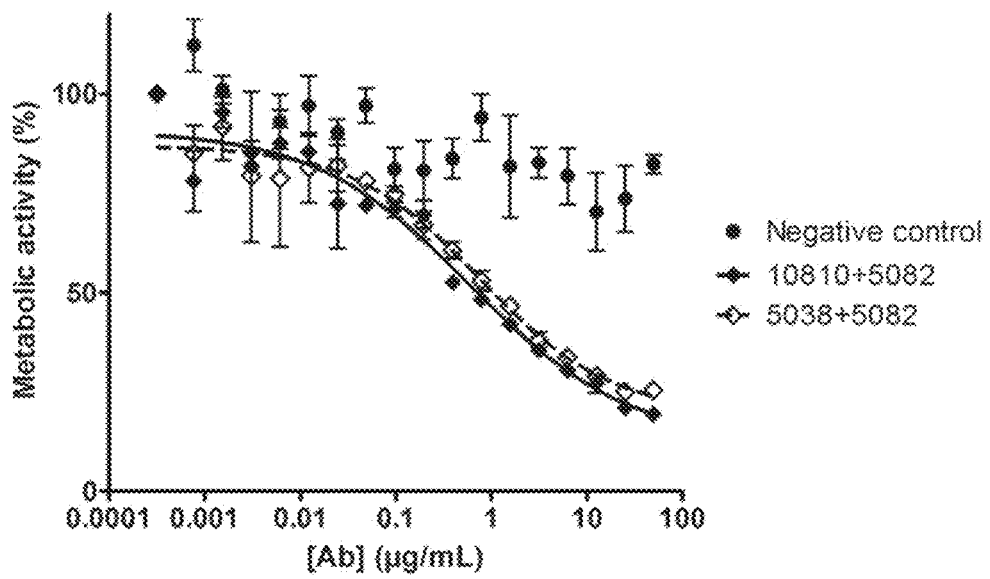
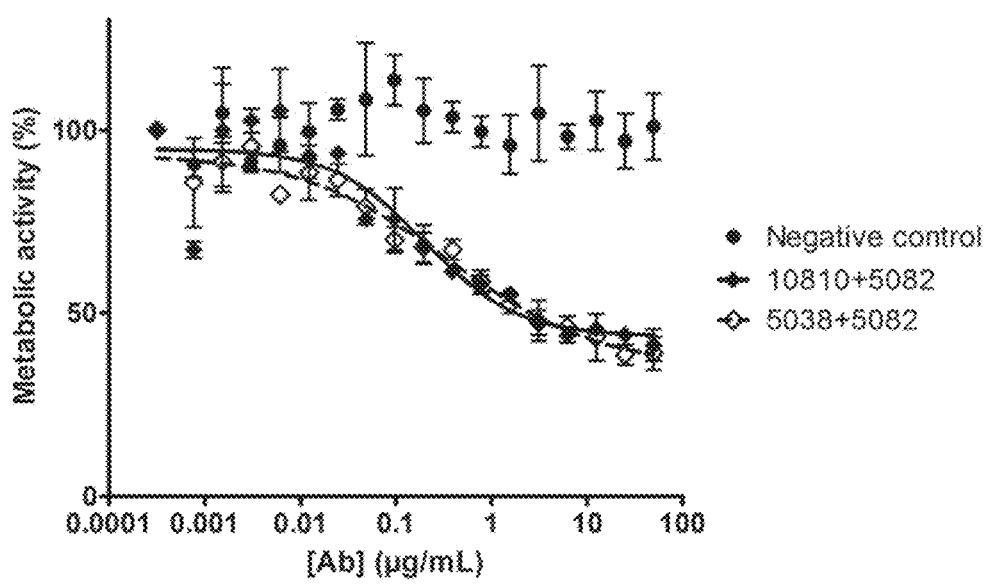

Figure 14
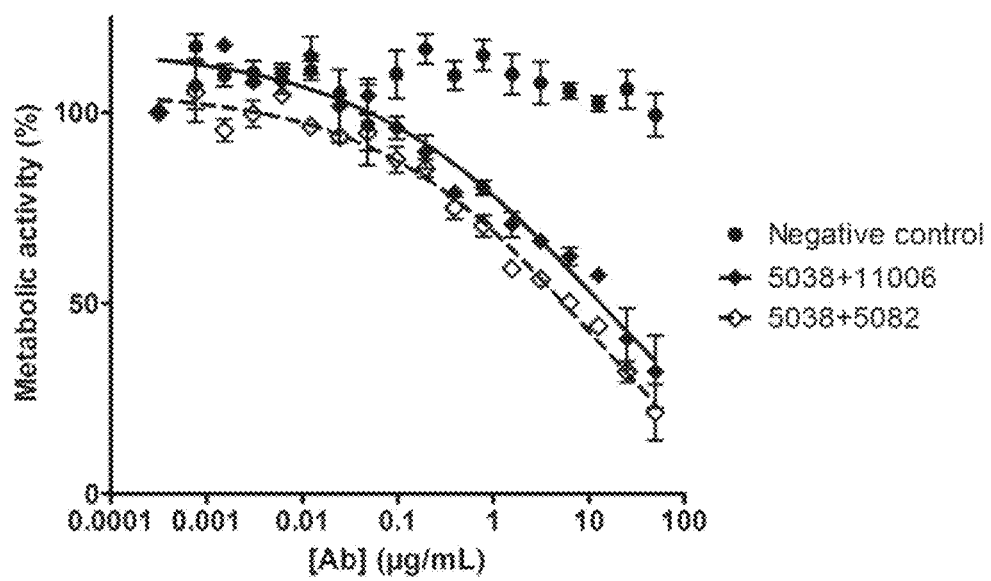
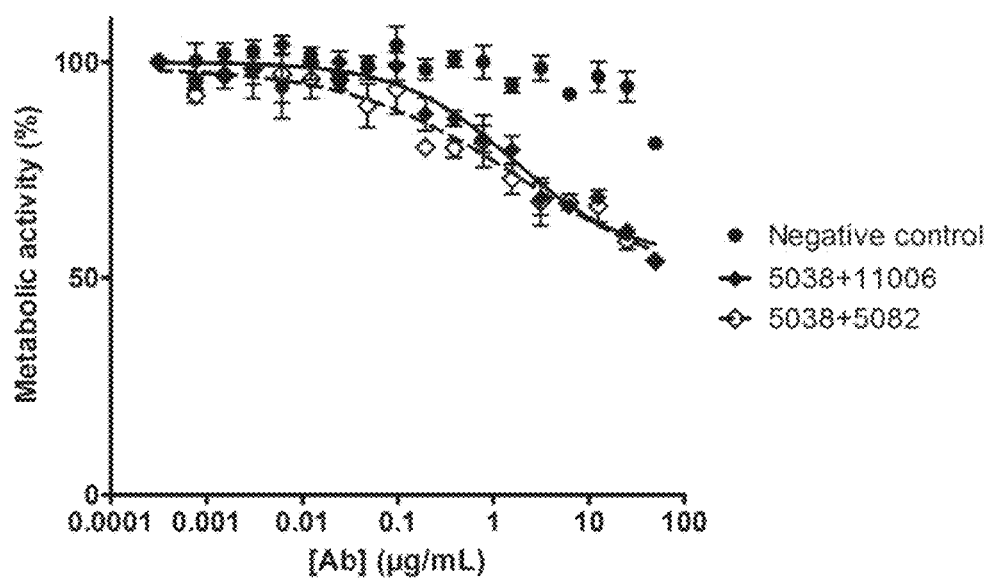

Figure 15
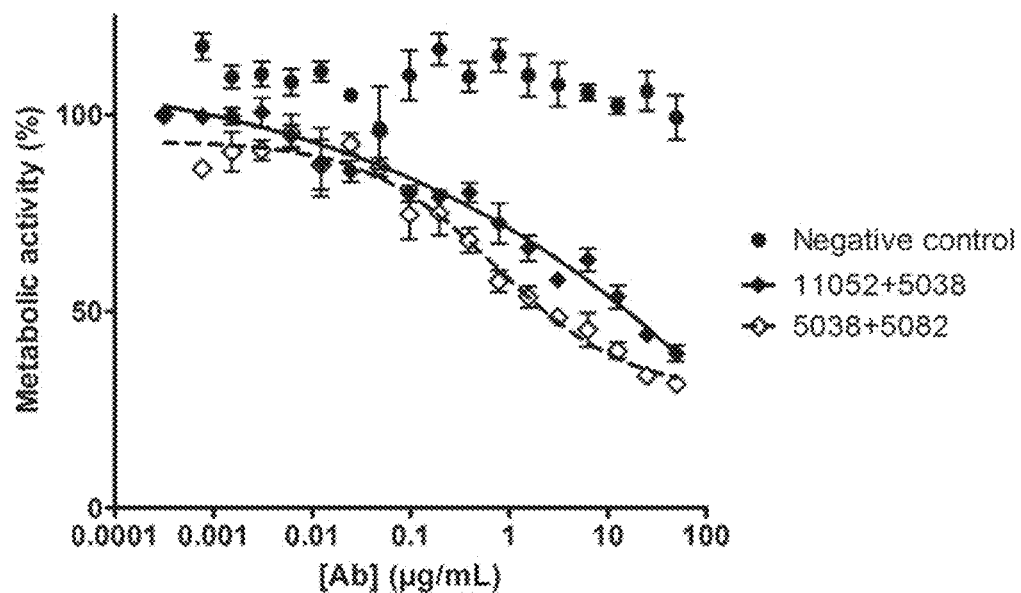
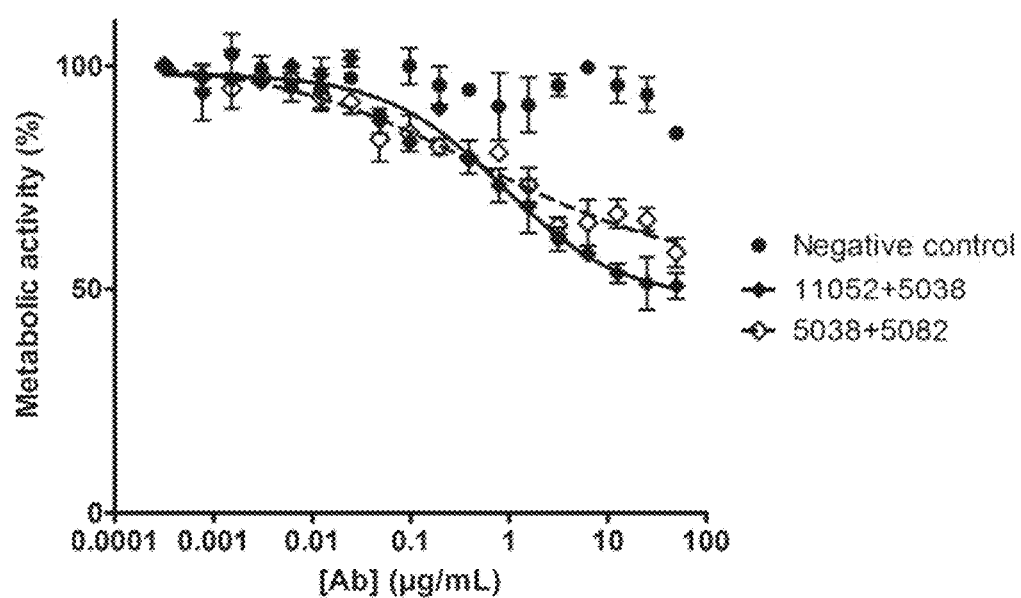

Figure 16

| Ab ID | Source library (specificity) | ELISA reactivity ||||||||||||
|---|---|---|---|---|---|---|---|---|---|---|---|---|
| | | hu EGFR | cy EGFR | mu EGFR | hu HER2 | cy HER2 | mu HER2 | hu HER3 | cy HER3 | mu HER3 | hu HER4 | mu HER4 |
| 1277 | chimeric (EGFR) | +++ | +++ | - | - | - | - | - | - | - | - | - |
| 10292 | 1277 (EGFR) | +++ | +++ | - | - | - | - | - | - | - | - | - |
| 10460 | 1277A (EGFR) | +++ | +++ | - | - | - | - | - | - | - | - | - |
| 11294 | 1277A (EGFR) | +++ | +++ | - | - | - | - | - | - | - | - | - |
| 1565 | chimeric (EGFR) | +++ | +++ | - | - | - | - | - | - | - | - | - |
| 10560 | 1565 (EGFR) | +++ | +++ | - | - | - | - | - | - | - | - | - |
| 11302 | 1565 (EGFR) | +++ | +++ | - | - | - | - | - | - | - | - | - |
| 4384 | chimeric (HER2) | - | - | - | +++ | +++ | - | - | - | - | - | - |
| 10704 | 4384 (HER2) | - | - | - | +++ | +++ | - | - | - | - | - | - |
| 4517 | chimeric (HER2) | - | - | - | +++ | +++ | - | - | - | - | - | - |
| 11145 | 4517 (HER2) | - | - | - | +++ | - | - | - | - | - | - | - |
| 5038 | chimeric (HER3) | - | - | - | - | - | - | +++ | +++ | - | - | - |
| 10738 | 5038 (HER3) | - | - | - | - | - | - | +++ | +++ | - | - | - |
| 10810 | 5038 (HER3) | - | - | - | - | - | - | +++ | +++ | - | - | - |
| 5082 | chimeric (HER3) | - | - | - | - | - | - | +++ | +++ | - | - | - |
| 11006 | 5082 (HER3) | - | - | - | - | - | - | +++ | +++ | - | - | - |
| 11052 | 5082 (HER3) | - | - | - | - | - | - | - | - | - | - | - |
| Neg | Isotype control | - | - | - | - | - | - | - | - | - | - | - |

Figure 17
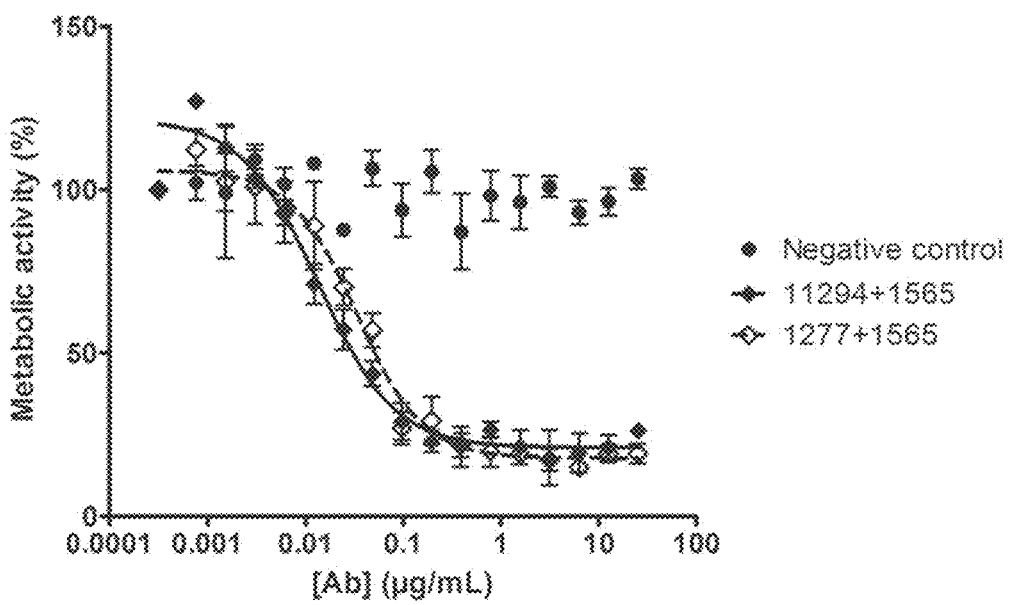
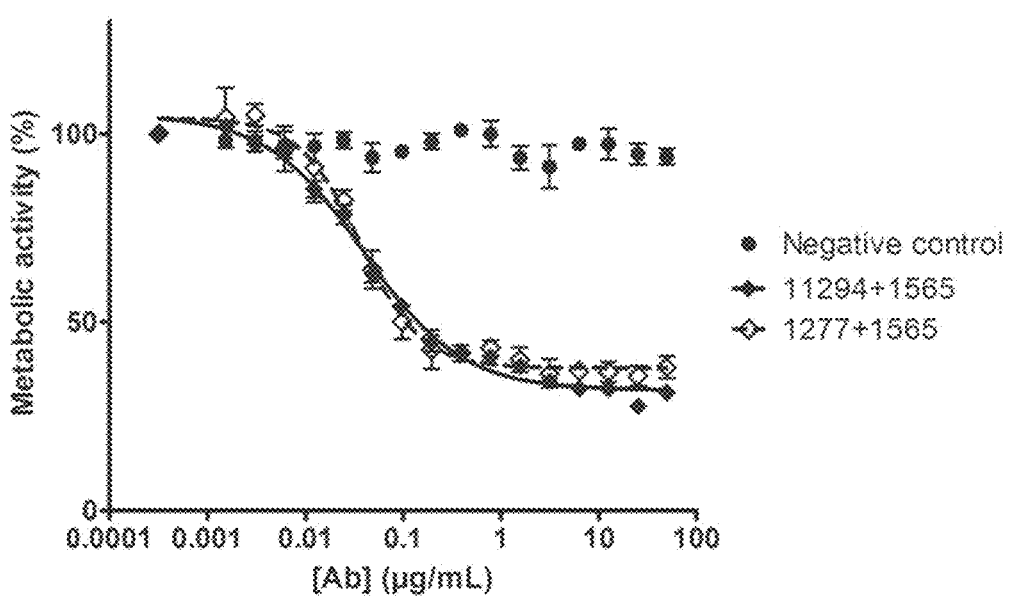

Figure 18
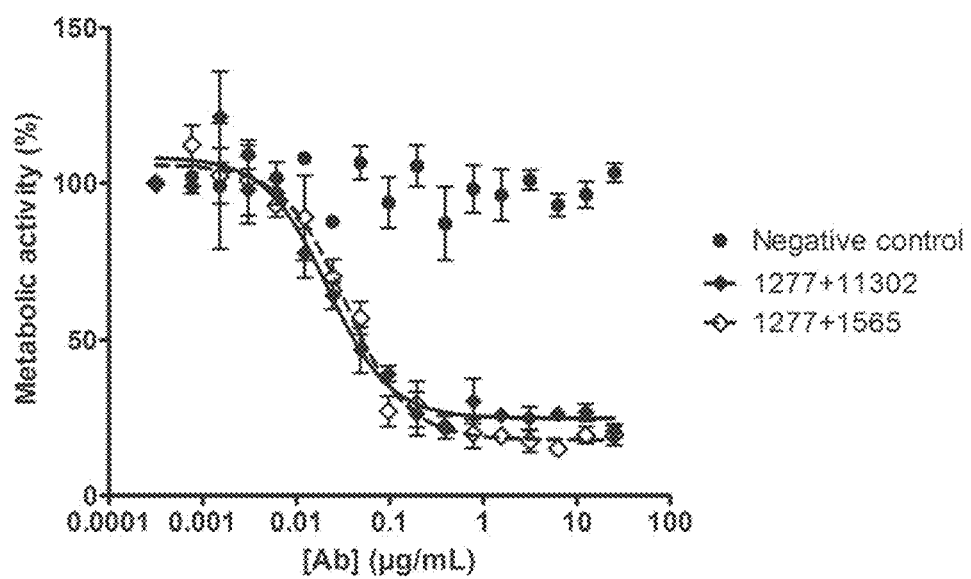
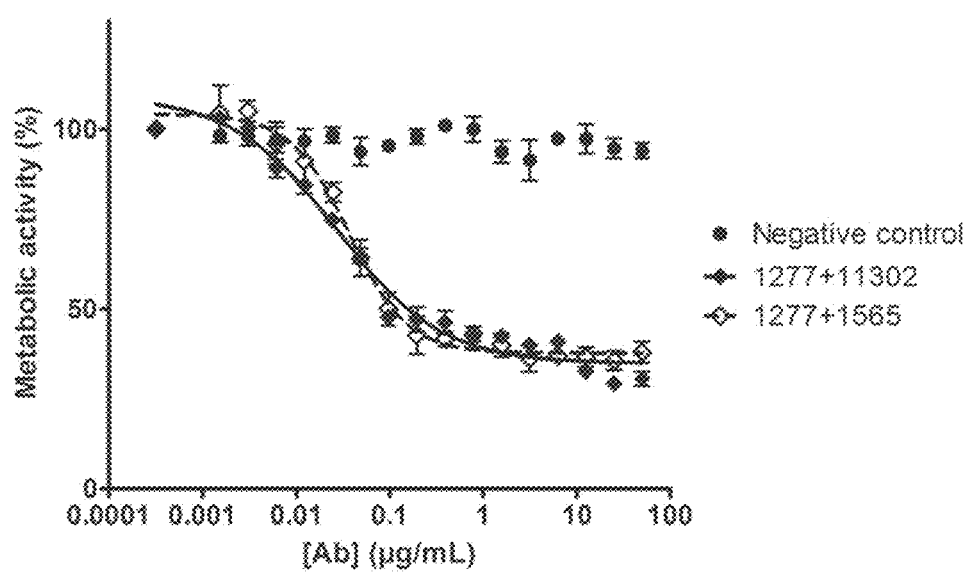

Figure 19
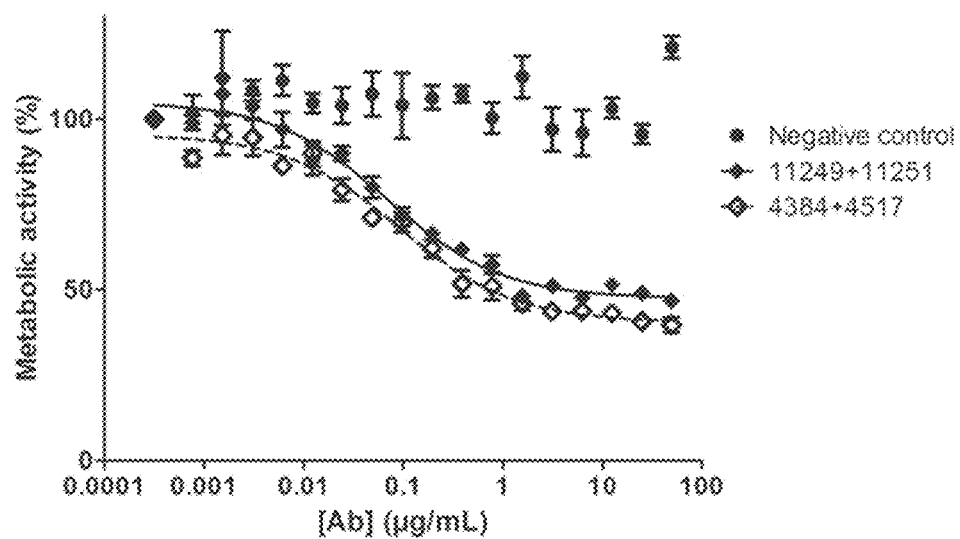
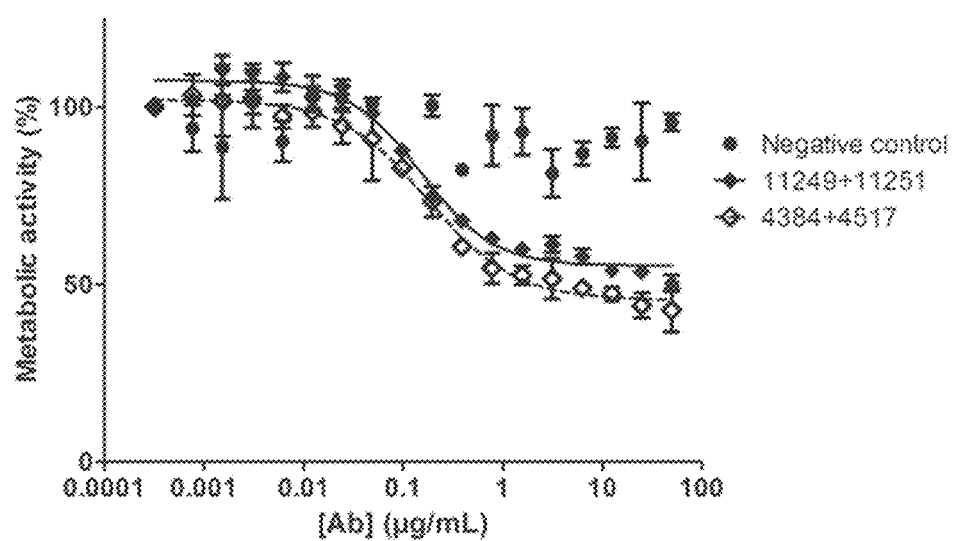

Figure 23

| | Origin | Subtype | Cell line | Pan-HER | EGFR+HER2 | EGFR+HER3 | HER2+HER3 | EGFR | HER2 | HER3 | Cetuximab | Trastuzumab | MM-121 | Negative control |
|---|---|---|---|---|---|---|---|---|---|---|---|---|---|---|
| 1 | Breast | Ductal Carcinoma | MDA-MB175-VII | 10 | 50 | 25 | 25 | 90 | 65 | 35 | 90 | 85 | 30 | 100 |
| 2 | Head and Neck | HNSCC | HN5 | 10 | 10 | 10 | 100 | 12 | 100 | 100 | 10 | 100 | 95 | 105 |
| 3 | Lung | Adenocarcinoma | HCC827 | 11 | 17 | 14 | 87 | 22 | 100 | 100 | 9 | 100 | 95 | 94 |
| 4 | Gastric | Carcinoma | N87 (NCI-N87) | 14 | 14 | 78 | 21 | 88 | 21 | 81 | 83 | 41 | 88 | 100 |
| 5 | Skin | Epidermoid carcinoma | A431NS | 15 | 29 | 23 | 66 | 49 | 87 | 100 | 98 | 100 | 74 | 100 |
| 6 | Head and Neck | Pharyngeal Squamous cell carcinoma | FaDu | 16 | 16 | 15 | 83 | 28 | 90 | 80 | 30 | 93 | 79 | 104 |
| 7 | Gastric | Adenocarcinoma | OE19 | 20 | 20 | 60 | 20 | 85 | 25 | 100 | 100 | 45 | 85 | 100 |
| 8 | Breast | Ductal Carcinoma | MDA-MB175-VII | 20 | 75 | 35 | 45 | 90 | 75 | 55 | 90 | 70 | 50 | 105 |
| 9 | Skin | Epidermoid carcinoma | A431-NS | 20 | 30 | 25 | 80 | 75 | 100 | 80 | 90 | 90 | 65 | 110 |
| 10 | Colon | Rectal adenocarcinoma | SW948 | 25 | 26 | 25 | 54 | 21 | 49 | 53 | 23 | 44 | 56 | 71 |
| 11 | Ovary | Adenocarcinoma | RMG-I | 25 | 20 | 15 | 30 | 25 | 75 | 95 | 20 | 30 | 70 | 75 |
| 12 | Breast | Carcinoma | BT474 | 25 | 25 | 80 | 30 | 110 | 30 | 75 | 100 | 30 | 85 | 120 |
| 13 | Oesophagus | Squamous cell carcinoma | TE11 | 28 | 25 | 26 | 76 | 62 | 74 | 85 | 71 | 100 | 81 | 100 |
| 14 | Colon | | GEO | 28 | 29 | 25 | 72 | 20 | 81 | 105 | 27 | 67 | 97 | 90 |
| 15 | Lung | Adenocarcinoma | H358 (NCI-H358) | 31 | 42 | 33 | 64 | 51 | 87 | 90 | 55 | 75 | 84 | 94 |
| 16 | Lung | Adenocarcinoma | CALU-3 | 35 | 35 | 45 | 100 | 55 | 80 | 100 | 55 | 67 | 90 | 100 |
| 17 | Gastric | Adenocarcinoma | OE19 | 35 | 40 | 85 | 40 | 85 | 40 | 100 | 85 | 55 | 90 | 90 |
| 18 | Lung | Mucoepidermoid Carcinoma | H292 (NCI-H292) | 35 | 37 | 38 | 95 | 38 | 95 | 95 | 39 | 91 | 90 | 98 |
| 19 | Breast | Ductal Carcinoma | HCC202 | 39 | 46 | 82 | 57 | 96 | 66 | 88 | 83 | 63 | 90 | 90 |
| 20 | Colon | Adenocarcinoma | LS-174T | 43 | 24 | 24 | 72 | 21 | 88 | 77 | 28 | 63 | 79 | 67 |
| 21 | Breast | Ductal Carcinoma | ZR-75-30 | 44 | 55 | 80 | 70 | 85 | 50 | 75 | 85 | 40 | 70 | 95 |
| 22 | Lung | Adenocarcinoma | H1975 (NCI-H1975) | 46 | 44 | 50 | 100 | 70 | 100 | 84 | 79 | 94 | 83 | 100 |
| 23 | Oesophagus | Squamous cell carcinoma | KYSE520 | 48 | 51 | 47 | 71 | 62 | 100 | 100 | 59 | 100 | 100 | 100 |
| 24 | Breast | Adenocarcinoma | AU565 | 52 | 66 | 60 | 61 | 83 | 79 | 100 | 100 | 50 | 80 | 100 |
| 25 | Ovary | Adenocarcinoma | IGR-OV1 | 55 | 30 | 40 | 80 | 45 | 80 | 90 | 45 | 55 | 110 | 80 |
| 26 | Breast | Adenocarcinoma | AU-565 | 55 | 55 | 75 | 55 | 80 | 35 | 88 | 100 | 75 | 95 | 100 |
| 27 | Pancreas | Adenocarcinoma | CAPAN-1 | 55 | 50 | 55 | 100 | 85 | 90 | 95 | 65 | 80 | 85 | 100 |
| 28 | Oesophagus | Adenocarcinoma (lower third) | OE33 | 56 | 90 | 91 | 97 | 70 | 100 | 95 | 81 | 100 | 100 | 100 |
| 29 | Pancreas | Carcinoma | PK-1 | 56 | 75 | 57 | 83 | 88 | 93 | 79 | 83 | 83 | 80 | 99 |
| 30 | Pancreas | Adenocarcinoma, ductal | CFPAC-1 | 60 | 60 | 55 | 95 | 75 | 95 | 90 | 75 | 95 | 90 | 100 |
| 31 | Pancreas | Carcinoma | BxPC3 | 65 | 72 | 55 | 44 | 100 | 75 | 66 | 100 | 94 | 63 | 100 |
| 32 | Colon | Rectal adenocarcinoma | SW1463 | 65 | 45 | 90 | 110 | 65 | 100 | 100 | 65 | 115 | 115 | 120 |
| 33 | Skin | Epidermoid carcinoma | A-431 | 65 | 55 | 55 | 90 | 85 | 100 | 85 | 90 | 100 | 85 | 100 |
| 34 | Colon | Carcinoma | COLO678 | 65 | 81 | 54 | 100 | 53 | 96 | 36 | 82 | 94 | 93 | 100 |
| 35 | Lung | Adenocarcinoma | H820 (NCI-H820) | 65 | 63 | 60 | 77 | 89 | 76 | 86 | 100 | 90 | 82 | 100 |
| 36 | Oesophagus | Squamous cell carcinoma | COLO680N | 66 | 59 | 65 | 86 | 70 | 99 | 100 | 73 | 94 | 100 | 100 |
| 37 | Pancreas | Adenocarcinoma | AsPC1 | 67 | 49 | 55 | 93 | 65 | 100 | 75 | 72 | 100 | 78 | 100 |
| 38 | Breast | Carcinoma | HCC1937 | 68 | 61 | 63 | 88 | 84 | 89 | 86 | 78 | 88 | 87 | 94 |
| 39 | Colon | Colorectal adenocarcinoma | SW403 | 70 | 50 | 55 | 100 | 80 | 86 | 95 | 65 | 80 | 80 | 115 |
| 40 | Ovary | Adenocarcinoma | OVCAR-3 | 70 | 75 | 85 | 90 | 80 | 90 | 90 | 75 | 90 | 85 | 100 |
| 41 | Ovary | Adenocarcinoma | OVCAR-5 | 70 | 60 | 70 | 95 | 70 | 95 | 85 | 75 | 80 | 95 | 100 |
| 42 | Lung | Large cell carcinoma | H661 (NCI-H661) | 70 | 60 | 100 | 80 | 105 | 85 | 80 | 100 | 85 | 85 | 110 |
| 43 | Breast | Adenocarcinoma | SK-BR-3 | 70 | 77 | 70 | 80 | 100 | 80 | 80 | 90 | 73 | 80 | 105 |
| 44 | Endometrium | Adenocarcinoma | MFE-296 | 70 | 70 | 65 | 70 | 105 | 70 | 70 | 100 | 70 | 65 | 100 |
| 45 | Ovary | Adenocarcinoma | OVCAR-8 | 71 | 84 | 69 | 103 | 100 | 100 | 75 | 77 | 86 | 75 | 97 |
| 46 | Endometrium | Carcinoma | RL95-2 | 72 | 64 | 72 | 72 | 92 | 92 | 89 | 76 | 100 | 91 | 97 |
| 47 | Colon | Rectal adenocarcinoma | SW837 | 75 | 85 | 80 | 115 | 75 | 100 | 105 | 80 | 95 | 105 | 115 |
| 48 | Colon | Colorectal carcinoma | T84 | 75 | 70 | 55 | 90 | 65 | 100 | 100 | 85 | 100 | 100 | 100 |
| 49 | Ovary | Cystadenocarcinoma | RMUG-S | 75 | 75 | 65 | 100 | 75 | 100 | 100 | 85 | 90 | 100 | 120 |
| 50 | Lung | Adenocarcinoma | A549 | 75 | 70 | 63 | 68 | 81 | 73 | 85 | 78 | 99 | 52 | 100 |
| 51 | Pancreas | Carcinoma | CAPAN-2 | 76 | 73 | 75 | 99 | 84 | 100 | 100 | 76 | 94 | 100 | 99 |
| 52 | Colon | Adenocarcinoma | GP5d | 80 | 100 | 66 | 105 | 70 | 97 | 100 | 61 | 86 | 110 | 109 |
| 53 | Colon | Adenocarcinoma | CaCO2 | 80 | 70 | 70 | 100 | 75 | 95 | 95 | 75 | 90 | 85 | 95 |
| 54 | Breast | Carcinoma | BT20 | 81 | 69 | 64 | 97 | 72 | 100 | 100 | 60 | 101 | 95 | 99 |
| 55 | Breast | Adenocarcinoma | MDA-MB-468 | 81 | 80 | 77 | 86 | 85 | 103 | 113 | 80 | 96 | 95 | 94 |
| 56 | Prostate | Carcinoma | DU145 | 82 | 83 | 75 | 102 | 82 | 103 | 105 | 92 | 100 | 99 | 110 |
| 57 | Lung | Squamous cell carcinoma, Mesothelioma | H226 (NCI-H226) | 85 | 100 | 95 | 100 | 95 | 100 | 100 | 95 | 100 | 95 | 100 |
| 58 | Pancreas | Adenocarcinoma | Panc08.13 | 85 | 90 | 100 | 110 | 85 | 110 | 110 | 85 | 100 | 95 | 100 |
| 59 | Urinary tract | Carcinoma | RT-112 | 85 | 85 | 85 | 100 | 85 | 90 | 100 | 80 | 85 | 100 | 100 |
| 60 | Lung | Adenocarcinoma | A549 | 85 | 100 | 95 | 100 | 115 | 105 | 105 | 80 | 85 | 90 | 105 |
| 61 | Lung | Squamous cell carcinoma | EBC1 | 85 | 100 | 95 | 105 | 100 | 100 | 95 | 76 | 75 | 75 | 95 |
| 62 | Bone | Osteosarcoma | U2-OS | 85 | 80 | 90 | 90 | 95 | 95 | 95 | 85 | 85 | 105 | 95 |
| 63 | Endometrium | Endometrial Adenocarcinoma | HEC-108 | 85 | 100 | 100 | 105 | 100 | 100 | 105 | 85 | 90 | 95 | 110 |
| 64 | Breast | Adenocarcinoma | CAL-120 | 85 | 95 | 95 | 100 | 90 | 90 | 90 | 90 | 90 | 100 | 100 |
| 65 | Colon | Adenocarcinoma | LoVo | 85 | 80 | 80 | 100 | 90 | 100 | 90 | 80 | 95 | 90 | 100 |
| 66 | Lung | Adenocarcinoma | H1993 (NCI-H1993) | 85 | 100 | 105 | 110 | 105 | 95 | 95 | 90 | 95 | 90 | 95 |
| 67 | Colon | Colorectal adenocarcinoma | DLD-1 | 87 | 98 | 94 | 100 | 100 | 96 | 100 | 95 | 97 | 100 | 96 |
| 68 | Ovary | Adenocarcinoma | SKOV3 | 87 | 87 | 83 | 83 | 100 | 100 | 100 | 100 | 95 | 113 | 115 |
| 69 | Urinary tract | Carcinoma | RT-4 | 90 | 75 | 80 | 85 | 90 | 95 | 90 | 70 | 85 | 95 | 100 |
| 70 | Gastric | Adenocarcinoma | MKN-45 | 90 | 100 | 90 | 85 | 90 | 100 | 90 | 90 | 95 | 95 | 90 |
| 71 | Pancreas | Ductal carcinoma | PANC-1 | 90 | 90 | 85 | 95 | 90 | 85 | 85 | 90 | 95 | 100 | 100 |
| 72 | Gastric | Carcinoma | SNU-16 | 90 | 100 | 90 | 90 | 90 | 90 | 90 | 90 | 75 | 95 | 100 |
| 73 | Gastric | Gastric carcinoma | KATOIII | 90 | 100 | 85 | 90 | 100 | 100 | 85 | 105 | 110 | 80 | 110 |
| 74 | Breast | Ductal carcinoma | MDA-MB-134-VI | 90 | 75 | 90 | 100 | 99 | 90 | 87 | 90 | 91 | 99 | 102 |
| 75 | Lung | Large cell carcinoma | H460 (NCI-H460) | 90 | 90 | 80 | 75 | 90 | 90 | 85 | 90 | 95 | 105 | 85 |
| 76 | Breast | Adenocarcinoma | MCF7 | 95 | 90 | 90 | 100 | 104 | 90 | 95 | 90 | 95 | 100 | 95 |
| 77 | Skin | Melanoma | A2058 | 95 | 90 | 100 | 100 | 100 | 95 | 90 | 95 | 90 | 50 | 90 |
| 78 | Colon | Adenocarcinoma | SW480 | 95 | 105 | 113 | 99 | 105 | 100 | 99 | 105 | 121 | 115 | 100 |
| 79 | Colon | Colorectal carcinoma | LS1034 | 96 | 83 | 94 | 85 | 94 | 96 | 83 | 96 | 100 | 93 | 87 |

Figure 24

| # | Origin | Subtype | Cell line | Pan-HER | EGFR+HER2 | EGFR+HER3 | HER2+HER3 | EGFR | HER2 | HER3 | Cetuximab | Trastuzumab | MM-121 | Negative control |
|---|---|---|---|---|---|---|---|---|---|---|---|---|---|---|
| 1 | Breast | Ductal Carcinoma | MDA-MB175-VII | 13 | 75 | 35 | 30 | 120 | 80 | 50 | 120 | 100 | 50 | 150 |
| 2 | Lung | Adenocarcinoma | HCC827 | 15 | 43 | 19 | 75 | 75 | 100 | 79 | 31 | 82 | 75 | 90 |
| 3 | Head and Neck | HNSCC | HN5 | 15 | 15 | 25 | 100 | 85 | 125 | 115 | 100 | 165 | 120 | 95 |
| 4 | Head and Neck | Pharyngeal Squamous cell carcinoma | FaDu | 18 | 20 | 23 | 65 | 110 | 120 | 100 | 95 | 90 | 85 | 100 |
| 5 | Breast | Carcinoma | HCC1937 | 20 | 51 | 38 | 75 | 75 | 100 | 85 | 95 | 100 | 97 | 105 |
| 6 | Skin | Epidermoid carcinoma | A431-NS | 20 | 88 | 35 | 75 | 75 | 100 | 80 | 90 | 100 | 90 | 115 |
| 7 | Oesophagus | Squamous cell carcinoma | TE11 | 20 | 54 | 38 | 70 | 75 | 100 | 95 | 95 | 100 | 97 | 105 |
| 8 | Breast | Ductal Carcinoma | MDA-MB175-VII | 25 | 95 | 80 | 50 | 125 | 95 | 75 | 115 | 120 | 85 | 140 |
| 9 | Ovary | Adenocarcinoma | RMG-I | 25 | 100 | 38 | 40 | 130 | 150 | 140 | 135 | 105 | 105 | 180 |
| 10 | Colon | | GEO | 29 | 80 | 48 | 120 | 130 | 125 | 120 | 130 | 125 | 125 | 150 |
| 11 | Lung | Adenocarcinoma | H358 (NCI-H358) | 30 | 38 | 37 | 66 | 100 | 75 | 87 | 95 | 73 | 65 | 90 |
| 12 | Gastric | Carcinoma | N87 (NCI-N87) | 30 | 130 | 110 | 25 | 210 | 125 | 95 | 180 | 185 | 100 | 250 |
| 13 | Lung | Mucoepidermoid Carcinoma | H292 (NCI-H292) | 32 | 64 | 60 | 94 | 89 | 119 | 116 | 131 | 139 | 118 | 150 |
| 14 | Oesophagus | Squamous cell carcinoma | KYSE520 | 34 | 41 | 41 | 31 | 47 | 100 | 60 | 50 | 85 | 85 | 100 |
| 15 | Colon | Adenocarcinoma | LS-174T | 40 | 41 | 49 | 95 | 50 | 113 | 111 | 126 | 122 | 112 | 144 |
| 16 | Gastric | Adenocarcinoma | OE19 | 40 | 130 | 115 | 50 | 160 | 130 | 105 | 155 | 140 | 80 | 150 |
| 17 | Lung | Adenocarcinoma | CALU-3 | 45 | 120 | 50 | 85 | 150 | 180 | 100 | 125 | 155 | 75 | 200 |
| 18 | Colon | Carcinoma | COLO678 | 48 | 74 | 60 | 88 | 100 | 120 | 115 | 130 | 130 | 93 | 125 |
| 19 | Gastric | Adenocarcinoma | OE19 | 50 | 90 | 130 | 50 | 160 | 140 | 115 | 105 | 120 | 120 | 170 |
| 20 | Lung | Adenocarcinoma | H520 (NCI-H520) | 51 | 72 | 68 | 96 | 117 | 100 | 61 | 107 | 105 | 71 | 140 |
| 21 | Breast | Carcinoma | BT474 | 55 | 130 | 110 | 50 | 150 | 130 | 110 | 130 | 140 | 115 | 170 |
| 22 | Pancreas | Adenocarcinoma | CAPAN-1 | 55 | 110 | 70 | 100 | 100 | 110 | 90 | 150 | 150 | 95 | 210 |
| 23 | Pancreas | Carcinoma | PK-1 | 57 | 85 | 62 | 82 | 97 | 105 | 87 | 100 | 100 | 90 | 105 |
| 24 | Pancreas | Adenocarcinoma | ASPC1 | 58 | 70 | 64 | 105 | 200 | 178 | 90 | 205 | 160 | 95 | 240 |
| 25 | Endometrium | Carcinoma | RL95-2 | 60 | 75 | 85 | 100 | 83 | 120 | 100 | 80 | 120 | 120 | 100 |
| 26 | Pancreas | Carcinoma | BxPC3 | 60 | 55 | 65 | 70 | 120 | 88 | 60 | 125 | 100 | 86 | 120 |
| 27 | Oesophagus | Squamous cell carcinoma | COLO680N | 60 | 55 | 70 | 95 | 118 | 115 | 110 | 125 | 120 | 100 | 140 |
| 28 | Pancreas | Carcinoma | CAPAN-2 | 62 | 70 | 75 | 34 | 75 | 75 | 81 | 77 | 88 | 70 | 100 |
| 29 | Skin | Epidermoid carcinoma | A-431 | 65 | 80 | 70 | 100 | 133 | 118 | 100 | 110 | 95 | 85 | 100 |
| 30 | Endometrium | Adenocarcinoma | MFE-280 | 65 | 65 | 65 | 70 | 110 | 100 | 65 | 95 | 75 | 55 | 100 |
| 31 | Breast | Ductal Carcinoma | HCC202 | 70 | 116 | 110 | 90 | 91 | 195 | 112 | 121 | 120 | 115 | 97 |
| 32 | Colon | Adenocarcinoma | CaCO2 | 70 | 100 | 75 | 90 | 100 | 100 | 85 | 100 | 100 | 90 | 120 |
| 33 | Ovary | Cystadenocarcinoma | RMUG-S | 70 | 100 | 95 | 90 | 105 | 110 | 105 | 115 | 110 | 110 | 140 |
| 34 | Colon | Colorectal carcinoma | T84 | 75 | 85 | 60 | 75 | 100 | 95 | 80 | 100 | 100 | 95 | 100 |
| 35 | Ovary | Adenocarcinoma | OVCAR-8 | 75 | 105 | 97 | 97 | 104 | 100 | 95 | 100 | 107 | 93 | 101 |
| 36 | Pancreas | Adenocarcinoma | Panc08.13 | 75 | 50 | 60 | 90 | 110 | 115 | 105 | 110 | 115 | 95 | 120 |
| 37 | Pancreas | Adenocarcinoma, ductal | CFPAC-1 | 75 | 95 | 88 | 100 | 175 | 120 | 110 | 100 | 149 | 95 | 170 |
| 38 | Colon | Rectal adenocarcinoma | SW1463 | 75 | 95 | 80 | 120 | 150 | 120 | 100 | 145 | 125 | 110 | 175 |
| 39 | Breast | Adenocarcinoma | MDA-MB-468 | 79 | 87 | 71 | 92 | 82 | 135 | 110 | 95 | 148 | 100 | 134 |
| 40 | Endometrium | Endometrial Adenocarcinoma | HEC-108 | 80 | 105 | 110 | 220 | 90 | 100 | 110 | 90 | 85 | 95 | 100 |
| 41 | Breast | Adenocarcinoma | CAL-120 | 80 | 80 | 80 | 95 | 85 | 85 | 90 | 85 | 70 | 75 | 100 |
| 42 | Ovary | Adenocarcinoma | IGR-OV1 | 80 | 120 | 140 | 150 | 80 | 85 | 125 | 120 | 120 | 150 | 105 |
| 43 | Colon | Rectal adenocarcinoma | SW837 | 80 | 125 | 105 | 120 | 150 | 120 | 130 | 145 | 130 | 125 | 165 |
| 44 | Urinary tract | Carcinoma | RT-4 | 80 | 110 | 80 | 100 | 200 | 100 | 100 | 135 | 125 | 105 | 180 |
| 45 | Oesophagus | Adenocarcinoma (lower third) | OE33 | 80 | 105 | 67 | 88 | 122 | 118 | 87 | 120 | 130 | 94 | 148 |
| 46 | Ovary | Adenocarcinoma | SKOV3 | 82 | 88 | 81 | 117 | 87 | 89 | 115 | 110 | 105 | 117 | 112 |
| 47 | Pancreas | Ductal carcinoma | PANC-1 | 85 | 70 | 70 | 100 | 100 | 80 | 50 | 75 | 85 | 70 | 85 |
| 48 | Colon | Adenocarcinoma | LoVo | 85 | 100 | 100 | 110 | 110 | 110 | 105 | 105 | 100 | 100 | 115 |
| 49 | Colon | Colorectal adenocarcinoma | SW403 | 85 | 140 | 100 | 100 | 200 | 190 | 120 | 200 | 185 | 100 | 260 |
| 50 | Prostate | Carcinoma | DU145 | 85 | 107 | 95 | 103 | 117 | 100 | 100 | 110 | 85 | 100 | 95 |
| 51 | Lung | Adenocarcinoma | H1437 (NCI-H1437) | 88 | 85 | 85 | 95 | 101 | 100 | 90 | 113 | 113 | 95 | 118 |
| 52 | Lung | Squamous cell carcinoma, Mesothelioma | H226 (NCI-H226) | 90 | 105 | 100 | 90 | 100 | 100 | 100 | 100 | 105 | 100 | 110 |
| 53 | Gastric | Gastric carcinoma | KATOIII | 90 | 115 | 95 | 90 | 115 | 100 | 95 | 110 | 110 | 100 | 110 |
| 54 | Bone | Osteosarcoma | U2-OS | 90 | 100 | 90 | 100 | 100 | 100 | 100 | 100 | 100 | 105 | 120 |
| 55 | Ovary | Adenocarcinoma | OVCAR-3 | 90 | 130 | 130 | 110 | 115 | 140 | 145 | 120 | 145 | 135 | 130 |
| 56 | Urinary tract | Carcinoma | RT-112 | 90 | 120 | 55 | 100 | 150 | 100 | 100 | 140 | 120 | 110 | 140 |
| 57 | Breast | Ductal Carcinoma | ZR-75-30 | 90 | 120 | 130 | 120 | 120 | 125 | 120 | 115 | 160 | 150 | 150 |
| 58 | Colon | Colorectal carcinoma | LS1034 | 90 | 111 | 85 | 72 | 140 | 100 | 90 | 170 | 151 | 95 | 155 |
| 59 | Breast | Adenocarcinoma | MCF7 | 90 | 200 | 170 | 120 | 220 | 155 | 130 | 220 | 205 | 135 | 220 |
| 60 | Lung | Squamous cell carcinoma | H520 (NCI-H520) | 93 | 95 | 100 | 105 | 95 | 95 | 100 | 103 | 84 | 107 | 105 |
| 61 | Skin | Melanoma | A2058 | 95 | 95 | 95 | 95 | 90 | 100 | 85 | 95 | 100 | 100 | 85 |
| 62 | Gastric | Carcinoma | SNU-5 | 95 | 90 | 90 | 95 | 100 | 90 | 90 | 95 | 95 | 100 | 100 |
| 63 | Ovary | Epithelial serous carcinoma, pleural effusion | COV504 | 95 | 100 | 100 | 105 | 110 | 105 | 100 | 95 | 110 | 110 | 110 |
| 64 | Lung | Squamous cell carcinoma | SBC1 | 95 | 115 | 110 | 120 | 110 | 105 | 105 | 85 | 100 | 95 | 120 |
| 65 | Lung | Adenocarcinoma | A549 | 95 | 100 | 100 | 115 | 115 | 105 | 110 | 95 | 90 | 105 | 135 |
| 66 | Breast | Adenocarcinoma | AU-565 | 95 | 100 | 130 | 105 | 150 | 150 | 125 | 130 | 130 | 135 | 145 |
| 67 | Ovary | Adenocarcinoma | OVCAR-5 | 95 | 100 | 95 | 115 | 140 | 140 | 130 | 120 | 130 | 120 | 135 |
| 68 | Brain | Glioblastoma | SKMG3 | 95 | 92 | 85 | 73 | 100 | 95 | 85 | 95 | 93 | 87 | 88 |
| 69 | Breast | Adenocarcinoma | SK-BR-3 | 95 | 130 | 130 | 105 | 120 | 114 | 106 | 125 | 125 | 115 | 130 |
| 70 | Colon | Adenocarcinoma | GP5d | 100 | 120 | 95 | 112 | 150 | 125 | 120 | 150 | 150 | 120 | 171 |
| 71 | Breast | Ductal carcinoma | MDA-MB-134-VI | 105 | 113 | 112 | 100 | 143 | 100 | 105 | 140 | 130 | 85 | 152 |
| 72 | Prostate | Carcinoma | LoCAP FGC | 105 | 105 | 110 | 120 | 130 | 150 | 100 | 100 | 155 | 85 | 200 |
| 73 | Urinary tract | Urinary bladder transitional carcinoma | BFTC-905 | 110 | 150 | 100 | 85 | 200 | 180 | 110 | 180 | 175 | 100 | 160 |
| 74 | Breast | Carcinoma | CAL-51 | 115 | 142 | 100 | 143 | 159 | 148 | 150 | 150 | 148 | 155 | 155 |
| 75 | Colon | Adenocarcinoma | SW620 | 124 | 123 | 120 | 115 | 140 | 120 | 120 | 150 | 148 | 132 | 152 |
| 76 | Ovary | Adenocarcinoma | OVCAR-4 | 135 | 200 | 220 | 220 | 250 | 250 | 200 | 200 | 220 | 175 | 300 |

Figure 25

| | Origin | Subtype | Cell line | Pan-HER | EGFR+HER2 | EGFR+HER3 | HER2+HER3 | EGFR | HER2 | HER3 | Cetuximab | Trastuzumab | MM-121 | Negative control |
|---|---|---|---|---|---|---|---|---|---|---|---|---|---|---|
| 1 | Breast | Ductal Carcinoma | MDA-MB175-VII | 10 | 50 | 20 | 40 | 85 | 70 | 55 | 90 | 75 | 50 | 115 |
| 2 | Colon | Adenocarcinoma | LS-174T | 13 | 23 | 18 | 114 | 20 | 118 | 95 | 51 | 108 | 120 | 135 |
| 3 | Gastric | Carcinoma | N87 (NCI-N87) | 15 | 15 | 30 | 215 | 95 | 230 | 280 | 115 | 195 | 200 | 270 |
| 4 | Head and Neck | Pharyngeal Squamous cell carcinoma | FaDu | 17 | 20 | 17 | 100 | 31 | 98 | 59 | 77 | 83 | 85 | 94 |
| 5 | Breast | Ductal Carcinoma | MDA-MB175-VII | 20 | 65 | 35 | 65 | 90 | 80 | 80 | 90 | 80 | 65 | 105 |
| 6 | Gastric | Adenocarcinoma | OE19 | 25 | 20 | 35 | 70 | 80 | 60 | 130 | 90 | 85 | 103 | 130 |
| 7 | Ovary | Adenocarcinoma | RMG-I | 25 | 25 | 25 | 170 | 23 | 180 | 190 | 90 | 185 | 175 | 170 |
| 8 | Lung | Adenocarcinoma | H358 (NCI-H358) | 27 | 36 | 29 | 66 | 38 | 59 | 81 | 89 | 95 | 92 | 97 |
| 9 | Colon | | GEO | 27 | 35 | 30 | 144 | 23 | 133 | 113 | 100 | 130 | 137 | 136 |
| 10 | Breast | Carcinoma | BT474 | 30 | 30 | 30 | 25 | 120 | 35 | 75 | 100 | 35 | 70 | 105 |
| 11 | Gastric | Adenocarcinoma | OE19 | 35 | 40 | 90 | 90 | 95 | 90 | 110 | 105 | 95 | 105 | 120 |
| 12 | Lung | Adenocarcinoma | CALU-3 | 35 | 40 | 45 | 170 | 55 | 140 | 140 | 65 | 140 | 140 | 165 |
| 13 | Lung | Mucoepidermoid Carcinoma | H292 (NCI-H292) | 39 | 36 | 34 | 142 | 38 | 137 | 129 | 107 | 133 | 136 | 139 |
| 14 | Pancreas | Adenocarcinoma | ASPC1 | 39 | 42 | 39 | 153 | 49 | 148 | 143 | 73 | 148 | 142 | 163 |
| 15 | Colon | Rectal adenocarcinoma | SW948 | 44 | 35 | 44 | 210 | 28 | 83 | 111 | 105 | 200 | 178 | 300 |
| 16 | Breast | Carcinoma | HCC1937 | 45 | 56 | 58 | 96 | 78 | 94 | 97 | 98 | 87 | 95 | 103 |
| 17 | Breast | Ductal Carcinoma | HCC202 | 49 | 58 | 81 | 98 | 85 | 113 | 117 | 87 | 112 | 113 | 126 |
| 18 | Lung | Adenocarcinoma | H820 (NCI-H820) | 53 | 48 | 58 | 90 | 72 | 48 | 76 | 76 | 102 | 102 | 114 |
| 19 | Colon | Rectal adenocarcinoma | SW1463 | 55 | 60 | 70 | 150 | 65 | 145 | 130 | 75 | 115 | 130 | 155 |
| 20 | Oesophagus | Adenocarcinoma (lower third) | OE33 | 57 | 81 | 72 | 105 | 53 | 75 | 108 | 72 | 93 | 100 | 98 |
| 21 | Pancreas | Carcinoma | BxPC3 | 58 | 65 | 57 | 93 | 100 | 95 | 91 | 100 | 105 | 103 | 100 |
| 22 | Endometrium | Adenocarcinoma | MFE-280 | 60 | 65 | 50 | 70 | 95 | 75 | 65 | 95 | 75 | 60 | 95 |
| 23 | Pancreas | Adenocarcinoma | CAPAN-1 | 60 | 50 | 50 | 130 | 55 | 135 | 130 | 88 | 140 | 140 | 146 |
| 24 | Oesophagus | Squamous cell carcinoma | COLO680N | 61 | 48 | 61 | 151 | 58 | 148 | 135 | 128 | 164 | 138 | 150 |
| 25 | Prostate | Carcinoma | DU145 | 65 | 71 | 59 | 100 | 86 | 97 | 90 | 94 | 100 | 100 | 100 |
| 26 | Colon | Adenocarcinoma | CaCO2 | 65 | 65 | 65 | 110 | 60 | 90 | 100 | 75 | 105 | 105 | 120 |
| 27 | Pancreas | Carcinoma | PK-1 | 67 | 76 | 66 | 89 | 88 | 70 | 78 | 87 | 85 | 71 | 94 |
| 28 | Colon | Carcinoma | COLO678 | 68 | 67 | 59 | 125 | 48 | 129 | 115 | 115 | 117 | 102 | 107 |
| 29 | Endometrium | Carcinoma | RL95-2 | 68 | 69 | 78 | 125 | 87 | 100 | 158 | 118 | 100 | 129 | 130 |
| 30 | Breast | Adenocarcinoma | SK-BR-3 | 73 | 81 | 89 | 87 | 96 | 90 | 88 | 75 | 95 | 100 | 96 |
| 31 | Pancreas | Carcinoma | CAPAN-2 | 75 | 65 | 74 | 93 | 71 | 91 | 76 | 62 | 88 | 86 | 95 |
| 32 | Gastric | Gastric carcinoma | KATOII | 75 | 80 | 80 | 90 | 100 | 60 | 95 | 100 | 85 | 100 | |
| 33 | Ovary | Cystadenocarcinoma | RMUG-S | 75 | 70 | 65 | 100 | 85 | 100 | 100 | 100 | 105 | 100 | 115 |
| 34 | Pancreas | Adenocarcinoma | Panc02.13 | 75 | 90 | 95 | 130 | 90 | 130 | 130 | 89 | 140 | 120 | 125 |
| 35 | Ovary | Adenocarcinoma | OVCAR-3 | 75 | 75 | 95 | 125 | 90 | 135 | 115 | 125 | 130 | 135 | |
| 36 | Ovary | Adenocarcinoma | IGR-OV1 | 75 | 50 | 75 | 130 | 65 | 150 | 150 | 80 | 190 | 180 | 150 |
| 37 | Pancreas | Adenocarcinoma, ductal | CFPAC-1 | 75 | 65 | 80 | 160 | 85 | 155 | 160 | 95 | 155 | 165 | 160 |
| 38 | Lung | Adenocarcinoma | H1437 (NCI-H1437) | 76 | 89 | 73 | 88 | 82 | 85 | 102 | 84 | 87 | 108 | 97 |
| 39 | Ovary | Adenocarcinoma | OVCAR-8 | 77 | 71 | 52 | 85 | 81 | 95 | 78 | 96 | 82 | 95 | 96 |
| 40 | Colon | Adenocarcinoma | GP5d | 78 | 87 | 84 | 164 | 62 | 141 | 155 | 112 | 115 | 167 | 192 |
| 41 | Colon | Adenocarcinoma | LoVo | 80 | 85 | 90 | 90 | 90 | 90 | 85 | 90 | 90 | 90 | 95 |
| 42 | Pancreas | Ductal carcinoma | PANC-1 | 80 | 80 | 90 | 90 | 90 | 90 | 85 | 85 | 90 | 90 | 100 |
| 43 | Colon | Colorectal carcinoma | T84 | 80 | 70 | 80 | 110 | 75 | 100 | 100 | 65 | 115 | 125 | 115 |
| 44 | Lung | Large cell carcinoma | H661 (NCI-H661) | 80 | 75 | 80 | 95 | 100 | 90 | 90 | 95 | 95 | 95 | 120 |
| 45 | Colon | Rectal adenocarcinoma | SW837 | 80 | 95 | 85 | 155 | 60 | 130 | 135 | 100 | 125 | 130 | 150 |
| 46 | Ovary | Adenocarcinoma | SKOV3 | 81 | 83 | 88 | 127 | 88 | 130 | 121 | 91 | 102 | 127 | 129 |
| 47 | Breast | Carcinoma | BT20 | 85 | 77 | 77 | 93 | 78 | 98 | 95 | 88 | 94 | 91 | 91 |
| 48 | Lung | Adenocarcinoma | H1993 (NCI-H1993) | 85 | 90 | 90 | 95 | 85 | 90 | 90 | 85 | 90 | 95 | 100 |
| 49 | Gastric | Carcinoma | SNU-16 | 85 | 100 | 100 | 105 | 75 | 100 | 100 | 78 | 90 | 90 | 100 |
| 50 | Breast | Adenocarcinoma | MCF7 | 85 | 110 | 125 | 105 | 80 | 110 | 135 | 100 | 100 | 110 | 130 |
| 51 | Muscle | Rhabdomyosarcoma | RD | 85 | 85 | 100 | 120 | 100 | 100 | 105 | 50 | 110 | 125 | 140 |
| 52 | Colon | Adenocarcinoma | HT29 | 90 | 85 | 90 | 105 | 100 | 90 | 90 | 70 | 90 | 105 | 100 |
| 53 | Breast | Carcinoma | MDA-MB-157 | 90 | 95 | 100 | 90 | 100 | 105 | 100 | 95 | 95 | 100 | |
| 54 | Ovary | Adenocarcinoma | OVCAR-5 | 90 | 75 | 80 | 115 | 85 | 120 | 120 | 95 | 120 | 110 | 115 |
| 55 | Urinary tract | Carcinoma | RT-112 | 90 | 100 | 90 | 130 | 95 | 135 | 130 | 125 | 130 | 135 | 130 |
| 56 | Colon | Colorectal adenocarcinoma | SW403 | 90 | 65 | 70 | 120 | 75 | 110 | 125 | 100 | 100 | 105 | 150 |
| 57 | Urinary tract | Carcinoma | RT-4 | 90 | 75 | 75 | 140 | 70 | 160 | 158 | 110 | 155 | 170 | 170 |
| 58 | Breast | Ductal carcinoma | MDA-MB-134-VI | 95 | 85 | 85 | 100 | 110 | 90 | 90 | 88 | 89 | 90 | 95 |
| 59 | Breast | Carcinoma | MDA-MB-453 | 95 | 95 | 75 | 90 | 100 | 100 | 90 | 95 | 70 | 75 | 100 |
| 60 | Lung | Squamous cell carcinoma | H520 (NCI-H520) | 95 | 92 | 105 | 92 | 93 | 99 | 91 | 93 | 93 | 93 | 104 |
| 61 | Lung | Squamous cell carcinoma | EBC1 | 95 | 98 | 100 | 100 | 85 | 105 | 95 | 65 | 90 | 100 | 115 |
| 62 | Urinary tract | Urinary bladder transitional carcinoma | BFTC-905 | 95 | 95 | 95 | 110 | 100 | 105 | 110 | 100 | 110 | 110 | 115 |
| 63 | Colon | Adenocarcinoma | HCT-116 | 97 | 81 | 92 | 99 | 98 | 100 | 80 | 92 | 91 | 101 | 96 |
| 64 | Breast | Carcinoma | CAL-51 | 100 | 99 | 105 | 144 | 105 | 147 | 144 | 123 | 133 | 126 | 144 |
| 65 | Prostate | Carcinoma | LnCAP FGC | 100 | 99 | 90 | 100 | 120 | 130 | 125 | 110 | 130 | 120 | 175 |
| 66 | Lung | Adenocarcinoma | A549 | 105 | 100 | 100 | 100 | 105 | 125 | 130 | 110 | 100 | 120 | 140 |
| 67 | Lung | Squamous cell carcinoma | H1703 (NCI-H1703) | 107 | 95 | 109 | 273 | 98 | 225 | 300 | 119 | 238 | 230 | 322 |
| 68 | Lung | Large cell carcinoma, lymph node metastasis | H1299 (NCI-H1299) | 110 | 105 | 105 | 130 | 105 | 125 | 125 | 110 | 150 | 110 | 150 |
| 69 | Ovary | Adenocarcinoma | OVCAR-4 | 110 | 80 | 85 | 210 | 95 | 200 | 205 | 120 | 200 | 220 | 250 |
| 70 | Breast | Adenocarcinoma | AU-565 | 115 | 60 | 75 | 75 | 100 | 115 | 120 | 50 | 95 | 125 | 125 |
| 71 | Lung | Squamous cell carcinoma, Mesothelioma | H226 (NCI-H226) | 135 | 148 | 140 | 175 | 130 | 165 | 135 | 133 | 165 | 170 | 173 |

METHODS FOR TREATING CANCER BY ADMINISTERING HUMANIZED PAN-HER ANTIBODY COMPOSITIONS

CROSS REFERENCES TO OTHER APPLICATIONS

This application is a divisional application of U.S. patent application Ser. No. 14/398,441, filed Oct. 31, 2014, issued on Dec. 27, 2016 as U.S. Pat. No. 9,527,913, which is a national stage application under 35 U.S.C. § 371 of International Patent Application No. PCT/IB2013/001027, filed on May 2, 2013, which claims priority from U.S. Provisional Application 61/641,756, filed May 2, 2012, and from U.S. Provisional Application 61/809,159, filed Apr. 5, 2013. The disclosures of those applications are incorporated by reference herein in their entirety.

FIELD OF THE INVENTION

The present invention relates to novel humanized recombinant antibodies targeting the epidermal growth factor receptor (EGFR) family and compositions comprising two or more of these antibodies for use in cancer therapy.

BACKGROUND OF THE INVENTION

The epidermal growth factor receptor family (EGFR or ErbB/HER family) is a subgroup of the receptor tyrosine kinases (RTKs) and includes four members: EGFR/ErbB, HER2/ErbB2, HER3/ErbB3 and HER4/ErbB4. The members of the EGFR family are closely related single-chain modular glycoproteins with an extracellular ligand binding region, a single transmembrane domain and an intracellular tyrosine kinase domain. In normal physiological settings the ErbB family regulates key events in coordination of cell growth, differentiation and migration. EGFR, HER2 and HER3 are believed to play crucial roles in the malignant transformation of normal cells and in the continued growth of cancer cells. EGFR and HER2 have been found to be overexpressed by many epithelial cancers. Overexpression of EGFR and HER2 has furthermore been linked to disease progression, reduced survival, poor response and chemotherapy resistance in several human epithelial cancers. The role of HER0 in malignant transformation and cancer progression is controversial and will not be discussed further here.

EGFR and HER2 are validated cancer targets and both monoclonal antibodies and small molecule inhibitors of their tyrosine kinase have been approved for the treatment of various cancers. HER3 is currently being explored as a potential therapeutic target. However, patients who initially respond to these therapies often relapse due to evolvement of acquired resistance. Pre-clinical research points to the involvement of the one or both of the non-targeted receptors in the development of resistance. Thus, it appears that the ErbB receptors have the ability to replace one another in order to maintain growth stimulatory signaling and a malignant phenotype. Simultaneous targeting of two or all three receptors could therefore be a more efficient way of inhibiting cancer cells with ErbB family dependency.

EGFR is a 170 kDa cell surface glycoprotein consisting of a single polypeptide chain of 1186 amino acid residues as originally determined and described by cloning and sequencing of human cDNAs from a human vulval carcinoma cell line. EGFR contains three major domains: an extracellular domain, a transmembrane domain and an intracellular domain containing the tyrosine kinase. The catalytic activity of EGFR resides in the tyrosine kinase domain (residues 685-953) and is activated upon ligand binding.

The EGFR exists in two different conformations, namely a tethered conformation (closed) and an extended conformation (open). The receptor shifts between the two conformations. In the tethered conformation domains II and IV of the extracellular region of EGFR interact, leaving the receptor in an autoinhibited state. Furthermore, domain III is held at a significant distance from domain I, whereby binding of EGF to both domains simultaneously is impossible. In the extended conformation of EGFR, domains I, II and III are sterically arranged in a C shape, giving room for EGF binding. Furthermore, the conformational changes induce exposure of a β-hairpin consisting of a 20 residue region in domain II, also known as the "dimerization arm". The dimerization arm extending from domain II of the EGFR makes extensive contacts with the domain II of another EGFR, thereby forming an EGFR homodimer.

Dimerization brings the active cytoplasmic tyrosine kinase domains of the receptors close enough for phosphorylation of the tyrosine residues in the regulatory regions of the receptors. Furthermore, the juxtamembrane regions of the two receptors form an antiparallel dimer which has been found to be important in stabilizing the tyrosine kinase dimer. The "receptor-mediated" dimerization mechanism is unique for the ErbB family compared to other tyrosine kinase receptors where "ligand-mediated" dimerization is the more common theme.

A number of modes of activation of the intracellular tyrosine kinase domain of EGFR have been suggested. Unlike other receptor tyrosine kinases, the EGFR tyrosine kinase domain by default adopts a conformation normally observed only in phosphorylated and activated kinases. This indicates that the kinase domain of EGFR is constructively active. Regulation of a constitutive tyrosine kinase would thus occur through the delivery of a dimerization partner's C-terminal regulator region for trans-phosphorylation. Another possibility is that activation of the tyrosine kinase domain involves displacement of inhibitory interactions that have not been visualized in crystallographic studies. However, crystal structure analyses of the juxtamembrane and tyrosine kinase of EGFR have revealed that an asymmetric dimer of tyrosine kinases formed upon dimerization of two EGFRs is important for regulation of the tyrosine kinase activity. In this asymmetric homodimer one of the tyrosine kinases plays the receiver while the other tyrosine kinase plays the donor. Only the receiver kinase domain has catalytic activity and proceeds to phosphorylate tyrosine residues in the C-terminal tail of the receptor (whether in cis or trans, or both is unknown).

The clathrin-mediated endocytosis is the most important mechanism of down-regulation of EGFR. The destiny of EGFR depends on the stability of the ligand-receptor complex. Upon EGF binding to EGFR the EGFR homodimer is rapidly targeted to clathrin-coated pits and internalized through ligand-induced endocytosis. Simultaneously, EGFR is heavily ubiquitinated by the attachment of both monoubiquitin and polyubiquitin. The ubiquitin ligase Cbl is responsible for the ubiquitination of EGFR. Cbl binds either directly or indirectly through an adaptor protein such as Grb2 to phosphorylated tyrosine residues at the regulatory region of EGFR. The binding of Cbl to EGFR via Grb2 is necessary for receptor internalization. Esp15 also plays a role in EGFR internalization. The exact role of Esp15 is however still controversial. The ubiquitination is involved in endocytotic downregulation of EGFR and endosomal sorting of EGFR to lysosomes. The ubiquitin chains are recognized by the endosomal sorting complex required for transport (ESCRT) and the Hrs/STAM, which retains ubiquinated proteins in the membrane of early endosomes, thereby hindering recycling of EGFR. Subsequently, EGFR is sorted into intra luminal vesicles (ILVs), which leads to delivery of EGFR to the late endosome and finally degradation in the lysosomes.

In contrast to the degradation of EGFR when bound to EGF, TGF-α binding allows receptor recycling. The TGF-α ligand dissociates rapidly from EGFR in the early endosome due to the acidic environment, leading to receptor dephosphorylation, de-ubiquitination and thereby recycling of the receptor back to the cell surface.

Human epidermal growth factor receptor 2 (HER2, ErbB2 or Neu) was first described in 1984 by Schechter et al, HER2 consists of 1234 amino acids and is structurally similar to EGFR with an extracellular domain consisting of four subdomains I-IV, a transmembrane domain, a juxtamembrane domain, an intracellular cytoplasmic tyrosine kinase and a regulatory C-terminal domain.

The domain II-IV contact that restricts the domain arrangement in the tethered EGFR is absent in HER2. Three of the seven conserved residues important for stabilizing the tether in the unactivated EGFR are different in HER2. HER2 thus resembles EGFR in its extended (open) form with the dimerization arm exposed and apparently poised to drive receptor-receptor interactions. The absence of a tethered HER2 conformation indicates that the receptor lacks auto-inhibition as seen for the other members of the ErbB family. A stable interface of subdomain I-III seems to keep HER2 in the extended configuration similar to the extended configuration of the EGFR-EGF complex. The interaction between domains I and III involves regions corresponding to ligand-binding sites in domains I and III of EGFR, leaving no space sterically for ligands, rendering HER2 incapable of binding ligands. Domains II and IV form two distinct interfaces that stabilize the heterodimer formation of HER2 and another member of the ErbB family.

Biophysical studies have failed to detect significant HER2 homodimerization in solution or in crystals. The residues of domain II of EGFR and HER2 are similar. However, Arg285 at the dimer interface is not conserved between EGFR and HER2. In HER2 residue 285 is Leu. Mutation studies indicate that Leu at this position is partly responsible for the absence of HER2 homodimers in solution. Dimerization of intact HER2 in vivo may require additional interactions of sites in the transmembrane domain of HER2.

HER2 is the only member of the ErbB family that does not bind known ligands, HER2 is instead activated via formation of heteromeric complexes with other ErbB family members and thereby indirectly regulated by EFGR and HER3 ligands. HER2 is the preferred heterodimerization partner of the three other ErbB receptors. HER2 enhances the affinity of the other ErbB receptors for their ligands by slowing down the rate of ligand receptor complex dissociation, whereby HER2 enhances and prolongs signaling. The ability of HER2 to enhance the ligand affinity of other ErbB receptors may reflect the promiscuous behavior of HER2 as a heterodimerization partner. Heterodimerization of HER2 and another ligand-bound receptor of the ErbB family induces cross-phosphorylation, leading to phosphorylation of the C-terminal tyrosine residues. The most active HER2 heterodimer is the HER2-HER3 complex, HER2 complements the kinase-deficient HER3 by providing an active kinase.

In contrast to EGFR, HER2 is internalization resistant when overexpressed. Overexpression of HER2 has further been reported to inhibit endocytosis of the other ErbB family members. Two mechanisms by which HER2 escapes lysosomal degradation and thereby remains at the plasma membrane have been suggested. Either HER2 avoids internalization or it becomes efficiently recycled from endosomes back to the plasma membrane. Studies using labeled antibodies have shown that HER2 is constantly internalized and recycled. Other studies in contrast failed to identify intracellular HER2 in cells treated with compounds known to inhibit recycling.

It has been proposed that the carboxyl terminus of HER2 does not possess all signals required for internalization or that it contains an inhibitory signal essential for clathrin-mediated endocytosis. Additionally, studies have shown that HER2 heterodimers are not delivered to endosomes. A Cbl docking site like the one found on EGFR has also been identified on HER2 (Y1112). Cbl can thereby be recruited to HER2, leading to ubiquitination of HER2, but the actual binding efficiency of Cbl is unclear. It has been proposed that HER2 is internalization resistant due to its association with membrane protrusions. Finally, other studies have shown that the endocytosis resistance of HER2-EGFR heterodimers is associated with inefficient EGF-induced formation of clathrin-coated pits.

The third member of the ErbB family, known as human epidermal growth factor receptor 3 (HERB, ErbB3) was identified in 1989 by Kraus M. H. et al. The HER3 gene encodes a protein of 1342 amino acids with striking structural similarities to EGFR and HER2. Features such as overall size, four extracellular subdomains (I-IV) with two cysteine clusters (domains II and IV), and a tyrosine kinase domain show structural similarities to EGFR and HER2. The tyrosine kinase domain of HER3 shows 59% sequence homology to the tyrosine kinase domain of EGFR.

Just like EGFR, HER3 exists in a tethered conformation and an extended conformation. In the tethered conformation the dimerization arm is buried by interactions with domain IV, leaving domains I and III too far apart for efficient ligand binding. Ligand binding to the extracellular domains I and III occurs in the extended conformation of HER3 and leads to heterodimerization with other members of the ErbB family. No HER3 homodimers are formed upon ligand binding. The extended and ligand-bound HER3 molecule preferentially heterodimerizes with HER2.

In contrast to EGFR and HER2, the tyrosine kinase of HER3 has impaired catalytic activity, insufficient for any detectable biological response. Two amino acid residues which are highly conserved in the catalytic domains of protein kinases are altered in the catalytic domain of HER3. These are the substitution of asparagine for aspartic acid at residue 815 and substitution of histidine for glutamate at residue 740. The two amino acid substitutions may be the reason why HERB lacks catalytic activity of its tyrosine kinase domain. Because of the impaired intrinsic kinase activity of HER3 the receptor needs to heterodimerize with another ErbB family member in order to respond to its own ligand binding.

Little is known about endocytosis of HER3. Moreover, different studies have suggested that HER3 is endocytosis impaired to the same extent as HER2. In agreement with this, the HER3-NRG1 complex was found to be internalized less efficiently and slower than the EGFR-EGF complex, supporting the view that HER3 is not endocytosed as efficiently as EGFR. However, when the C-terminal tail of EGFR was replaced with the C-terminal tail of HER3, EGFR became endocytosis impaired, suggesting that a region in the C-terminus of HER3 protects the receptor against internalization. It has also been suggested that NRG1 does not efficiently target HER3 to degradation due to the dissociation of the ligand-receptor complexes in endosomes, as it is observed when EGF is activated by TGFα.

Targeting the ErbB family has been intensely pursued in the last decade as a cancer treatment strategy. Different treatment modalities have been explored, such as tyrosine kinase inhibitors (TKIs), monoclonal antibodies (mAbs) and ligand-traps. An advantage of monoclonal antibodies for treatment of cancer is target specificity, ensuring a low toxicity compared to conventional cytotoxic cancer chemotherapy. Monoclonal antibodies have been approved for the treatment of solid tumors with abnormally high levels of EGFR or HER2, and numerous mAbs targeting EGFR or HER2 are in clinical trials. TKIs inhibit receptor signaling by binding to the ATP-binding site in the tyrosine kinase domain of EGFR and HER2. Erlotinib/Tarceva® inhibits tyrosine kinases of EGFR while lapatinib/Tykerb® inhibits tyrosine kinases of both EGFR and HER2. Both erlotinib and laptinib are FDA approved TKIs for use in the treatment of non-small lung cancer (NSCLC) and HER2 overexpressing metastatic breast cancer, respectively.

However, despite the clinical usefulness of monoclonal antibody therapy and TKIs, development of acquired resistance to the treatment is an increasing issue. Combination therapy of mAbs and conventional cytotoxic chemotherapy is one of the approaches being carried out in order to increase treatment efficacy. Furthermore, several strategies are being explored to increase the efficacy of monoclonal antibodies, including enhancement of effector functions, and direct and indirect arming of the antibodies with radionuclides or toxins.

Thus, a need exists for additional drugs to treat EGFR family-related diseases in patients, including patients who have developed resistance to existing treatments. These additional drugs also should have a low risk of provoking an undesirable immune response when used to treat human patients.

SUMMARY OF THE INVENTION

We have discovered that simultaneous targeting of two or more members of the EGFR-family (e.g., EGFR, HER2, and HER3) with humanized antibodies leads to effective inhibition of cancer growth. We have also discovered that compositions targeting multiple EGFR-family members can be used to treat cancer, such as pancreatic, bone, colon, endometrial, or urinary tract cancer, including cancer that has acquired resistance to drug therapies targeting only one EGFR-family member.

Accordingly, the present invention is directed to humanized antibodies directed against EGFR, HER2 and HER3, as well as compositions comprising two or more humanized antibodies directed against two or more of these targets. The invention is further directed to the use of the antibodies and compositions for human cancer therapy.

One aspect of the invention relates to a recombinant antibody composition comprising at least one humanized anti-EGFR antibody or an antigen-binding fragment thereof, at least one humanized anti-HER2 antibody or an antigen-binding fragment thereof, and at least one humanized anti-HER3 antibody or an antigen-binding fragment thereof.

A humanized anti-EGFR antibody of the invention may be selected from an antibody comprising the heavy chain variable region sequence of SEQ ID NO:1 and the light chain variable region sequence of SEQ ID NO:3 or SEQ ID NO:2, and an antibody comprising the heavy chain variable region sequence of SEQ ID NO:4 and the light chain variable region sequence of SEQ ID NO:5. In one embodiment, the anti-EGFR antibody may comprise a heavy chain variable region sequence (SEQ ID NO:1) comprising Arg44 and Val83, and a light chain variable region sequence (SEQ ID NO:2) comprising Ala19 and Phe92; a heavy chain variable region sequence (SEQ ID NO:1) comprising Arg44, Val83 and Ile104, and a light chain variable region sequence (SEQ ID NO:3) comprising Tyr41, Leu51 and Phe92; or a heavy chain variable region sequence (SEQ ID NO:1) comprising Arg44, Val83 and Ile104, and a light chain variable region sequence (SEQ ID NO:3) comprising Leu34, Tyr41, Leu51 and Phe92. In another embodiment, the anti-EGFR antibody may comprise a heavy chain variable region sequence (SEQ ID NO:4) comprising Leu20, Ile48 and Ala68, and a light chain variable region sequence (SEQ ID NO:5) comprising Val75 and Phe87; or a heavy chain variable region sequence (SEQ ID NO:4) comprising Leu20, Ile48, Leu56, and Ala68, and a light chain variable region sequence (SEQ ID NO:5) comprising Val75 and Phe87.

In some embodiments, the invention encompasses a humanized anti-EGFR antibody whose heavy and light chain amino acid sequences comprise: SEQ ID NOs:42 and 43, respectively, SEQ ID NOs:38 and 39, respectively, SEQ ID NOs:40 and 41, respectively, SEQ ID NOs:44 and 45, respectively, or SEQ ID NOs:46 and 47, respectively, or an antigen-binding fragment thereof.

A humanized anti-HER2 antibody of the invention may be selected from an antibody comprising the heavy chain variable region sequence of SEQ ID NO:6 and the light chain variable region sequence of SEQ ID NO:7, and an antibody comprising the heavy chain variable region sequence of SEQ ID NO:8 and the light chain variable region sequence of SEQ ID NO:9. In one embodiment, the anti-HER2 antibody may comprise a heavy chain variable region sequence (SEQ ID NO:6) comprising Ser55, Leu70, Val72, Lys74 and Ala79, and a light chain variable region sequence (SEQ ID NO:7) comprising Val44, Met48 and Tyr70; or a heavy chain variable region sequence (SEQ ID NO:6) comprising Ser55 and Val72, and a light chain variable region sequence (SEQ ID NO:7) comprising Met48 and Tyr70. In another embodiment, the anti-HER2 antibody may comprise a heavy chain variable region sequence (SEQ ID NO:8) comprising Ala49, Ile74 and Ser77, and a light chain variable region sequence (SEQ ID NO:9) comprising Thr56, Tyr71, Ser85 and Leu104.

In some embodiments, the invention encompasses a humanized anti-HER2 antibody whose heavy and light chain amino acid sequences comprise: SEQ ID NOs:50 and 51, respectively, SEQ ID NOs:48 and 49, respectively, or SEQ ID NOs:52 and 53, respectively, or an antigen-binding fragment thereof.

A humanized anti-HER3 antibody of the invention may be selected from an antibody comprising the heavy chain variable region sequence of SEQ ID NO:10 and the light chain variable region sequence of SEQ ID NO:11, and an antibody comprising the heavy chain variable region sequence of SEQ ID NO:12 and the light chain variable region sequence of SEQ ID NO:13. In one embodiment, the anti-HER3 antibody may comprise a heavy chain variable region sequence (SEQ ID NO:10) comprising Met49, Ser55 and Ile68, or Asn44, Ser55 and Thr93, and a light chain variable region sequence (SEQ ID NO:11) comprising Phe36, Val44, Phe49 and Ile85, or Phe36, Phe49 and Leu73. In another embodiment, the anti-HER3 antibody may comprise a heavy chain variable region sequence (SEQ ID NO:12) comprising Val46, Met49, Ser55 and Arg72, and a light chain variable region sequence (SEQ ID NO:13) comprising Val21, Val44 and Phe87, and optionally Thr29; or a heavy chain variable region sequence (SEQ ID NO:12) comprising Phe41, Val46, Met49, Ser55 and Arg72, and a light chain variable region sequence (SEQ ID NO:13) comprising Val21, Val44, Tyr71, Phe87 and Leu104.

In some embodiments, the invention encompasses a humanized anti-HER3 antibody whose heavy and light chain amino acid sequences comprise: SEQ ID NOs:54 and 55, respectively, SEQ ID NOs:56 and 57, respectively, SEQ ID NOs:58 and 59, respectively, or SEQ ID NOs:60 and 61, respectively, or an antigen-binding fragment thereof.

The invention also encompasses antibody compositions comprising two, three, four, five or six of the antibodies described above. In some embodiments, the antibody composition may comprise (i) 11294 and/or 11302; (ii) 11249 and/or 11145; and (iii) 10738 and/or 11052. In one embodiment, the composition comprises all six antibodies.

The antibody composition may comprise (a) anti-EGFR antibody 10292, 10460, or 11294; (b) anti-EGFR antibody 10560 or 11302; (c) anti-HER2 antibody 10704 or 11249; (d) anti-HER2 antibody 11145; (e) anti-HER3 antibody 10738 or 10810; and (f) anti-F-HER3 antibody 11006 or 11052. In a preferred embodiment, the antibody composition comprises anti-EGFR antibodies 11294 and 11302, anti-HER2 antibodies 11249 and 11145, and anti-HER3 antibodies 10738 and 11052. Antibody 10292, 10460, 11294, 10560, 11302, 10704, 11249, 11145, 10738, 10810, 11006, or 11052 may comprise at least one additional substitution in any of the heavy chain and/or light chain amino acid residues indicated as "Xaa" in Table 4.

In one embodiment, the antibody composition may comprise (a) an antibody comprising the heavy chain variable region sequence of SEQ ID NO:42 and the light chain variable region sequence of SEQ ID NO:43; (b) an antibody comprising the heavy chain variable region sequence of SEQ ID NO:46 and the light chain variable region sequence of SEQ ID NO:47; (c) an antibody comprising the heavy chain variable region sequence of SEQ ID NO:50 and the light chain variable region sequence of SEQ ID NO:51; (d) an antibody comprising the heavy chain variable region sequence of SEQ ID NO:52 and the light chain variable region sequence of SEQ ID NO:53; (e) an antibody comprising the heavy chain variable region sequence of SEQ ID NO:54 and the light chain variable region sequence of SEQ ID NO:55; and (f) an antibody comprising the heavy chain variable region sequence of SEQ ID NO:60 and the light chain variable region sequence of SEQ ID NO:61.

Further aspects of the invention relate to a method for producing antibodies and antibody compositions of the invention; a pharmaceutical composition comprising an antibody or an antibody composition of the invention and a pharmaceutically acceptable diluent, carrier, or excipient; a method for treating cancer in a human or other mammal comprising administering to a subject in need thereof a therapeutically effective amount of a recombinant antibody composition or pharmaceutical composition of the invention; use of a recombinant antibody composition or a pharmaceutical composition of the invention for preparing a medicament for the treatment of cancer; and a recombinant antibody composition or pharmaceutical of the invention for use as a medicament for treatment of cancer. For human treatment, the antibodies preferably are directed to human HER family members. In some embodiments, each of these compositions comprises more than one monoclonal antibody, each binding to a different epitope in the targeted HER. In some embodiments, at least one of the antibodies is conjugated to an anti-cancer agent, e.g., a cytotoxic agent, a cytokine, a toxin, or a radionuclide.

Cancer treatable by the methods of the invention includes, without limitation, pancreatic cancer (including pancreatic cancer facilitated by a GRAS mutation), head and neck cancer, breast cancer, bone cancer, colon (including colorectal cancer) cancer, endometrial cancer, urinary tract cancer, skin cancer, lung cancer, prostate cancer, gastric cancer, esophageal cancer, ovarian cancer, other epidermal cancer, and cancers with a dependency on one or more of EGFR, HER2, and HER3.

The patient may have been treated for cancer previously. For example, the patient may have been treated with a drug targeting a single EGFR-family member and have acquired resistance to the drug (e.g., cetuximab, trastuzumab, or pertuzumab).

The invention also relates to a nucleic acid molecule comprising a nucleotide sequence encoding any of the antibody heavy or light chains or heavy or light variable regions described herein. The invention also relates to an expression vector comprising such nucleic acid molecules and a host cell comprising such nucleic acid molecules or vectors. The host cell may be capable of expressing any of the antibodies described herein.

BRIEF DESCRIPTION OF THE DRAWINGS

FIG. 1: Amino add sequence alignment of variable chains of the anti-EGFR humanized monoclonal antibodies 10292, 10460, and 11294 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chains of 10292 (SEQ ID NO:38), 10460 (SEQ ID NO:40), and 11294 (SEQ ID NO:42) aligned to CDR grafted sequence (1277_CDRgrafted-H; SEQ ID NO:62). Middle: Variable light chain of 10292 (SEQ ID NO:39) aligned to CDR grafted sequence (1277_CDRgrafted-L; SEQ ID NO:63). Bottom: Variable light chains of 10460 (SEQ ID NO:41) and 11294 (SEQ ID NO:43) aligned to CDR grafted sequence (1277A_CDRgrafted-L; SEQ ID NO:64).

FIG. 2: Amino acid sequence alignment of variable chains of the anti-EGFR humanized monoclonal antibodies 10550 and 11302 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chains of 10560 (SEQ ID NO:44) and 11302 (SEQ ID NO:46) aligned to CDR grafted sequence (1565_CDRgrafted-H; SEQ ID NO:65). Bottom: Variable light chains of 10550 (SEQ ID NO:45) and 11302 (SEQ ID NO:47) aligned to CDR grafted sequence (1565_CDRgrafted-L; SEQ ID NO:66).

FIG. 3: Amino acid sequence alignment of variable chains of the anti-HER2 humanized monoclonal antibodies 10704 and 11249 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chains of 10704 (SEQ ID NO:48) and 11249 (SEQ ID NO:50) aligned to CDR grafted sequence (4384_CDRgrafted-H; SEQ ID NO:67). Bottom: Variable light chains of 10704 (SEQ ID NO:49) and 11249 (SEQ ID NO:51) aligned to CDR grafted sequence (4384_CDRgrafted-L; SEQ ID NO:68).

FIG. 4: Amino acid sequence alignment of variable chains of the anti-HER2 humanized monoclonal antibody 11145 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chain of 11145 (SEQ ID NO:52) aligned to CDR grafted sequence (4517_CDRgrafted-H; SEQ ID NO:69). Bottom: Variable light chain of 11145 (SEQ ID NO:53) aligned to CDR grafted sequence (4517_CDRgrafted-L; SEQ ID NO:70).

FIG. 5: Amino acid sequence alignment of variable chains of the anti-HER3 humanized monoclonal antibodies 10738 and 10810 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chains of 10738 (SEQ ID NO:54) and 10810 (SEQ ID NO:56) aligned to CDR grafted sequence (5038_CDRgrafted-H; SEQ ID NO:71). Bottom: Variable light chains of 10738 (SEQ ID NO:55) and 10810 (SEQ ID NO:57) aligned to CDR grafted sequence (5038_CDRgrafted-L; SEQ ID NO:72).

FIG. 6: Amino acid sequence alignment of variable chains of the anti-HER3 humanized monoclonal antibodies 11006 and 11052 with the in silico designed sequence made up of original murine CDRs grafted into fully human framework regions. Dots denote identity, whereas differing positions are marked with their one letter amino acid abbreviation. Shaded areas indicate CDRs as defined by IMGT. Top: Variable heavy chains of 11006 (SEQ ID NO:58) and 11052 (SEQ ID NO:60) aligned to CDR grafted sequence (5082_CDRgrafted-H; SEQ ID NO:73). Bottom: Variable light chains of 11006 (SEQ ID NO:59) and 11052 (SEQ ID NO:61) aligned to CDR grafted sequence (5082_CDRgrafted-L; SEQ ID NO:74).

FIG. 7: In vitro activity of humanized anti-EGFR antibody variant 10292 in combination with its chimeric anti-EGFR partner antibody. A431N5 cells (top panel) and H358 cells (bottom panel) were treated with different concentrations of the indicated antibody mixtures for 96 hours. Data are presented as means±SEM.

FIG. 8: In vitro activity of humanized anti-EGFR antibody variant 10460 in combination with its chimeric anti-EGFR partner antibody. A431NS cells (top panel) and H358 cells (bottom panel) were treated with different concentrations of the indicated antibody mixtures for 96 hours. Data are presented as means±SEM.

FIG. 9: In vitro activity of humanized anti-EGFR antibody variant 10560 in combination with its chimeric anti-EGFR partner antibody. A431NS cells (top panel) and H358 cells (bottom panel) were treated with different concentrations of the indicated antibody mixtures for 95 hours. Data are presented as means±SEM.

FIG. 10: In vitro activity of humanized anti-HER2 antibody variant 10704 in combination with its chimeric anti-HER2 partner antibody. OE19 cells (top panel) and BT474 cells (bottom panel) were treated with different concentrations of the indicated antibody mixtures for 96 hours. Data are presented as means±SEM.

FIG. 11: In vitro activity of humanized anti-HER2 antibody variant 11145 in combination with its chimeric anti-HER2 partner antibody. OE19 cells (top panel) and BT474 cells (bottom panel) were treated with different concentrations of the indicated antibody mixtures for 96 hours. Data are presented as means±SEM.

FIG. 12: In vitro activity of humanized anti-HER3 antibody variant 10738 in combination with its chimeric anti-HER3 partner antibody. MBA-MD-175 VII cells (top panel) and MCF-7 cells (in the presence of 1 nM heregulin beta; bottom panel) were treated with different concentrations of the indicated antibody mixtures for 96 hours. Data are presented as means±SEM.

FIG. 13: In vitro activity of humanized anti-HER3 antibody variant 10810 in combination with its chimeric anti-HER3 partner antibody. MBA-MD-175 VII cells (top panel) and MCF-7 cells (in the presence of 1 nM heregulin beta; bottom panel) were treated with different concentrations of the indicated antibody mixtures for 96 hours. Data are presented as means±SEM.

FIG. 14: In vitro activity of humanized anti-HER3 antibody variant 11006 in combination with its chimeric anti-HER3 partner antibody. MBA-MD-175 VII cells (top panel) and MCF-7 cells (in the presence of 1 nM heregulin beta; bottom panel) were treated with different concentrations of the indicated antibody mixtures for 96 hours. Data are presented as means±SEM.

FIG. 15: In vitro activity of humanized anti-HER3 antibody variant 11052 in combination with its chimeric anti-HER3 partner antibody. MBA-MD-175 VII cells (top panel) and MCF-7 cells (in the presence of 1 nM heregulin beta; bottom panel) were treated with different concentrations of the indicated antibody mixtures for 96 hours. Data are presented as means±SEM.

FIG. 16: Cross-reactivity pattern of chimeric and humanized antibodies with human, cynomolgus and murine HER family antigens. The OD signal from 40 nM antibody, measured at 450 nm using an ELISA reader, was scored from negative (−OD<0.1) to strongly positive (+++; OD>2.5).

FIG. 17: In vitro activity of humanized anti-EGFR antibody variant 11294 in combination with its chimeric anti-EGFR partner antibody. A431NS cells (top panel) and FaDu cells (bottom panel) were treated with different concentrations of the indicated antibody mixtures for 96 hours. Data are presented as means±SEM.

FIG. 18: In vitro activity of humanized anti-EGFR antibody variant 11302 in combination with its chimeric anti-EGFR partner antibody. A431NS cells (top panel) and FaDu cells (bottom panel) were treated with different concentrations of the indicated antibody mixtures for 96 hours. Data are presented as means±SEM.

FIG. 19: In vitro activity of humanized anti-HER2 antibody variant 11249 in combination with its humanized anti-HER2 partner antibody 11145. OE19 cells (top panel) and BT474 cells (bottom panel) were treated with different concentrations of the indicated antibody mixtures for 96 hours. Data are presented as means±SEM.

FIG. 23 is a table showing maximal metabolic activity as a percentage of untreated (no Heregulin or EGF) control cells (set to 100%) after treatment with Pan-HER mixture (1277, 1565, 4384, 4517, 5038 and 5082; chimeric Pan-HER), Pan-HER subcomponents and a negative control antibody.

FIG. 24 is a table showing maximal metabolic activity as a percentage of untreated control cells in the absence of ligand (set to 100%) after treatment with Pan-HER (1277, 1565, 4384, 4517, 5038 and 5082; chimeric Pan-HER), Pan-HER subcomponents and a negative control antibody in the presence of 5 nM Heregulin. Cells were exposed to medium containing antibodies and ligands for 96 hours. (i.e. ligand and antibody was added simultaneously to the cells).

FIG. 25 is a table showing maximal metabolic activity as a percentage of untreated control cells in the absence of ligand (set to 100%) after treatment with Pan-HER (1277, 1565, 4384, 4517, 5038 and 5082; chimeric Pan-HER), Pan-HER subcomponents and a negative control antibody in the presence of 1 nM EGF. Cells were exposed to medium containing antibodies and ligands for 96 hours. (i.e. ligand and antibody was added simultaneously to the cells).

DETAILED DESCRIPTION OF THE INVENTION

Figure 20:
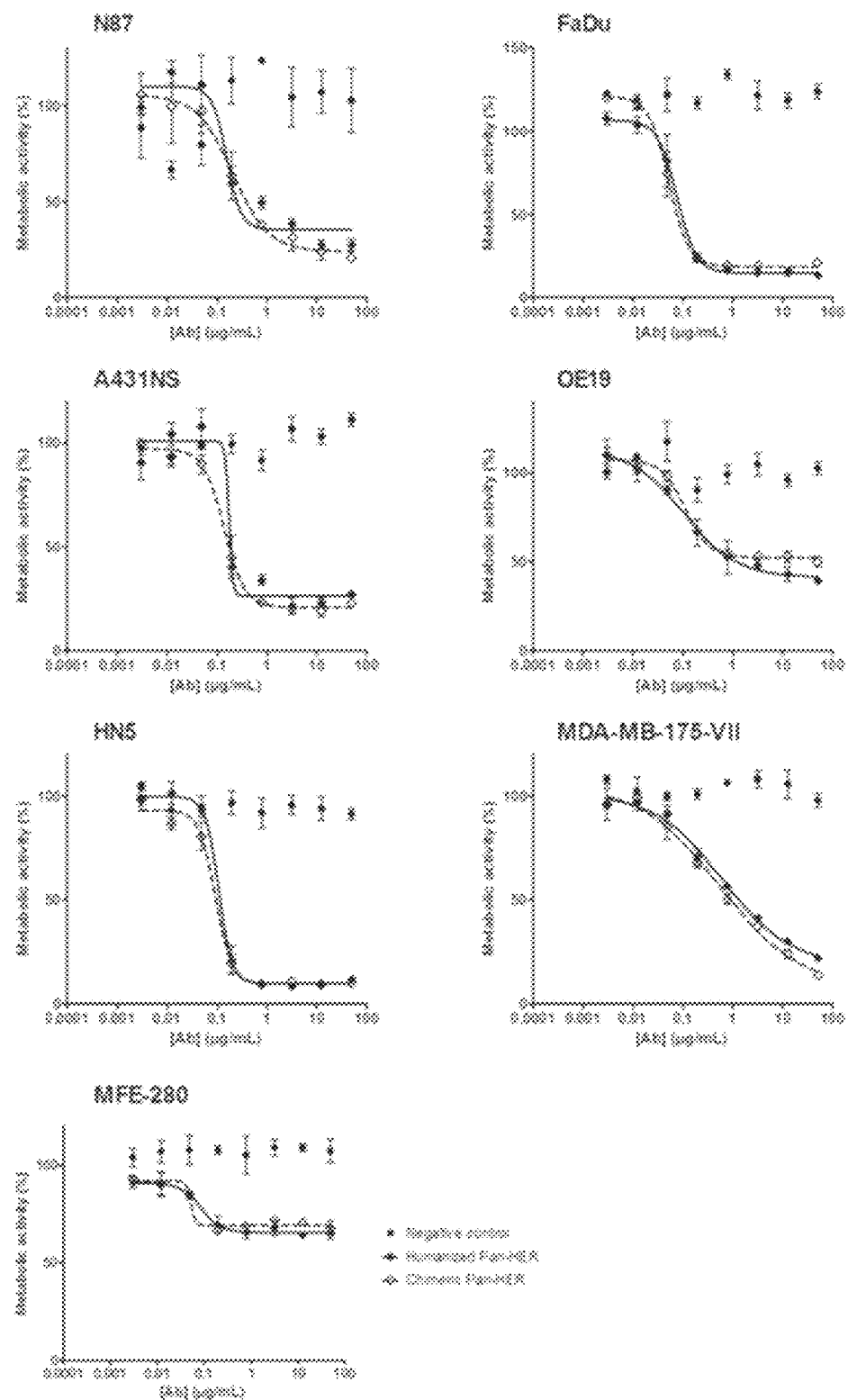
FIG. 20: In vitro activity of a mixture of humanized antibodies (variants 11294, 11302, 11249, 11145, 10738 and 11052; humanized Pan-HER) and a mixture of chimeric antibodies (1277, 1565, 4384, 4517, 5038 and 5082; chimeric Pan-HER). The indicated cell lines were treated with different concentrations of the indicated antibody mixtures for 96 hours. Data are presented as means±SEM.

While some monoclonal antibodies (e.g., cetuximab, trastuzumab, and pertuzumab) have been used to treat EGFR-family-related diseases, these treatments are not effective for all patients. Additionally, patients often develop resistance to such drugs after initial use. This invention is based on our discovery of new humanized antibodies targeting EGFR-family members EGFR, HER2, and HER3 and that mixtures of such humanized antibodies (a humanized pan-HER antibody composition) can effectively down-regulate the targets and inhibit growth of a variety of cancer cell lines. We have also discovered that antibody mixtures targeting EGFR-family members EGFR, HER2, and HER3 effectively suppress tumor growth in multiple xenograft models of human cancer, including hard-to-treat patient-derived models of pancreatic cancer. We have also shown that antibody mixtures targeting more than one EGFR-family member retain their inhibitory effect in cells that have acquired resistance to therapeutic monoclonal antibodies such as cetuximab, trastuzumab, and pertuzumab.

Humanized Antibodies

One aspect of the invention relates to humanized antibodies that bind the EGFR-family members EGFR, HER2, and HER3. The term "antibody" or "antibody molecule" describes a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins.

Unless otherwise indicated, the terms "antibody" or "antibodies" as used herein are intended to include single chain antibodies as well as binding fragments of antibodies, such as Fab, F(ab')2, Fv fragments or single chain Fv (scFv) fragments, and multimeric forms such as dimeric IgA molecules or pentavalent IgM. In the present description and claims, references to an "antibody" or "antibodies" are therefore intended to encompass, in particular, binding fragments and single chain antibodies, unless it is indicated otherwise or apparent from the context that this is not the case.

Each heavy chain of an antibody typically includes a heavy chain variable region (VH) and a heavy chain constant region. The heavy chain constant region typically includes three domains, referred to as CH1, CH2 and CH3. Each antibody light chain typically includes a light chain variable region (VL) and a light chain constant region. The light chain constant region typically includes a single domain, referred to as CL. The VH and VL regions may be further subdivided into regions of hypervariability ("hypervariable regions", which may be hypervariable in sequence and/or in structurally defined loops). The "hypervariable" regions found in the variable domains of an antibody that are primarily responsible for determining the antibody's binding specificity. These are also referred to as complementarity determining regions (CDRs), which are interspersed with regions that are more conserved, termed framework regions (FRs). Each of the heavy and light chains of an antibody contains three CDR regions, referred to as CDR1, CDR2 and CDR3, of which CDR3 shows the greatest variability. Each VH and VL typically includes three CDRs and four FRs, arranged from the amino terminus to the carboxy terminus in the following order: FR1, CDR1, FR2, CDR2, FR3, CDR3, FR4. The amino acid residues in the variable regions are often numbered using a standardized numbering method known as the Kabat numbering scheme (Kabat et al, (1991) Sequences of Proteins of Immunological Interest, 5th Ed, Public Health Service, National Institutes of Health, Bethesda, Md., USA), although other numbering schemes such as Chothia and IMGT also exist.

The term "recombinant antibody" refers to an antibody that is expressed from a cell or cell line transfected with an expression vector (or possibly more than one expression vector, e.g. two expression vectors) comprising the coding sequence of the antibody, where said coding sequence is not naturally associated with the cell.

The four-digit antibody numbers used herein, i.e. 1277, 1565, 4384, 4517, 5038 and 5082, refer to the chimeric parent antibodies disclosed in WO 2012/059857, from which the humanized antibodies of the invention are derived. Table 1 below shows the SEQ ID NOs, as set forth in Table 8, for the DNA and amino acid sequences of the heavy chain variable regions (VH) and the light chains (LC) of antibodies 1277, 1555, 4384, 4517, 5038, and 5082.

TABLE 1

SEQ ID NOs for the DNA and amino acid sequences of the heavy chain variable regions and light chains of chimeric antibodies

| Antibody Number | Antigen | $V_H$ DNA seq. | $V_H$ amino acid seq. | light chain DNA seq. | light chain amino acid seq. |
|---|---|---|---|---|---|
| 1277 | EGFR | 14 | 15 | 16 | 17 |
| 1565 | EGFR | 18 | 19 | 20 | 21 |
| 4384 | HER2 | 22 | 23 | 24 | 25 |
| 4517 | HER2 | 26 | 27 | 28 | 29 |
| 5038 | HER3 | 30 | 31 | 32 | 33 |
| 5082 | HER3 | 34 | 35 | 36 | 37 |

The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, by constructing expression vectors that express CDR sequences from the specific antibody grafted into framework sequences from a different antibody. As a result, it is possible to "humanize" a non-human antibody and still substantially maintain the binding specificity and affinity of the original antibody. A more detailed discussion of humanization is provided below.

A "chimeric antibody" refers in its broadest sense to an antibody that contains one or more regions from one antibody and one or more regions from one or more other antibodies, typically an antibody that is partially of human origin and partially of non-human origin, i.e. derived in part from a non-human animal, for example a mouse, rat or other rodent, or an avian such as a chicken. Chimeric antibodies are preferred over non-human antibodies in order to reduce the risk of a human anti-antibody response, e.g. a human anti-mouse antibody response in the case of a murine antibody. An example of a typical chimeric antibody is one in which the variable region sequences are murine sequences derived from immunization of a mouse, while the constant region sequences are human. In the case of a chimeric antibody, the non-human parts may be subjected to further alteration in order to humanize the antibody. As described elsewhere herein, the present invention is based on humanization of certain chimeric antibodies having murine variable region sequences.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans. It is known that all antibodies have the potential for eliciting a human anti-antibody response, which correlates to some extent with the degree of "humanness" of the antibody in question. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies. For chimeric antibodies or other antibodies of non-human origin, it is therefore preferred that they be humanized to reduce the risk of a human anti-antibody response.

For chimeric antibodies, humanization typically involves modification of the framework regions of the variable region sequences. Amino acid residues that are part of a complementarity determining regions (CDRs) will most often not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see e.g. the review by Almagro & Fransson (2008) *Front Biosci.* 13: 1619-1633. One commonly used method is CDR grafting, which for e.g. a murine-derived chimeric antibody involves identification of human germline gene counterparts to the murine variable region genes and grafting of the murine CDR sequences into this framework. CDR grafting may be based on the Kabat CDR definitions, although a more recent publication (Magdelaine-Beuzelin et al. (2007) *Crit Rev. Oncol Hematol.* 64: 210-225) has suggested that the IMGT® definition (the international ImmunoGeneTics information System®, www.imgt.org) may improve the result of the humanization (see Lefranc et al. (2003), IMGT unique numbering for immunoglobulin and T cell receptor variable domains and Ig superfamily V-like domains, *Dev. Comp Immunol.* 27, 55-77). Since CDR grafting may reduce the binding specificity and affinity, and thus the biological activity, of a CDR-grafted non-human antibody, back mutations (some-times referred to as "framework repair") may be introduced at selected positions of the CDR-grafted antibody, typically in the framework regions, in order to reestablish the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al. (1997) *PNAS USA, vol.* 94, pp. 412-417 and the stepwise in vitro affinity maturation method of Wu et al. (1998) *PNAS USA, vol.* 95, pp. 6037-6042.

Amino acid residues herein may be indicated by either the one-letter code or the three-letter code. Amino acid substitutions relative to a reference sequence may e.g. be indicated using the format "G44R", which indicates that a glycine residue in position 44 of a reference sequence has been mutated to an arginine residue. For example, in Table 3 below, "G44R" indicates a mutation of the glycine residue in a CDR-grafted antibody to an arginine residue. An amino acid residue written in the format "Arg44" indicates a particular residue in a particular position, i.e. in this case an arginine residue in position 41. Unless otherwise indicated, numbering of amino acid residues refers to the appended sequence listing.

As noted above, the present invention relates to humanized antibodies, more particularly to humanized antibodies based on certain chimeric parent antibodies described in WO 2012/059857. The humanized antibodies of the invention were developed using CDR grafting and back mutations, and in some cases alteration of unwanted sequence motifs, starting with selected chimeric anti-EGFR, anti-HER2 and anti-HER3 antibodies described in WO 2012/059857. The particular methods used to develop these humanized antibodies, as well as the results of functional evaluation of the humanized antibodies compared to the original chimeric antibodies from which they were developed, are described in the examples below. Strikingly, the data presented in the examples shows that mixtures containing a humanized antibody of the invention have an in vitro efficacy that is comparable to that of corresponding mixtures of the original chimeric antibodies, demonstrating that the humanization process did not affect the inhibitory properties of these antibodies or their ability to function in combination with each other. The data also strongly suggests that the humanized antibody mixtures will also show an in vivo efficacy that is comparable to that of the original chimeric antibody mixtures described in WO 2012/059857.

The five-digit antibody numbers used herein, e.g. "antibody 10560", refer to the specific humanized antibodies described below, which have been prepared by CDR grafting based on a chimeric parent antibody. For example, antibody 10560 is an antibody with a heavy chain comprising the heavy chain variable region sequence (VH) set forth in SEQ ID NO:4 and a light chain comprising the light chain variable region sequence (VL) set forth in SEQ ID NO:5, and comprising substitutions (for example, back mutations) at certain positions compared to the original CDR-grafted antibody (see Table 3 and FIGS. 1-6). In the examples below, the antibodies also included a human kappa constant region sequence (SEQ ID NO:42 in WO 2012/059858 and U.S. Pat. No. 8,609,095, with an N-terminal Arg residue) and a human IGHG1 heavy chain constant region sequence (SEQ ID NO:44 in WO 2012/059858 and U.S. Pat. No. 8,609,095).

Particular humanized antibodies of the invention are described herein by way of an antibody number, i.e. 10292, 10460, 11294, 10560, 10704, 11302, 11145, 11249, 10738, 10810, 11006 or 11052. These are derived from the chimeric antibodies (murine variable regions, human constant regions) disclosed in WO 2012/059857 by CDR grafting and subsequent mutation at certain positions, primarily back mutations, as described in Example 1. Table 2 below outlines how the humanized antibodies of the invention are related to the chimeric parent antibodies disclosed in WO 2012/059857.

TABLE 2

Humanized and chimeric parent antibody numbers

| Humanized antibody | Chimeric parent antibody |
|---|---|
| 10292 | 1277 |
| 10460 | 1277 |
| 11294 | 1277 |
| 10560 | 1565 |
| 11302 | 1565 |
| 10704 | 4384 |
| 11249 | 4384 |
| 11145 | 4517 |
| 10738 | 5038 |
| 10810 | 5038 |
| 11006 | 5082 |
| 11052 | 5082 |

Table 3 below provides the SEQ ID NOs of exemplary humanized antibodies of the invention, as well as the individual substitutions (back mutations, and in certain cases mutation(s) to alter undesired sequence motifs) in the heavy chain (HC) and light chain (LC) compared to the original CDR-grafted antibody. The amino acid sequences of the heavy and light chains of the antibodies listed in Table 3 are provided in FIGS. 1-6 and in separate SEQ ID NOs enclosed in parentheses in Table 3. The CDR sequences in FIGS. 1-6 are indicated with shading.

TABLE 3

Sequence numbers and substitutions in selected humanized antibodies

| Humanized Ab number | HC + LC SEQ ID NO. and substitutions |
|---|---|
| 10292 | HC: SEQ ID NO: 1; G44R, M83V (SEQ ID NO: 38) |
|  | LC: SEQ ID NO: 2; V19A, Y92F (SEQ ID NO: 39) |
| 10460 | HC: SEQ ID NO: 1; G44R, M83V, M104I (SEQ ID NO: 40) |
|  | LC: SEQ ID NO: 3; F41Y, F51L, Y92F (SEQ ID NO: 41) |

TABLE 3-continued

Sequence numbers and substitutions in selected humanized antibodies

| Humanized Ab number | HC + LC SEQ ID NO. and substitutions |
|---|---|
| 11294 | HC: SEQ ID NO: 1; G44R, M83V, M104I (SEQ ID NO: 42) |
| | LC: SEQ ID NO: 3; G34L, F41Y, F51L, Y92F (SEQ ID NO: 43) |
| 10560 | HC: SEQ ID NO: 4; V20L, M48I, V68A (SEQ ID NO: 44) |
| | LC: SEQ ID NO: 5; I75V, Y87F (SEQ ID NO: 45) |
| 11302 | HC: SEQ ID NO: 4; V20L, M48I, G56L, V68A (SEQ ID NO: 46) |
| | LC: SEQ ID NO: 5; I75V, Y87F (SEQ ID NO: 47) |
| 10704 | HC: SEQ ID NO: 6; N55S, M70L, R72V, T74K, V79A (SEQ ID NO: 48) |
| | LC: SEQ ID NO: 7; P44V, I48M, F70Y (SEQ ID NO: 49) |
| 11249 | HC: SEQ ID NO: 6; N55S, R72V (SEQ ID NO: 50) |
| | LC: SEQ ID NO: 7; I48M, F70Y (SEQ ID NO: 51) |
| 11145 | HC: SEQ ID NO: 8; S49A, N74I, N77S (SEQ ID NO: 52) |
| | LC: SEQ ID NO: 9; D56T, F71Y, Y85S, V104L (SEQ ID NO: 53) |
| 10738 | HC: SEQ ID NO: 10; I49M, D55S, V68I (SEQ ID NO: 54) |
| | LC: SEQ ID NO: 11; Y36F, P44V, Y49F, T85I (SEQ ID NO: 55) |
| 10810 | HC: SEQ ID NO: 10; K44N, D55S, V93T (SEQ ID NO: 56) |
| | LC: SEQ ID NO: 11; Y36F, Y49F, F73L (SEQ ID NO: 57) |
| 11006 | HC: SEQ ID NO: 12; L46V, I49M, D55S, V72R (SEQ ID NO: 58) |
| | LC: SEQ ID NO: 13; I21V, I29T, P44V, Y87F (SEQ ID NO: 59) |
| 11052 | HC: SEQ ID NO: 12; H41F, L46V, I49M, D55S, V72R (SEQ ID NO: 60) |
| | LC: SEQ ID NO: 13; I21V, P44V, F71Y, Y87F, V104L (SEQ ID NO: 61) |

An indication that any of the numbered humanized antibodies listed in Table 2 may comprise "at least one additional substitution in any of the heavy chain and/or light chain amino acid residues indicated as "Xaa" in Table 4" means that the antibodies may comprise additional substitutions in one or more "Xaa" residues other than the substitutions listed above in Table 3.

TABLE 4

Sequences of selected humanized antibodies

```
SEQ ID NO: 1
<210> 1
<211> 117
<212> PRT
<213> Artificial Sequence
<220>
<223> Humanized 1277 VH
<220>
<221> VARIANT
<222> (44)..(44)
<223> Xaa = Gly or Arg
<220>
<221> VARIANT
<222> (49)..(49)
<223> Xaa = Ser or Ala
<220>
<221> VARIANT
<222> (83)..(83)
<223> Xaa = Met or Val
<220>
<221> VARIANT
<222> (104)..(104)
<223> Xaa = Met or Ile
<400> 1
Glu Val Gln Leu Val Glu Ser Gly Gly Gly Leu Val Gln Pro Gly Trp
1               5                   10                  15
Ser Leu Arg Leu Ser Cys Ala Ala Ser Gly Phe Ala Phe Ser Tyr Ser
                20                  25                  30
Asp Met Ser Trp Val Arg Gln Ala Pro Gly Lys Xaa Leu Glu Trp Val
            35                  40                  45
Xaa Tyr Met Ser Ser Ala dip Asp Val Thr Phe Tyr Ser Asp Thr Val
        50                  55                  60
Lys Gly Arg Phe Thr Ile Ser Arg Asp Asn Ala Lys Asn Ser Leu Tyr
65                  70                  75                  80
Leu Gln Xaa Asn Ser Leu Arg Ala Glu Asp Thr Ala Val Tyr Tyr Cys
                85                  90                  95
Val Arg His Arg Asp Val Ala Xaa Asp Tyr Trp Gly Gln Gly Thr Thr
            100                 105                 110
Val Thr Val Ser Ser
            115

SEQ ID NO: 2
<210> 2
```

TABLE 4 -continued

Sequences of selected humanized antibodies

```
<211> 111
<212> PRT
<213> Artificial Sequence
<220>
<223> Humanized 1277 VL
<220>
<221> VARIANT
<222> (13)..(13)
<223> Xaa = Ala or Val
<220>
<221> VARIANT
<222> (19)..(19)
<223> Xaa = Val or Ala
<220>
<221> VARIANT
<222> (33)..(33)
<223> Xaa can be any naturally occurring amino acid
<220>
<221> VARIANT
<222> (34)..(34)
<223> Xaa can be any naturally occurring amino acid
<220>
<221> VARIANT
<222> (42)..(42)
<223> Xaa = Gln or Leu
<220>
<221> VARIANT
<222> (48)..(18)
<223> Xaa = Ala or 3cr
<220>
<221> VARIANT
<222> (83)..(83)
<223> Xaa = Leu or Val
<220>
<221> VARIANT
<222> (89)..(89)
<223> Xaa = Ala or Gly
<220>
<221> VARIANT
<222> (92)..(92)
<223> Xaa = Tyr or Phe
<220>
<221> VARIANT
<222> (108)..(108)
<223> Xaa = Val or Leu
<400>
Asp Ile Gln Met Thr Gln Ser Pro Ser Ser Leu Ser Xaa Ser Val Gly
1               5                   10                  15
Asp Arg Xaa Thr Ile Thr Cys Arg Ser Ser Gln Ser Leu Val His Ser
            20                  25                  30
Xaa Asn Thr Tyr Leu His Trp Tyr Xaa Gln Lys Pro Gly Lys Xaa
        35                  40                  45
Pro Lys Leu Leu Ile Tyr Lys Val Ser Asn Arg Phe Ser Gly Val Pro
    50                  55                  60
Ser Arg Phe Ser Gly Ser Gly Ser Gly Thr Asp Phe Thr Leu Thr Ile
65                  70                  75                  80
Ser Ser Xaa Gln Pro Glu Asp Phe Xaa Thr Tyr Xaa Cys Ser Gln Ser
                85                  90                  95
Thr His Val Pro Thr Phe Gly Gly Gly Thr Lys Xaa Glu Ile Lys
            100                 105                 110

SEQ ID NO: 3
<210> 3
<211> 111
<212> PRT
<213> Artificial Sequence
<220>
<223> Humanized 1277A VL
<220>
<221> VARIANT
<222> (33)..(33)
<223> Xaa = Asn or Ser
<220>
<221> VARIANT
<222> (34)..(34)
<223> Xaa = Gly or Leu
<220>
<221> VARIANT
```

TABLE 4 -continued

Sequences of selected humanized antibodies

```
<222> (41)..(41)
<223> Xaa = Phe or Tyr
<220>
<221> VARIANT
<277> (42)..(42)
<223> Xaa = Gln or Leu
<220>
<221> VARIANT
<222> (51)..(51)
<223> Xaa = Arg or Leu
<220>
<221> VARIANT
<222> (92)..(92)
<223> Xaa = Tyr or Phe
<220>
<221> VARIANT
<222> (108)..(108)
<223> Xaa = Val or Leu
```

| | | | | | | | | | | | | | | |
|---|---|---|---|---|---|---|---|---|---|---|---|---|---|---|
| Asp | Val | Val | Met | Thr | Gln | Ser | Pro | Leu | Ser | Leu | Pro | Val | Thr | Leu | Gly |
| 1 | | | | 5 | | | | | 10 | | | | | 15 | |
| Gln | Pro | Ala | Ser | Ile | Ser | Cys | Arg | Ser | Ser | Gln | Ser | Leu | Val | His | Ser |
| | | | 20 | | | | | 25 | | | | | 30 | | |
| Xaa | Xaa | Asn | Thr | Tyr | Leu | His | Trp | Xaa | Xaa | Gln | Arg | Pro | Gly | Gln | Ser |
| | | | 35 | | | | 40 | | | | 45 | | | | |
| Pro | Arg | Xaa | Leu | Ile | Tyr | Lys | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Xaa | Cys | Ser | Gln | Ser |
| | | | | 85 | | | | | 90 | | | | | 95 | |
| Thr | His | Val | Pro | Thr | Phe | Gly | Gly | Gly | Thr | Lys | Xaa | Glu | Ile | Lys | |
| | | | 100 | | | | | 105 | | | | | 110 | | |

```
SEQ ID NO: 4
<210> 4
<211> 121
<212> PRT
<213> Artificial Sequence
<220>
<223> Humanized 1565 VH
<220>
<221> VARIANT
<222> (20)..(20)
<223> Xaa = Val or Leu
<220>
<221> VARIANT
<222> (38)..(38)
<223> Xaa = Arg or Lys
<220>
<221> VARIANT
<222> (40)_(10)
<223> Xaa = Ala or Ara
<220>
<221> VARIANT
<222> (48)..(48)
<223> Xaa = Met or Ile
<220>
<221> VARIANT
<222> (55)..(55)
<223> Xaa can be any naturally occurring amino acid
<220>
<221> VARIANT
<222> (56)..(56)
<223> Xaa can be any naturally occurring amino acid
<220>
<221> VARIANT
<222> (68)..(68)
<223> Xaa = Val or Ala
<220>
<221> VARIANT
<222> (70)..(70)
<223> Xaa = Met or Leu
<220>
<221> VARIANT
<222> (72)..(72)
<223> Xaa = Arg or Val
<220>
<221> VARIANT
```

TABLE 4 -continued

Sequences of selected humanized antibodies

```
<222> (74)..(74)
<223> Xaa = Thr or Lys
<220>
<221> VARIANT
<222> (79)..(79)
<223> Xaa = Val or Ala
<400> 4
Gln Val Gln Leu Val Gln Ser Gly Ala Glu Val Lys Lys Pro Gly Ala
1               5                   10                  15
Ser Val Lys Xaa Ser Cys Lys Ala Ser Gly Tyr Thr Phe Thr Ser Tyr
            20                  25                  30
Trp Met Gln Trp Val Xaa Gln Xaa Pro Gly Gln Gly Leu Glu Trp Xaa
        35                  40                  45
Gly Asn Ile Asn Pro Ser Xaa Xaa Gly Thr Ser Phe Asn Glu Glu Phe
    50                  55                  60
Lys Ser Arg Xaa Thr Xaa Thr Xaa Asp Xaa Ser Thr Set Thr Xaa Tyr
65                  70                  73                  80
Met Glu Leu Ser Ser Leu Arg Ser Glu Asp Thr Ala Val Tyr Tyr Cys
                85                  90                  95
Ala Arg Asp Gly Gly Leu Tyr Asp Gly Tyr Tyr Phe Asp Phe Trp Gly
            100                 105                 110
Gln Gly Thr Leu Val Thr Val Ser Ser
        115                 120

SEQ ID NO: 5
<210> 5
<211> 107
<212> PRT
<213> Artificial Sequence
<220>
<223> Humanized 1565 VL
<220>
<221> VARIANT
<222> (4)..(4)
<223> Xaa = Leu or Met
<220>
<221> VARIANT
<222> (75)..(75)
<223> Xaa = Ile or Val
<220>
<221> VARIANT
<222> (87)..(87)
<223> Xaa = Tyr or Phe
<400> 3
Ala Ile Gln Xaa Thr Gln Ser Pro Ser Ser Leu Ser Ala Ser Val Gly
1               5                   10                  15
Asp Arg Val Thr Ile Thr Cys Lys Ala Ser Gln Asp Val Asp Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg HaS Thr Gly Val Pro Ser Arg Phe Ser Glp
    50                  55                  60
Ser Gly Ser Gly Thr Asp Phe Thr Leu Thr Xaa Ser Ser Leu Gln Pro
65                  70                  75                  80
Glu Asp Phe Ala Thr Tyr Xaa Cys Gln Gln Tyr Ser Ser Tyr Pro Leu
                85                  90                  95
Thr Phe Gly Gly Gly Thr Lys Val Glu Ile Lys
            100                 105

SEQ ID NO: 6
<210> 6
<211> 119
<212> PRT
<213> Artificial Sequence
<220>
<223> Humanized 4384 VH
<220>
<221> VARIANT
<222> (38)..(38)
<223> Xaa = Arg or Lys
<220>
<221> VARIANT
<222> (48)..(18)
<223> Xaa = Met or Ile
<220>
<221> VARIANT
<222> (55)..(55)
<223> Xaa = Asn or Ser
```

TABLE 4 -continued

Sequences of selected humanized antibodies

```
<220>
<221> VARIANT
<222> (68)..(68)
<223> Xaa = Val or Ala
<220>
<221> VARIANT
<222> (70)..(70)
<223> Xaa = Met or Leu
<220>
<221> VARIANT
<222> (72)..(72)
<223> Xaa = Arg or Val
<220>
<221> VARIANT
<222> (74)..(74)
<223> Xaa = Thr or Lys
<220>
<221> VARIANT
<222> (79)..(79)
<223> Xaa = Val or Ala
<400> 6
Gln Val Gln Leu Val Gln Ser Gly Ala Gln Val Lys Lys Pro Gly Ala
1               5                   10                  15
Ser Val Lys Val Ser Cys Lys Ala Ser Gly Tyr Thr Phe Thr Ser His
                20                  25                  30
Trp Met His Trp Val Xaa Gln Ala Pro Gly Gln Gly Leu Glu Trp Xaa
            35                  40                  45
Gly Asn Ile Asn Pro Ser Xaa Gly Gly Thr Asn Tyr Asn Gln Lys Phe
        50                  55                  60
Lys Ser Arg Xaa Thr Xaa Thr Xaa Asp Xaa Ser Thr Ser Thr Xaa Tyr
65                  70                  75                  80
Met Gln Leu Ser Ser Leu Arg Ser Glu Asp Thr Ala Val Tyr Tyr Cys
                85                  90                  95
Ala Arg Ala Tyr Tyr Asp Phe Ser Trp Phe Val Tyr Trp Gly Gln Gly
            100                 105                 110
Thr Leu Val Thr Val Ser Ser
            115

SEQ ID NO: 7
<210> 7
<211> 106
<212> PRT
<213> Artificial Sequence
<220>
<223> Humanized 4384 VL
<220>
<221> VARIANT
<222> (44)..(44)
<223> Xaa = Pro or Val
<220>
<221> VARIANT
<222> (48)..(48)
<223> Xaa = Ile or Met
<220>
<221> VARIANT
<277> (70)..(70)
<223> Xaa = Phe or Tyr
<220>
<221> VARIANT
<222> (72)..(72)
<223> Xaa = Phe or Leu
<220>
<221> VARIANT
<222> (86)..(86)
<223> Xaa = Tyr or Phe
<400> 7
Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Asp Ile Ser Asn Tyr
                20                  25                  30
Leu Asn Trp Tyr Gln Gln Lys Pro Gly Lys Ala Xaa Lys Leu Leu Xaa
            35                  40                  45
Tyr Ile Ser Asp Leu His Ser Gly Val Pro Ser Arg Phe Ser Gly Ser
        50                  55                  60
Gly Ser Gly Thr Asp Xaa Thr Xaa Thr Ile Ser Ser Leu Gln Pro Glu
65                  70                  75                  80
Asp Ile Ala Thr Tyr Xaa Cys Gln Gln Gly Asn Thr Leu Pro Leu Thr
                85                  90                  95
```

TABLE 4 -continued

Sequences of selected humanized antibodies

Phe Gly Gly Gly Thr Lys Val Glu Ile Lys
            100                 105

SEQ ID NO: 8
<210> 8
<211> 121
<212> PRT
<213> Artificial Sequence
<220>
<223> Humanized 4517 VH
<220>
<221> VARIANT
<222> (39)..(39)
<223> Xaa = Gln or Leu
<220>
<221> VARIANT
<222> (40)..(40)
<223> Xaa = Ala or Thr
<220>
<221> VARIANT
<222> (44)..(44)
<223> Xaa = Gly or Arg
<220>
<221> VARIANT
<222> (49)..(49)
<223> Xaa = Ser or Ala
<220>
<221> VARIANT
<222> (74)..(74)
<223> Xaa = Asn or Ile
<220>
<221> VARIANT
<222> (77)..(77)
<223> Xaa = Asn or Ser
<400> 8
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Gly Met Ser Trp Val Arg Xaa Pro Gly Lys Xaa Leu Glu Trp Val
            35                  40                  45
Xaa Thr Ile Ser Gly Gly Ser Tyr Thr Tyr Tyr Pro Asp Ser Val
        50                  53                  60
Lys Gly Arg Phe Thr Ile Ser Arg Asp Xaa Ala Lys Xaa Ser Leu Tyr
65                  70                  75                  80
Leu Gln Met Asn Ser Leu Arg Ala Glu Asp Thr Ala Val Tyr Tyr Cys
                85                  90                  95
Ala Arg Lys Gly Asn Tyr Gly Asn Tyr Gly Lys Leu Ala Tyr Trp Gly
            100                 105                 110
Gln Gly Thr Thr Val Thr Val Ser Ser
            115                 120

SEQ ID NO: 9
<210> 9
<211> 107
<212> PRT
<213> Artificial Sequence
<220>
<223> Humanized 4517 VL
<220>
<221> VARIANT
<222> (13)..(13)
<223> Xaa = Ala or Val
<220>
<221> VARIANT
<222> (48)..(48)
<223> Xaa = Ile or Val
<220>
<221> VARIANT
<222> (56)..(56)
<223> Xaa = Asp or Thr
<220>
<221> VARIANT
<222> (71)..(71)
<223> Xaa = Phe or Tyr
<220>
<221> VARIANT
<222> (84)..(84)

TABLE 4 -continued

Sequences of selected humanized antibodies

```
<223> Xaa = Ala or Gly
<220>
<221> VARIANT
<222> (85)..(85)
<223> Xaa = Thr or Ser
<220>
<221> VARIANT
<222> (104)_(104)
<223> Xaa = Val or Leu
<400> 9
Asp Ile Gln Met Thr Gln Ser Pro Ser Ser Leu Ser Xaa Ser Val Gly
1               5                   10                  15
Asp Arg Val Thr Ile Thr Cys Arg Ala Ser Glu Asn Ile Tyr Ser Asn
            20                  25                  80
Leu Ala Trp Tyr Gln Gln Lys Pro Gly Lys Ala Pro Lys Leu Leu Xaa
        35                  40                  45
Tyr Ala Ala Thr Asn Leu Ala Xaa Gly Val Pro Ser Arg Phe Ser Gly
    50                  55                  60
Ser Gly Ser Gly Thr Asp Xaa Thr Leu Thr Ile Ser Ser Leu Gln Pro
65                  70                      75                  80
Glu Asp Phe Xaa Xaa Tyr Tyr Cys Gln His Phe Trp Gly Thr Pro Trp
                85                  90                  95
Thr Phe Gly Gln Gly Thr Lys Xaa Glu Ile Lys
                100                 105

SEQ ID NO: 11
<210> 10
<211> 120
<212> PRT
<213> Artificial Sequence
<220>
<223> Humanized 5038 VH
<220>
<221> VARIANT
<222> (44)..(44)
<223> Xaa = Lys or Asn
<220>
<221> VARIANT
<222> (49)..(49)
<223> Xaa = Ile or Met
<220>
<221> VARIANT
<222> (55)..(55)
<223> Xaa = Asp or Ser
<220>
<221> VARIANT
<222> (68)..(68)
<223> Xaa = Val or Ile
<220>
<221> VARIANT
<222> (72)..(72)
<223> Xaa = Val or Arg
<220>
<221> VARIANT
<222> (93)..(93)
<223> Xaa = Val or Thr
<400> 10
Gln Val Gln Leu Gln Glu Ser Gly Pro Gly Leu Val Lys Pro Ser Gln
1               5                   10                  15
Thr Leu Ser Leu Thr Cys Thr Val Ser Gly Tyr Ser Ile Thr Ser Gly
            20                  25                  30
Phe Tyr Trp Thr Trp Ile Arg Gln His Pro Gly Xaa Gly Leu Gln Trp
        35                  40                  45
Xaa Gly Phe Ile Ser Tyr Xaa Gly Ser Asn Asn Tyr Asn Pro Ser Leu
    50                  55                  60
Lys Asn Arg Xaa Thr Ile Ser Xaa Asp Thr Ser Lys Asn Gln Phe Ser
65                  70                  75                      80
Leu Lys Leu Ser Ser Val Thr Ala Ala Asp Thr Ala Xaa Tyr Tyr Cys
                85                  90                  95
Ala Arg Gly Gly Gly Tyr Tyr Gly Asn Leu Phe Asp Tyr Trp Gly Gln
                100                 105                 110
Gly Thr Leu Val Thr Val Ser Ser
                115                 120

SEQ ID NO: 11
<210> 11
<211> 107
<212> PRT
```

TABLE 4 -continued

Sequences of selected humanized antibodies

```
<213> Artificial Sequence
<220>
<223> Humanized 5038 VL
<220>
<221> VARIANT
<277> (36)..(%)
<223> Xaa = Tyr or Phe
<220>
<221> VARIANT
<222> (44)..(44)
<223> Xaa = Pro or Val
<220>
<221> VARIANT
<222> (49)..(49)
<223> Xaa = Tyr or Phe
<220>
<221> VARIANT
<222> (71)..(71)
<223> Xaa = Phe or Tyr
<220>
<221> VARIANT
<277> (73)..(73)
<223> Xaa = Phe or Leu
<220>
<221> VARIANT
<222> (85)..(85)
<223> Xaa = Thr or Ile
<220>
<221> VARIANT
<222> (87)..(87)
<223> Xaa = Tyr or Phe
<400> 11
Asp Ile Gln Met Thr Gln Ser Pro Ser Ser Leu Ser Ala Ser Val Gly
1               5                   10                  15
Asp Arg Val Thr Ile Thr Cys Arg Pro Set Gln Asp Ile Ser Asn Tyr
                20                  25                  30
Val Asn Trp Xaa Gln Gln Lys Pro Gly Lvs Ala Xaa Lys Leu Leu Ile
            35                  40                  45
Xaa His Thr Ser Arg Leu His Ser Gly Val Pro Ser Arg Phe Ser Gly
        50                  55                  60
Ser Gly Ser Gly Thr Asp Xaa Thr Xaa Thr Ile Ser Ser Leu Gln Pro
65                  70                  75                  80
Glu Asp Ile Ala Xaa Tyr Xaa Cys Gln Gln Gly Ile Thr Leu Pro Trp
                85                  90                  95
Thr Phe Gly Gln Gly Thr Lys Val Gln Ile Lys
            100                 105

SEQ ID NO: 12
<210> 12
<211> 118
<212> PRT
<213> Artificial Sequence
<220>
<223> Humanized 5082 VH
<220>
<221> VARIANT
<222> (41)..(41)
<223> Xaa = His or Phe
<220>
<221> VARIANT
<277> (46)..(46)
<223> Xaa = Leu or Val
<220>
<221> VARIANT
<222> (49)..(49)
<223> Xaa = Ile or Met
<220>
<221> VARIANT
<222> (55)..(55)
<223> Xaa = Asp or Ser
<220>
<221> VARIANT
<222> (68)..(68)
<223> Xaa = Val or Ile
<220>
<221> VARIANT
<222> (72)..(72)
<223> Xaa = Val or Arg
```

TABLE 4 -continued

Sequences of selected humanized antibodies

```
<220>
<221> VARIANT
<222> (86)..(36)
<223> Xaa = Val or Leu
<400> 12
Gln Val Gln Leu Gln Gln Ser Gly Pro Gly Leu Val Lys Pro Ser Gln
1               5                   10                  15
Thr Leu Ser Leu Thr Cys Thr Val Ser Gly Tyr Ser Ile Thr Ser Ala
            20                  25                  30
Tyr Tyr Trp Asn Trp Ile Arg Gln Xaa Pro Gly Lys Gly Xaa Glu Trp
        35                  40                  45
Xaa Gly Tyr Ile Gly Tyr Xaa Gly Arg Asn Thr Tyr Asn Pro Ser Leu
    50                  55                  60
Lys Asn Arg Xaa Thr Ile Ser Xaa Asp Thr Ser Lys Asn Gln Phe Ser
65                  70                  75                  80
Leu Lys Leu Ser Ser Xaa Thr Ala Ala Asp Thr Ala Val Tyr Tyr Cys
                85                  90                  95
Ser Arg Glu Gly Asp Tyr Gly Tyr Ser Asp Tyr frp Gly Gln Gly Thr
            100                 105                 110
Leu Val Thr Val Ser Ser
        115

SEQ ID NO: 13
<210> 13
<211> 107
<212> PRT
<213> Artfiail Sequence
<220>
<223> Humanized 5082 VL
<220>
<221> VARIANT
<222> (21)..(21)
<223> Xaa = Ile or Val
<220>
<221> VARIANT
<222> (29)..(29)
<223> Xaa = Ile or Thr
<220>
<221> VARIANT
<222> (44)..(44)
<223> Xaa = Pro or Val
<220>
<221> VARIANT
<222> (69)..(69)
<223> Xaa = Thr or Ile
<220>
<221> VARIANT
<222> (71)..(71)
<223> Xaa = Phe or Tyr
<220>
<221> VARIANT
<222> (87)..(87)
<223> Xaa = Tyr or Phe
<220>
<221> VARIANT
<222> (104)..(104)
<223> Xaa = Val or Leu
<400> 13
Asp Ile Gln Met Thr Gln Ser Pro Ser Ser Leu Ser Ala Ser Val Gly
1               5                   10                  15
Asp Arg Val Thr Xaa Thr Cys Arg Ala Ser Gln Asp Xaa Asn Asn Tyr
            20                  25                  30
Leu Asn Trp Tyr Gln Gln Lys Pro Gly Lys Ala Xaa Lys Leu Leu Ile
        35                  40                  45
Tyr Tyr Thr Ser Asp Leu Gln Ser Gly Val Pro Ser Asp Phe Ser Gly
    50                  55                  60
Ser Gly Ser Gly Xaa Asp Xaa Thr Leu Thr Ile Ser Ser Leu Gln Pro
65                  70                  75                  80
Glu Asp Phe Ala Thr Tyr Xaa Cys Gln Gln Ser Glu Thr Leu Pro Trp
                85                  90                  95
Thr Phe Gly Gln Gly Thr Lys Xaa Glu Ile Lys
            100                 105
```

Amino acid sequence alignments of the CDR-grafted heavy and light chain variable regions of these humanized antibodies with the respective in silico designed sequence made up of original murine CDRs grafted into fully human framework regions are shown in FIGS. 1-6.

One aspect of the invention relates to particular humanized antibodies targeting EGFR, HER2 or HER3. These individual antibodies include the following:
- (a) a humanized anti-EGFR antibody comprising the heavy chain variable region sequence of SEQ ID NO:1 and the light chain variable region sequence of SEQ ID NO:2 or SEQ ID NO:3;
- (b) a humanized anti-EGFR antibody comprising the heavy chain variable region sequence of SEQ ID NO:4 and the light chain variable region sequence of SEQ ID NO:5;
- (c) a humanized anti-HER2 antibody comprising the heavy chain variable region sequence of SEQ ID NO:6 and the light chain variable region sequence of SEQ ID NO:7;
- (d) a humanized anti-HER2 antibody comprising the heavy chain variable region sequence of SEQ ID NO:8 and the light chain variable region sequence of SEQ ID NO:9;
- (e) a humanized anti-HER3 antibody comprising the heavy chain variable region sequence of SEQ ID NO:10 and the light chain variable region sequence of SEQ ID NO:11; and
- (f) a humanized anti-HER3 antibody comprising the heavy chain variable region sequence of SEQ ID NO:12 and the light chain variable region sequence of SEQ ID NO:13.

The above-outlined humanized antibodies typically include, in both the heavy chain variable region sequence and the light chain variable region sequence, one or more of the possible substitutions (primarily back mutations, but in certain cases also mutation to alter unwanted sequence motifs) set forth in Table 4 and in the examples and accompanying figures. The heavy chain variable region sequence and the light chain variable region sequence will typically each comprise two, three, four or five such substitutions.

Examples of a preferred anti-EGFR antibody (a) are antibodies comprising:
- (i) a heavy chain variable region sequence (SEQ ID NO:1) comprising Arg44 and Val83, and a light chain variable region sequence (SEQ ID NO:2) comprising Ala19 and Phe92 [e.g., antibody 10292];
- (ii) a heavy chain variable region sequence (SEQ ID NO:1) comprising Arg44, Val83 and Ile104, and a light chain variable region sequence (SEQ ID NO:3) comprising Tyr41, Leu51 and Phe92 [e.g., antibody 10460]; or
- (iii) a heavy chain variable region sequence (SEQ ID NO:1) comprising Arg44, Val83 and Ile104, and a light chain variable region sequence (SEQ ID NO:3) comprising Leu34, Tyr41, Leu51 and Phe92 [e.g., antibody 11294].

The anti-EGFR antibody (a) may also be an antibody corresponding to antibody 10292, 10460, or 11294, but comprising at least one additional substitution in any of the heavy chain and/or light chain amino acid residues indicated as "Xaa" in Table 4, e.g. substitution in one, two, three or four of such "Xaa" residues. SEQ ID NO:2 includes Xaa in positions 33-34, since the CDR-grafted sequence has a deamidation site (Asn-Gly) in these positions. Although it is possible to perform substitutions in both positions, it is sufficient to alter only one of the two positions in order to eliminate the deamidation site. The sequence will therefore typically include either Asn in position 33 or Gly in position 34.

An example of a preferred anti-EGFR antibody (b) is one comprising:
- (i) a heavy chain variable region sequence (SEQ ID NO:4) comprising Leu20, Ile48 and Ala68, and a light chain variable region sequence (SEQ ID NO:5) comprising Val75 and Phe87 [e.g., antibody 10560]; or
- (ii) a heavy chain variable region sequence (SEQ ID NO:4) comprising Leu20, Ile48, Leu56, and Ala68, and a light chain variable region sequence (SEQ ID NO:5) comprising Val75 and Phe87 [e.g., antibody 11302].

The anti-EGFR antibody (b) may also be an antibody corresponding to antibody 10560 or 11302, but comprising at least one additional substitution in any of the heavy chain and/or light chain amino acid residues indicated as "Xaa" in Table 4, e.g. substitution in one, two, three or four of such "Xaa" residues. SEQ ID NO:4 includes Xaa in positions 55-56, since the CDR-grafted sequence has a deamidation site (Asn-Gly) in these positions. Although it is possible to perform substitutions in both positions, it is sufficient to alter only one of the positions in order to eliminate the deamidation site. The sequence will therefore typically include either Asn in position 55 or Gly in position 55.

An example of a preferred anti-HER2 antibody (c) is one comprising:
- (i) a heavy chain variable region sequence (SEQ ID NO:6) comprising Ser55, Leu70, Val72, Lys74 and Ala79, and a light chain variable region sequence (SEQ ID NO:7) comprising Val44, Met48 and Tyr70 [e.g., antibody 10704]; or
- (ii) a heavy chain variable region sequence (SEQ ID NO:6) comprising Ser55 and Val72, and a light chain variable region sequence (SEQ ID NO:7) comprising Met48 and Tyr70 [e.g., antibody 11249].

The anti-HER2 antibody (c) may also be an antibody corresponding to antibody 10704 or 11249, but comprising at least one additional substitution in any of the heavy chain and/or light chain amino acid residues indicated as "Xaa" in Table 4, e.g. substitution in one, two, three or four of such "Xaa" residues.

An example of a preferred anti-HER2 antibody (d) is one comprising a heavy chain variable region sequence (SEQ ID NO:8) comprising Ala49, Ile74 and Ser77, and a light chain variable region sequence (SEQ ID NO:9) comprising Thr56, Tyr71, Ser85 and Leu104 [e.g., antibody 11145]. The anti-HER2 antibody (d) may also be an antibody corresponding to antibody 11145, but comprising at least one additional substitution in any of the heavy chain and/or light chain amino acid residues indicated as "Xaa" in Table 4, e.g. substitution in one, two, three or four of such "Xaa" residues.

Examples of a preferred anti-HER3 antibody (e) are antibodies comprising a heavy chain variable region sequence (SEQ ID NO:10) comprising Met49, Ser55 and Ile68, or comprising Asn44, Ser55 and Thr93, and a light chain variable region sequence (SEQ ID NO:11) comprising Phe36, Val44, Phe49 and Ile85, or comprising Phe36, Phe49 and Leu73. Particular examples of such anti-HER3 antibodies are those comprising:
- (i) a heavy chain variable region sequence (SEQ ID NO:10) comprising Met49, Ser55 and Ile58, and a light chain variable region sequence (SEQ ID NO:11) comprising Phe36, Val44, Phe49 and Ile85 [e.g., antibody 10738]; or (ii) a heavy chain variable region sequence (SEQ ID NO:10) comprising Asn44, Ser55 and Thr93, and a light chain variable region sequence (SEQ ID NO:11) comprising Phe36, Phe49 and Leu73 [e.g., antibody 10810].

The anti-HER3 antibody (e) may also be an antibody corresponding to antibody 10738 or 10810, but comprising at least one additional substitution in any of the heavy chain and/or light chain amino acid residues indicated as "Xaa" in Table 4, e.g. substitution in one, two, three or four of such "Xaa" residues.

Examples of a preferred anti-HER3 antibody (f) are antibodies comprising:
(i) a heavy chain variable region sequence (SEQ ID NO:12) comprising Val46, Met49, Ser55 and Arg72, and a light chain variable region sequence (SEQ ID NO:13) comprising Val21, Val44 and Phe87, and optionally Thr29 [e.g., antibody 11006]; or
(ii) a heavy chain variable region sequence (SEQ ID NO:12) comprising Phe41, Val46, Met49, Ser55 and Arg72, and a light chain variable region sequence (SEQ ID NO:13) comprising Val21, Val44, Tyr71, Phe87 and Leu104 [e.g., antibody 11052].

The anti-HER3 antibody (f) may also be an antibody corresponding to antibody 11006 or 11052, but comprising at least one additional substitution in any of the heavy chain and/or light chain amino add residues indicated as "Xaa" in Table 4, e.g. substitution in one, two, three or four of such "Xaa" residues.

It is well-known in the art that antibodies exist as different isotypes, such as the human isotypes IgG1, IgG2, IgG3, IgG4, IgA1 and IgA2, or the murine isotypes IgG1, IgG2a, IgG2b, IgG3 and IgA. An antibody of the invention may be of any isotype, including IgG, IgM, IgE, IgA, or IgD.

Humanized Antibody Compositions

A further aspect of the invention relates to a recombinant antibody composition (or mixture) comprising at least two humanized antibodies of the invention directed against at least two different receptors selected from EGFR, HER2 and HER3. The terms "polyclonal antibody" or "mixture of [monoclonal] antibodies" refer to a composition of two or more different antibody molecules which are capable of binding to or reacting with different specific antigenic determinants on the same or on different antigens. In the context of the present invention, the individual antibodies of a mixture of antibodies bind to different antigenic determinants of at least two HER family receptors. In the case of antibody mixtures containing two different antibodies that bind to the same receptor, the individual antibodies preferably bind to different epitopes of that receptor, more preferably distinct and substantially non-overlapping epitopes.

The terms "pan-HER" or "pan-HER antibody composition" refer to a composition of antibody molecules which are capable of binding to at least two different antigens on at least two HER family receptors. In the context of the present invention, the individual antibodies of an antibody composition bind to different antigenic determinants of the HER family. The individual antibodies of the antibody composition may thus bind to EGFR and HER2, EGFR and HER3, HER2 and HER3, EGFR, HER2 and HER3, preferably to the three receptors EGFR, HER2 and HER3.

The term "epitope" is used to describe a part of a larger molecule (e.g. antigen or antigenic site) having antigenic or immunogenic activity in an animal. An epitope having immunogenic activity is a portion of a larger molecule that elicits an antibody response in an animal. An epitope having antigenic activity is a portion of a larger molecule to which an antibody immunospecifically binds as determined by any method known in the art. Antigenic epitopes are not necessarily immunogenic. An antigen is a substance to which an antibody or antibody fragment immunospecifically binds, e.g. a toxin, virus, bacteria, protein or DNA. An antigen or antigenic site often has more than one epitope, unless it is very small, and is often capable of stimulating an immune response. Epitopes may be linear or conformational. A linear epitope generally consists of about 6 to 10 adjacent amino acids on a protein molecule that are recognized by an antibody. In contrast, a conformational epitope consists of amino acids that are not arranged sequentially, but where an antibody recognizes a particular three-dimensional structure. When a protein molecule folds into a three-dimensional structure, the amino acids forming the epitope are juxtaposed, enabling the antibody to recognize the conformational epitope. In a denatured protein only linear epitopes are recognized. A conformational epitope, by definition, must be on the outside of the folded protein.

The term "distinct epitopes" refers to the fact that when two different antibodies of the invention bind distinct epitopes, there is less than 100% competition for antigen binding, preferably less than 80% competition for antigen binding, more preferably less than 50% competition for antigen binding, and most preferably as little competition as possible, such as less than about 25% competition for antigen binding. Antibodies capable of competing with each other for binding to the same antigen may bind the same or overlapping epitopes or may have a binding site in close vicinity of one another, so that competition is mainly caused by steric hindrance. An analysis for "distinct epitopes" of antibody pairs may be performed by methods known in the art, for example by way of binding experiments under saturating antibody conditions using either FACS (fluorescence activated cell sorting) or other flow cytometry analysis on cells expressing the relevant receptor antigen and individual fluorescent labeled antibodies, or by Surface Plasmon Resonance (SPR) using antigen captured or conjugated to a flow cell surface.

The distinct epitopes are preferably "non-overlapping" in the sense that two different antibodies in a composition of the invention that bind to the same receptor have a sufficiently low competition for antigen binding that the two antibodies are able to bind their respective epitopes simultaneously. It will be understood by persons skilled in the that there can be different degrees of overlap, and that distinct epitopes can be considered to be "non-overlapping" in spite of the presence of some degree of competition, as long as the respective antibodies are able to substantially bind their epitopes. This is generally considered to be the case when the competition for antigen binding between two antibodies is less than about 50%. Methods for determining competition between antibodies are known in the art, for example using Surface Plasmon Resonance (SPR) as described e.g. in WO 2011/107957.

Antibodies binding to different epitopes on the same antigen can have varying effects on the activity of the antigen to which they bind, depending on the location of the epitope. An antibody binding to an epitope in an active site of the antigen may block the function of the antigen completely, whereas another antibody binding at a different epitope may have no or little effect on the activity of the antigen alone. Such antibodies may, however, still activate complement and thereby result in the elimination of the antigen-expressing cell, and may result in synergistic growth inhibitory effects when combined with one or more antibodies binding at different epitopes on the same antigen. In the context of the present invention, the epitope is a portion of the extracellular domain of EGFR, HER2 or HER3 (either wild-type or mutated). An anti-EGFR antibody of the invention will thus bind to the extracellular domain of EGFR, an anti-HER2 antibody of the invention will bind to the extracellular domain of HER2, and an anti-HER3 antibody of the invention will bind to the extracellular domain of HER3.

Particular embodiments of this aspect of the invention include, with reference to humanized antibodies (a)-(f) outlined above, compositions comprising:
    anti-EGFR antibody (a) and anti-HER2 antibody (c);
    anti-EGFR antibody (a) and anti-HER2 antibody (d);
    anti-EGFR antibody (a) and anti-HER3 antibody (e);
    a anti-EGFR antibody (a) and anti-HER3 antibody (f);
    anti-EGFR antibody (b) and anti-HER2 antibody (c);
    anti-EGFR antibody (b) and anti-HER2 antibody (d);
    anti-EGFR antibody (b) and anti-HER3 antibody (e);
    anti-EGFR antibody (b) and anti-HERB antibody (f);
    a anti-HER2 antibody (c) and anti-HER3 antibody (e);
    anti-HER2 antibody (c) and anti-HERB antibody (f);
    anti-HER2 antibody (d) and anti-HER3 antibody (e); or
    anti-HER2 antibody (d) and anti-HER3 antibody (f).

In one embodiment, the invention relates to a recombinant antibody composition comprising at least one humanized anti-EGFR antibody, at least one humanized anti-HER2 antibody, and at least one humanized anti-HER3 antibody.

In some embodiments, the invention relates to an antibody composition comprising at least one humanized anti-EGFR antibody, at least one humanized anti-HER2 antibody, and at least one humanized anti-HER3 antibody, wherein:
    the at least one humanized anti-EGFR antibody is selected from (a) an antibody comprising the heavy chain variable region sequence of SEQ ID NO:1 and the light chain variable region sequence of SEQ ID NO:2 or SEQ ID NO:3, and (b) an antibody comprising the heavy chain variable region sequence of SEQ ID NO:4 and the light chain variable region sequence of SEQ ID NO:5;
    the at least one humanized anti-HER2 antibody is selected from (c) an antibody comprising the heavy chain variable region sequence of SEQ ID NO:6 and the light chain variable region sequence of SEQ ID NO:7, and (d) an antibody comprising the heavy chain variable region sequence of SEQ ID NO:8 and the light chain variable region sequence of SEQ ID NO:9; and
    the at least one humanized anti-HER3 antibody is selected from (e) an antibody comprising the heavy chain variable region sequence of SEQ ID NO:10 and the light chain as variable region sequence of SEQ ID NO:11, and (f) an antibody comprising the heavy chain variable region sequence of SEQ ID NO:12 and the light chain variable region sequence of SEQ ID NO:13.

In the case of an antibody composition comprising one anti-EGFR antibody, one anti-HER2 antibody and one anti-HER3 antibody, the composition may thus comprise, with reference to humanized antibodies (a)-(f) outlined above:
    anti-EGFR antibody (a), anti-HER2 antibody (c), and anti-HER3 antibody (e);
    anti-EGFR antibody (a), anti-HER2 antibody (c), and anti-HER3 antibody (f);
    anti-EGFR antibody (a), anti-HER2 antibody (d), and anti-HER3 antibody (e);
    anti-EGFR antibody (a), anti-HER2 antibody (d), and anti-HER3 antibody (f);
    anti-EGFR antibody (b), anti-HER2 antibody (c), and anti-HER3 antibody (e);
    anti-EGFR antibody (b), anti-HER2 antibody (c), and anti-HER3 antibody (f);
    anti-EGFR antibody (b), anti-HER2 antibody (d), and anti-HER3 antibody (e); or
    anti-EGFR antibody (b), anti-HER2 antibody (d), and anti-HER3 antibody (f).

Examples of preferred compositions comprising one anti-EGFR antibody, one anti-HER2 antibody and one anti-HER3 antibody are, e.g.:
    antibodies 10292, 10704 and 10738;
    antibodies 10292, 10704 and 10810;
    antibodies 10292, 10704 and 11006;
    antibodies 10292, 10704 and 11052;
    antibodies 10460, 10704 and 10738;
    antibodies 10460, 10704 and 10810;
    antibodies 10460, 10704 and 11006;
    antibodies 10460, 10704 and 11052;
    antibodies 11294, 10704 and 10738;
    antibodies 11294, 10704 and 10810;
    antibodies 11294, 10704 and 11006; and
    antibodies 11294, 10704 and 11052.

In a still more preferred embodiment, the antibody composition comprises six humanized antibodies, i.e. two humanized antibodies directed against each of the three receptors EGFR, HER2 and HER3, where each pair of antibodies that bind the same receptor bind to distinct and non-overlapping epitopes of that receptor. This may in particular be a composition comprising anti-EGFR antibodies (a) and (b), anti-HER2 antibodies (c) and (d), and anti-HER3 antibodies (e) and (f). In this case, one, two, three, four, five or all of the six antibodies may be selected from antibodies 10292, 10460, 11294, 10560, 11302, 10704, 11249, 11145, 10738, 10810, 11006 and 11052.

In a particular embodiment, the antibody composition comprises:
    (a) anti-EGFR antibody 10292, 10460, or 11294;
    (b) anti-EGFR antibody 10560 or 11302;
    (c) anti-HER2 antibody 10704 or 11249;
    (d) anti-HER2 antibody 11145;
    (e) anti-HER3 antibody 10738 or 10810; and
    (f) anti-HERB antibody 11006 or 11052.

Alternatively, any one or more of the antibodies (a)-(f) in this embodiment may comprise at least one additional substitution in any of the heavy chain and/or light chain amino acid residues indicated as "Xaa" in Table 4, e.g. substitution in up to five or six of such "Xaa" residues per antibody for one or more of the antibodies in the composition, such as substitution in one, two, three or four of such "Xaa" residues per antibody for one or more of the antibodies in the composition.

In a preferred embodiment, the antibody composition comprises anti-EGFR antibodies 11294 and 11302, anti-HER2 antibodies 11249 and 11145, and anti-HER3 antibodies 10738 and 11052. The antibody composition may comprise (a) an antibody comprising the heavy chain variable region sequence of SEQ ID NO:42 and the light chain variable region sequence of SEQ ID NO:43; (b) an antibody comprising the heavy chain variable region sequence of SEQ ID NO:46 and the light chain variable region sequence of SEQ ID NO:47; (c) an antibody comprising the heavy chain variable region sequence of SEQ ID NO:50 and the light chain variable region sequence of SEQ ID NO:51; (d) an antibody comprising the heavy chain variable region sequence of SEQ ID NO:52 and the light chain variable region sequence of SEQ ID NO:53; (e) an antibody comprising the heavy chain variable region sequence of SEQ ID NO:54 and the light chain variable region sequence of SEQ ID NO:55; and (f) an antibody comprising the heavy chain variable region sequence of SEQ ID NO:60 and the light chain variable region sequence of SEQ ID NO:61.

Although it is possible for the individual antibodies of an antibody mixture of the invention to include antibodies of more than one isotype, they may all be of the same isotype.

Properties of the Humanized Antibodies and Antibody Compositions

The humanized antibodies of the invention bind to the HER- or EGFR-family members, EGFR, HER2, or HER3. The term "HER" stands for "Human Epidermal growth factor Receptor" and is often used interchangeably with the term "ErbB" to characterize the subgroup of the receptor tyrosine kinases (RTKs) consisting of the four members EGFR/ErbB, HER2/ErbB2, HER3/ErbB3 and HER4/ErbB4. Together, these four receptors constitute the "HER family" (or ErbB or EGFR family) receptors.

Binding of one or more antibodies of the invention, in particular a pan-HER antibody composition of the invention, to HER family receptors preferably inhibits the growth and proliferation of cells expressing the receptors (i.e. typically tumor cells). The mechanism(s) involved may, for example, include one or more of the following: preventing receptor dimerization, preventing ligand binding, promoting internalization and degradation of the receptor, reducing tyrosine kinase domain (TKD) phosphorylation, reducing receptor signaling, and inducing phagocytosis, CDC and/or ADCC.

As used herein, the term "inhibits growth" (e.g., referring to cells) is intended to include any measurable decrease in the proliferation (increase in number of cells) or metabolism of a cell when contacted with an anti-HER family antibody or pan-HER antibody composition as compared to the growth of the same cells in the absence of the antibody or composition, e.g. inhibition of growth of a cell culture by at least about 10%, and preferably more, such as at least about 20% or 30%, more preferably at least about 40% or 50%, such as at least about 60%, 70%, 80%, 90%, 95% or 99%, or even about 100%. Growth inhibition can e.g. be determined in relevant cancer cell lines as described in the examples below.

Bispecific Binding Molecules

In a further aspect, the binding specificities of any two individual antibodies disclosed herein may be combined in one bispecific binding molecule. Such a bispecific binding molecule may have the binding specificities of two antibodies targeting two different receptors selected from EGFR, HER2 and HER3, or it may have the binding specificities of two antibodies targeting the same receptor. For example, a bispecific binding molecule may have the binding specificities of anti-EGFR antibodies (a) and (b), the binding specificities of anti-HER2 antibodies (c) and (d), or the binding specificities of anti-HER3 antibodies (e) and (f). More particularly, a bispecific binding molecule may e.g. have the binding specificities of (1) anti-EGFR antibody 10292, 10460, or 11294, and anti-EGFR antibody 10550 or 11302; (2) anti-HER2 antibody 10704 or 11249, and anti-HER2 antibody 11145; or (3) anti-HER3 antibody 10738 or 10810, and anti-HER3 antibody 11006 or 11052. The bispecific binding molecule may be a dual variable domain antibody, i.e. wherein the two arms of the antibody comprise two different variable domains, or may be in the form of an antibody fragment such as a bispecific Fab fragment or a bispecific scFv.

Nucleic Acid Molecules, Vector, and Production of Antibodies and Antibody Compositions of the Invention Further aspects of the invention relate to nucleic acid molecules comprising a nucleotide sequence that encodes an antibody of the invention, in particular an antibody selected from the group consisting of antibodies 10292, 10460, 11294, 10560, 11302, 10704, 11249, 11145, 10738, 10810, 11006 and 11052, or encoding a heavy and/or light chain variable region sequence of such an antibody, as well as an expression vectors comprising such a nucleic acid molecule, and host cells comprising the nucleic acid molecule or expression vector, wherein said host cells are capable of expressing an antibody encoded by the nucleic acid molecule.

The term "vector" refers to a nucleic acid molecule into which a nucleic acid sequence can be inserted for transport between different genetic environments and/or for expression in a host cell. A vector that carries regulatory elements for transcription of the nucleic acid sequence (at least a suitable promoter) is referred to as an "an expression vector". The terms "plasmid" and "vector" may be used interchangeably. Expression vectors used in the context of the present invention may be of any suitable type known in the art, e.g. a plasmid or a viral vector.

An additional aspect of the invention relates to methods for producing humanized recombinant antibodies and compositions comprising the antibodies of the invention. One embodiment of this aspect of the invention relates to a method for producing an antibody as defined herein, comprising providing a host cell capable of expressing the antibody, cultivating said host cell under conditions suitable for expression of the antibody, and isolating the resulting antibody.

In a further embodiment, the invention relates to a method for producing a recombinant antibody composition comprising at least one humanized recombinant anti-EGFR antibody, at least one humanized recombinant anti-HER2 antibody and at least one humanized recombinant anti-HER3 antibody, the method comprising:

providing at least first, second and third host cells, wherein the first host cell is capable of expressing a recombinant anti-EGFR antibody of the invention, the second host cell is capable of expressing a recombinant anti-HER2 antibody of the invention, and the third host cell is capable of expressing a recombinant anti-HER3 antibody of the invention, cultivating the first, second and third host cells under conditions suitable for expression of the anti-EGFR antibody, the anti-HER2 antibody and the anti-HER3 antibody, and isolating the resulting antibodies.

An antibody or antibody composition of the present invention may be produced by methods generally known in the art for production of recombinant monoclonal or polyclonal antibodies. Thus, in the case of production of a single antibody of the invention, any method known in the art for production of recombinant monoclonal antibodies may be used. For production of an antibody composition of the invention comprising a mixture of antibodies, the individual antibodies may be produced separately, i.e. each antibody being produced in a separate bioreactor, or the individual antibodies may be produced together in single bioreactor. If the antibody composition is produced in more than one bioreactor, the purified antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in WO 2009/129814 (incorporated by reference).

In the case of production individual antibodies in a single bioreactor, this may be performed e.g. as described in WO 2004/061104 or WO 2008/145133 (both of which are incorporated herein by reference). The method described in WO 2004/061104 is based on site-specific integration of the antibody coding sequence into the genome of the individual host cells, while the method of WO 2008/145133 involves an alternative approach using random integration to produce antibodies in a single bioreactor.

Further information regarding methods suitable for preparing the antibodies and compositions of the invention may be found in WO 2012/059857 (incorporated by reference).

Therapeutic Compositions

Another aspect of the invention is a pharmaceutical composition comprising as an active ingredient an antibody or antibody composition of the invention. Such compositions are intended for amelioration, prevention and/or treatment of cancer. The pharmaceutical composition may be administered to a human or to a domestic animal or pet, but will typically be administered to humans.

The ratio between the individual antibodies in a therapeutic composition of the invention, or, in the case of individual antibodies of the invention being administered simultaneously, sequentially or separately, will often be such that the antibodies are administered in equal amounts, but this need not necessarily be the case. Thus, a composition of the invention comprising two anti-EGFR family antibodies will often contain them in approximately a 1:1 ratio, and a composition comprising three anti-EGFR family antibodies will often contain them in approximately a 1:1:1 ratio. Similarly, an antibody composition comprising six antibodies, two against each of the receptors EGFR, HER2 and HER3, will often contain them in approximately a 1:1:1:1:1:1 ratio. Depending on the characteristics of the individual antibodies, however, it may be desirable to use non-equal amounts of the different antibodies. Suitable ratios for the different anti-HER antibodies in compositions of the invention may be determined as described in WO 2010/040356 (incorporated herein by reference), which describes methods for identifying and selecting the optimal stoichiometric ratio between chemical entities in a combinatorial drug product, e.g. a polyclonal antibody composition, to obtain a combinatorial drug with optimal potency and efficacy.

In addition to the humanized recombinant antibodies of the invention or binding fragments thereof, the pharmaceutical composition will further comprise at least one pharmaceutically acceptable diluent, carrier or excipient. These may for example include preservatives, stabilizers, surfactants/wetting agents, emulsifying agents, solubilizers, salts for regulating the osmotic pressure and/or buffers. Solutions or suspensions may further comprise viscosity-increasing substances, such as sodium carboxymethylcellulose, carboxymethylcellulose, dextran, polyvinylpyrrolidone or gelatin. A suitable pH value for the pharmaceutical composition will generally be in the range of about 5.5 to 8.5, such as about 6 to 8, e.g. about 7, maintained where appropriate by use of a buffer.

Conventional pharmaceutical practice may be employed to provide suitable formulations or compositions to administer to e.g. cancer patients by conventional administration routes known in the art. Similarly, the pharmaceutical compositions of the invention may be prepared in a manner known per se for preparation of recombinant antibody compositions. For further information on formulation, administration, etc., see PCT/IB2011/054834.

Therapeutic Uses of Antibodies and Compositions of the Invention

The antibodies and compositions of the present invention may be used for the treatment or amelioration of a disease in a mammal, in particular treatment of cancer in humans. The term "treatment" as used herein refers to administration of an antibody or, preferably, antibody composition of the invention in a sufficient amount to ease, reduce, ameliorate or eradicate (cure) symptoms or disease states. Administration of two or more pan-HER antibodies of the invention will generally be by way of simultaneous administration of the antibodies, preferably in the form of a composition containing all of the pan-HER antibodies to be used for treatment. However, it is also possible to administer two or more antibodies of the invention separately. References herein to e.g. administration of a recombinant antibody composition comprising at least two anti-HER family antibodies should therefore be understood as encompassing not only administration of a composition comprising the at least two antibodies as such, but also separate administration of the antibodies. Combinations of two or more antibodies of the invention can thus be administered simultaneously, sequentially or separately. One embodiment of the invention is a method of preventing, treating or ameliorating one or more symptoms associated with cancer in a human or other mammal, comprising administering an effective amount of the pharmaceutical antibody composition of the present invention to said mammal.

A particular embodiment relates to a method for treating a patient, typically a human patient, with a disorder characterized by expression or overexpression of or dependency on any one or more of the EGFR family receptors EGFR, HER2 and HER3, in particular cancer, the method comprising administering to said patient a recombinant antibody composition or pharmaceutical composition as defined herein. The term "HER dependency" refers to a cancer cell with dependency on one or more of the HER family receptors for maintaining malignant properties such as proliferation, growth, motility, invasion, survival and/or chemo resistance. Dependency may be caused by receptor overexpression, receptor mutations, autocrine growth factor production, and/or cross-talk with other receptor systems.

In a further embodiment, the invention relates to a method for treating cancer in a patient, typically a human patient, having acquired resistance to treatment with an antibody and/or a tyrosine kinase inhibitor (TKI), the method comprising administering to said patient an effective amount of a recombinant antibody composition or pharmaceutical composition as defined herein.

Based upon a number of factors, the following tumor types in particular may be indicated for treatment with an antibody composition of the invention: breast, ovarian, gastric, colon, rectum, prostate, bladder, pancreas, melanoma, head and neck, and non-small cell lung cancer. Antibody compositions of the invention are contemplated to be particularly applicable to treatment of cancers that overexpress EGFR or HER2, for example certain epithelial cancers such as many breast cancers, ovarian cancers and gastric (stomach) cancers.

In one embodiment, antibody compositions of the invention are used to treat a patient with pancreatic cancer. The patient may have a KRAS mutation.

In one embodiment, the patient has not been treated for cancer previously. In another embodiment, the patient has been treated for cancer previously. The patient may have been treated with cetuximab, trastuzumab, or pertuzumab previously. The cancer in the patient may have acquired resistance to cetuximab, trastuzumab, or pertuzumab.

In connection with each of these indications, two main clinical pathways are contemplated, namely 1) adjunctive therapy in connection with at least one additional therapeutic treatment or 2) as a monotherapy.

1) Adjunctive therapy: In adjunctive therapy, also known as combination therapy, patients will be treated with antibodies of the present invention in combination with at least one additional therapeutic treatment, typically a chemotherapeutic or antineoplastic agent and/or radiation therapy. Alternatively or additionally, the composition of the invention may also be used in combination with a different anti-cancer antibody, e.g. an antibody targeting VEGF. The primary cancer targets listed above may thus be treated by administration of an antibody or composition of the invention in addition to standard first line and second line therapy. Protocol designs will address effectiveness as assessed e.g. by reduction in tumor mass as well as the ability to reduce usual doses of standard chemotherapy. Such dosage reductions may allow additional and/or prolonged therapy by reducing dose-related toxicity of the chemotherapeutic agent.

By combining the antibody compositions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. Preferably, the compound is selected from the group consisting of retinoic acid, phenylbutyrate, all-trans-retinoic acid and active form vitamin D.

Pharmaceutical articles comprising an antibody composition of the invention and at least one chemotherapeutic or antineoplastic compound may be used as a combination treatment for the simultaneous, separate or successive administration in cancer therapy. The chemotherapeutic compound may by any chemotherapeutic agent suitable for treatment of the particular cancer in question, for example an agent selected from the group consisting of alkylating agents, for example platinum derivatives such as cisplatin, carboplatin and/or oxaliplatin; plant alkoids, for example paclitaxel, docetaxel and/or irinotecan; antitumor antibiotics, for example doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, for example fluorouracil and/or other fluoropyrimidines.

It is also contemplated that antibody composition of the invention may be used in adjunctive therapy in connection with tyrosine kinase inhibitors. These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several tyrosine kinase inhibitors that block HER2 kinase are currently in clinical development. Some of these also target EGFR or other EGFR family receptors. For a review of these TKIs see Spector et al. (2007) *Breast Cancer Res.* 9(2): 205. Pharmaceutical articles comprising an antibody composition of the invention and at least one TKI targeting HER2 may thus also be used as a combination treatment for the simultaneous, separate or successive administration in cancer therapy.

In other embodiments, the antibody compositions of the present invention may be used in combination with other antibody therapeutics, e.g. an antibody against VEGF (e.g. Avastin®). In yet other embodiments, the antibody compositions of the present invention may be used in combination with an agent known to stimulate cells of the immune system, such combination treatment leading to enhanced immune-mediated enhancement of the efficacy of the antibody compositions of the invention. Examples of such immune-stimulating agents include recombinant interleukins (e.g. IL-21 and IL-2).

2) Monotherapy: In connection with the use of the antibody composition in accordance with the present invention in monotherapy of tumors, the antibody composition may be administered to patients without concurrent use of a chemotherapeutic or antineoplastic agent, i.e. as a stand-alone therapy.

Immunoconjugates

Another option for therapeutic use of the compositions of the invention is in the form of immunoconjugates, i.e. antibodies conjugated to one or more anti-cancer agents. In particular in the case of compositions of the invention that bind distinct epitopes, it is contemplated that this may generate a cross-linked antibody-receptor lattice on the cell surface, thereby potentially resulting in an increased level of receptor internalization as compared to the use of a single monoclonal antibody. Conjugation of one or more of the individual antibodies of such a composition to one or more anti-cancer agents therefore has the potential to specifically and effectively deliver the conjugated anti-cancer agents to the interior of tumor cells, thereby augmenting the effect of the antibody composition of the invention to provide an improved tumor cell-killing activity.

Various types of anti-cancer agents may be conjugated to the antibodies of the invention, including cytotoxic agents (including conventional chemotherapy agents and other small molecule anti-cancer drugs), cytokines (in which case the conjugate may be termed an "immunocytokine"), toxins (in which case the conjugate may be termed an "immunotoxin") and radionuclides, and a few immunoconjugates have already been approved for clinical use. These include Zevalin® (a murine anti-CD20 antibody conjugated to $^{90}Y$), Bexxar® (a murine anti-CD20 antibody conjugated to $^{131}I$) and Mylotarg® (a humanized anti-CD33 antibody conjugated to calicheamicin). Other immunoconjugates that have been tested in clinical trials include antibodies conjugated to e.g. doxorubicin or a maytansinoid compound. Immunotoxins that have been tested in clinical trials include several antibodies conjugated to a truncated *Pseudomonas exotoxin* A. An immunocytokine comprising a humanized EpCAM antibody conjugated to IL-2 has also been tested.

In the case of antibodies of the invention conjugated to cytotoxic agents, these may e.g. belong to any of the major classes of chemotherapy drugs, including alkylating agents (e.g. carboplatin, cisplatin, oxaliplatin), antimetabolites (e.g. methotrexate, capecitabine, gemcitabine), anthracyclines (e.g. bleomycin, doxorubicin, mitomycin-C) and plant alkaloids (e.g. taxanes such as docetaxel and paclitaxel, and vinca alkaloids such as vinblastine, vincristine and vinorelbine). Since the use of immunoconjugates specifically directs the anti-cancer agent to the tumors, and in particular to the interior of the tumor cells subsequent to internalization, immunoconjugates based on the antibodies of the invention may advantageously be based on highly cytotoxic agents such as calicheamicin or maytansine derivatives, or on toxins such as bacterial toxins (e.g. *Pseudomonas exotoxin* A, diphtheria toxin) or plant toxins (e.g. ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the invention. For example, with two antibodies it would be possible to conjugate the antibodies to two or more different anti-cancer drugs or to conjugate one antibody to a prodrug which is activated by an agent such as an enzyme conjugated to the other antibody. The general concept of antibody-directed enzyme prodrug therapy (ADEPT) has been described for monoclonal antibodies, where a prodrug is activated by an enzyme targeted to the tumor by a mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al. (2005) *Nature Biotechnology* 23(9): 1137-1146; Schrama et al. (2006) *Nature Reviews/Drug Discovery* 5:147-159; and Rohrer (2009) *chimica oggi/Chemistry Today* 27(5):56-60.

Compositions of the invention comprising antibodies directed against two or more EGFR family receptors may contain a single antibody in the form of an immunoconjugate, or they may contain two or more antibodies in the form of an immunoconjugate, e.g. one or possibly two immunoconjugates targeting each of the receptors EGFR, HER2 and HER3.

Dose and Route of Administration

The antibody compositions of the invention will be administered in an effective amount for treatment of the condition in question, i.e. at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

An effective amount for tumor therapy may be measured by its ability to stabilize disease progression and/or ameliorate symptoms in a patient, and preferably to reverse disease progression, e.g. by reducing tumor size. The ability of an antibody or composition of the invention to inhibit cancer may be evaluated by in vitro assays, e.g. as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

While specific dosing for antibodies in accordance with the invention has not yet been determined, certain dosing considerations can be determined through comparison with a similar product (e.g. a monoclonal antibody directed against HER2 or EGFR) that has been approved for therapeutic use. It is thus contemplated that an appropriate dosage of an antibody composition of the invention will be similar to the recommended dosage for the anti-HER2 monoclonal antibody trastuzumab (Herceptin®) or the anti-EGFR monoclonal antibody panitumumab (Vectibix®). Depending on the particular condition, Herceptin® is administered (by way of infusion) for treatment of breast cancer at either an initial close of 4 mg/kg and subsequent weekly doses of 2 mg/kg, or an initial dose of 8 mg/kg and subsequent closes of 6 mg/kg every three weeks, while Vectibix® is administered at a dose of 6 mg/kg every 14 days.

It is contemplated that a suitable dose of an antibody composition of the invention will be in the range of 0.1-100 mg/kg, such as about 0.5-50 mg/kg, e.g. about 1-20 mg/kg. The antibody composition may for example be administered in a dosage of at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg; and e.g. up to at most 50 mg/kg, such as up to at the most 30 mg/kg, e.g. up to at the most 20 mg/kg, such as up to at the most 15 mg/kg. Administration will normally be repeated at suitable intervals, e.g. once every week, once every two weeks, once every three weeks, or once every four weeks, and for as long as deemed appropriate by the responsible doctor, who may optionally increase or decrease the dosage as necessary.

Three distinct delivery approaches are contemplated for delivery of the antibodies of the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favourable for obtaining high dose of antibody at the tumor and to minimize antibody clearance. Similarly, certain solid tumors possess vasculature that is appropriate for regional perfusion. Regional perfusion may allow the obtainment of a high dose of the antibody at the site of a tumor and minimise short term clearance of the antibody.

As with any protein or antibody infusion-based therapeutic product, safety concerns are related primarily to (i) cytokine release syndrome, i.e. hypotension, fever, shaking, chills, (ii) the development of an immunogenic response to the protein (i.e. development of human antibodies by the patient to the recombinant antibody product), and (iii) toxicity to normal cells that express the HER family receptors, e.g. many epithelial cells. Standard tests and follow-up procedures are utilised to monitor any such safety concerns.

Diagnostic Uses and Compositions

The antibodies of the present invention also are useful in diagnostic processes (e.g., in vitro, ex vivo). For example, the antibodies can be used to detect and/or measure the level of EGFR, HER2, or HER3 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies described herein.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

The instant application contains a Sequence Listing that has been submitted in ASCII format via EFS-Web and is hereby incorporated by reference in its entirety. Said ASCII file, created on Nov. 14, 2016, is named 022675D1048.txt and is 95,594 bytes in size.

The following examples are meant to illustrate the methods and materials of the present invention. Suitable modifications and adaptations of the described conditions and parameters normally encountered in the art which are obvious to those skilled in the art are within the spirit and scope of the present invention. The terms "antigen-binding fragment" and "antigen-binding portion" are used interchangeably herein.

EXAMPLES

Example 1: Humanization of Chimeric Antibodies

Identification of Acceptor Frameworks and Critical Positions for Mutation

The method chosen for the humanization was based on complementarity determining region (CDR) grafting followed by back mutation of critical residues using a combinatorial library approach, where all combinations of up to 13 back mutations were evaluated simultaneously.

The CDRs of the donor murine antibodies were grafted into the closest human V-region acceptor framework, which was found by comparing the V region amino acid sequences of the donor antibodies with the human germline repertoire of V and J region sequences (IMGT reference directory). The closest germline V and 3 regions identified for each antibody are shown in Table 5 below.

For 1277VL, the closest human germline V-region was IGKV2-30*02. However, since the IGKV2 family is rarely used in the human repertoire, a second acceptor framework was also selected from the IGKV1 family. Each of the two frameworks were used for generation of a VL back mutation library and combined with the single 1277 VH back mutation library.

Since CDR grafting alone may not be sufficient to recreate the binding specificity and affinity, and thus biological activity, of a rodent antibody, back mutations may have to be introduced at critical positions. Potentially critical positions include those that are somatically hypermutated in the donor antibody, positions that may be in direct contact with the antigen or influencing CDR structure (structure determining residues or Vernier zone residues), positions in the VH/VL interface or responsible for the VH/VL packing angle, and positions that are occupied by statistically rare (as compared to the antibody repertoire) or structurally unfavorable residues. These positions can be identified using information available in the literature and in antibody databases (e.g., Padlan (1994) Mol.Immunol. 31: 169-217; Honegger and Plückthun (2001) J.Mol.Biol. 309: 657-670; Martin and Thornton (1996) J.Mol.Biol. 263: 800-815; Foote and Winter (1992) J.Mol.Biol. 224: 487-499), or by performing structural modeling of the in silico grafted sequence. A combination of these two approaches was used to identify potentially critical positions for back mutation in each of the antibodies.

In addition to the back mutation positions, exposed unwanted sequence motifs in the CDRs were also identified. These motifs included sites for asparagine deamidation (Asn-Gly), aspartate isomerization (Asp-Gly) and methionine oxidation. The identified sequence motifs were altered by conservative substitution or replacement with a frequently occurring amino acid residue at one of the positions (as opposed to back mutation to the murine sequence).

A maximum of 13 critical positions were identified and included in the library design for each antibody (Table 5). The number of positions was selected on the basis of the size of the resulting back mutation libraries. For example, if 13 positions are varied between two different amino acids (e.g. human or murine residue) this yields 8192 variants when combined into one molecular library. The location of the identified positions in each antibody is shown in the appended sequence listing, where amino acid residues indicated by "Xaa" are potentially critical positions selected for mutation.

TABLE 5

Design of libraries for humanization

| Library (specificity) | Heavy chain human germline genes and number of positions for mutation | | | Light chain human germline genes and number of positions for mutation | | |
|---|---|---|---|---|---|---|
| | V | J | Number of critical positions* | V | J | Number of critical positions* |
| 1277 (EGFR) | 3-48*03 | 6*01 | 4 | 1-39*03 | 4*01 | 9 |
| 1277A (EGFR) | 3-48*03 | 6*01 | 4 | 2-30*02 | 4*01 | 6 |
| 1565 (EGFR) | 1-46*03 | 4*01 | 10 | 1-13*02 | 4*01 | 3 |
| 4384 (HER2) | 1-46*03 | 5*01 | 8 | 1-33*01 | 4*01 | 5 |
| 4517 (HER2) | 3-21*02 | 6*01 | 6 | 1D-39*01 | 4*01 | 7 |
| 5038 (HER3) | 4-31*03 | 4*01 | 7 | 1-33*01 | 1*01 | 6 |
| 5082 (HER3) | 4-31*03 | 4*01 | 6 | 1D-39*01 | 4*01 | 7 |

*Number of positions where back mutations were introduced or unwanted sequence motifs altered.

Generation of Back Mutation Libraries

Back mutation libraries for each VH and VL sequence were synthesized by PCR gene assembly of overlapping DNA oligos spanning 60-80 base pairs of the sequence. The light chain constant region was added by overlap extension PCR to generate full-length light chain genes. Molecular libraries of humanized antibody variants were prepared by sub-cloning of the VH and light chain libraries for each antibody into a mammalian expression vector followed by transient expression of individual antibody variants in HEK293 cells in 384-well format as described elsewhere (Meijer et al. (2009) Methods Mol Biol. 525:261-77). Expression supernatants were harvested and used for screening.

Off-Rate Screening of Humanization Libraries

The library expression supernatants were screened in a sandwich ELISA employing IgG capture by anti-human IgG Fc coated at low density followed by detection with monovalent biotinylated antigen. This ELISA setup allowed for sensitive and reliable ranking of binding affinity without interference from avidity effects or varying expression levels of individual clones. In total, 24 384-well plates were used for each library screening, corresponding to 8832 individual wells and a library sampling of approximately 1 (p=0.65 for retrieving a distinct library member). 5 µl of each library expression supernatant was incubated with coated anti-human IgG Fc capture antibodies at 4° C. overnight to ensure that all supernatants, regardless of antibody expression level, reached equilibrium binding. Next, wells were washed and biotinylated antigen (human EGFR, HER2 or HER3; Sino Biological, Beijing, P. R. China; biotinylated in-house) was added at a concentration previously determined to be sufficient for saturation of the chimeric antibody standards. The plates were washed and the antigen was allowed to dissociate from the captured antibodies for a predetermined time interval depending on the measured dissociation of the chimeric parent antibody standard. Finally, streptavidin-peroxidase polymer (Sigma) was added and the plates were developed using TPM-plus substrate (Kem-En-Tec Diagnostics, Taastrup, Denmark).

Approximately 100 hits from each library that yielded an OD signal similar to or higher than that of the chimeric parent antibody were subjected to off-rate ranking using an Octet® QK384 instrument (Fortebio, Menlo Park, Calif.). Protein G biosensors (Fortebio) were used for capturing of antibody from 40 µl of expression supernatant followed by incubation with human or cynomolgus antigen at 200 nM. Human antigens were obtained from Sino Biologicals and cynomolgus antigens were produced in-house by transient expression in CHO or HEK293 cells (Koefoed et al. (2011) mAbs, 3:6, 1-12). Subsequently, the biosensors were incubated in PBS and the dissociation of antigen was recorded for 20 min to allow for a reliable determination of the dissociation rates. The responses were globally fitted to a Langmuir 1:1 binding model for calculation of dissociation constants. Overall, multiple hits from each library were found to have dissociation rates from both human and cynomolgus antigen similar to or slower than that of the parent antibody.

Sequence Analysis

Plasmids encoding the hits selected for off-rate ranking were subjected to DNA sequencing (MWG Biotech, Ebersberg, Germany), and the obtained sequences were aligned and compared to the in silico generated CDR-grafted V regions. Alignments of selected hits are shown in FIGS. 1-6. All the hits from the screening of the initial libraries based on antibodies 1277 and 1565 were found to have retained the deamidation site (Asn-Gly) in CDRL1 and CDRH2, respectively, thus indicating the importance of the motif for the interaction with the target. However, only a single replacement mutation (Asn to Ser) was attempted in both cases, and it is quite likely that binding variants devoid of the sequence motif can be generated by saturated mutagenesis of one or both positions that make up the motif. Screening of the libraries generated by PCR-based saturated mutagenesis of the deamidation sites yielded hits devoid of this unwanted sequence motif (FIGS. 1 and 2). Potently binding antibody variants devoid of unwanted sequence motifs were found in all the other libraries.

Between four and ten hits from each library screening were selected on the basis of retained or improved binding to human and cynomolgus antigen, the number of back-mutations and absence of unwanted sequence motifs for expression in larger scale and purification by protein A chromatography. One of the humanized variants, antibody 11006, was found to have a fortuitous mutation in CDRL1 (I29T; SEQ ID NO:13 and FIG. 6) that was not part of the library design, but was nevertheless selected for expression due to improved dissociation rate and removal of an aspartate isomerization site in CDRH2.

Kinetic Binding Analysis of Humanized Variants by Surface Plasmon Resonance

Kinetic binding analysis of the purified humanized variants was performed on a ProteOn™ XPR36 biosensor (BioRad, USA) employing an IgG capture assay as described by Canziani et al. (Anal. Biochem. (2004) 325: 301-307) that allows for measurement of antibody affinities of whole IgG molecules against soluble antigen under monovalent conditions. Briefly, approximately 5000 resonance units (RU) of a monoclonal mouse anti-human IgG Fc antibody (GE Healthcare, Denmark) was conjugated to a GLC chip surface (BioRad, USA) according to the manufacturer's instructions, followed by capture of individual antibodies of the invention or a negative control on the anti-Fc sensor surface. The densities of captured antibodies were optimized for each clone, so that the binding of the highest antigen concentration employed in the assay did not exceed ~30 RU. Next, 250 µl monovalent antigen (Sino Biologicals) was injected at a flow rate of 50 µl/min in serial threefold dilutions from 100 nM stock to generate response curves. The chip surface was regenerated between cycles by stripping the captured antibody/antigen complexes off the surface with a 10-second injection of 3 M $MgCl_2$ (GE Healthcare, Denmark) repeated three times. Finally, binding responses were fitted to a Langmuir 1:1 binding model for calculation of the on-rate (kon or ka), off-rate (koff or kd) and affinity (KD) constants using double referencing. The results of the kinetic binding analysis show that the selected variants have retained or even improved affinity for the human and cynomolgus antigen as compared to the chimeric parent antibodies (Table 6).

TABLE 6

Binding affinity of chimeric parent antibodies and humanized antibodies

| Ab ID | Source library (specificity) | Human antigen | | | Cynomolgus antigen | | |
|---|---|---|---|---|---|---|---|
| | | $k_a$ ($M^{-1}s^{-1}$) | $k_d$ ($s^{-1}$) | $K_D$ (M) | $k_a$ ($M^{-1}s^{-1}$) | $k_d$ ($s^{-1}$) | $K_D$ (M) |
| 1277 | chimeric (EGFR) | 9.4E+05 | 3.5E−04 | 3.7E−10 | 6.6E+05 | 3.9E−04 | 5.9E−10 |
| 10292 | 1277 (EGFR) | 1.5E+06 | 4.8E−04 | 3.2E−10 | 7.9E+05 | 2.7E−04 | 3.5E−10 |
| 10460 | 1277A (EGFR) | 1.3E+06 | 5.3E−04 | 4.1E−10 | 9.7E+05 | 5.2E−04 | 5.3E−10 |
| 11294 | 1277A (EGER) | 3.4E+05 | 1.8E−04 | 5.3E−10 | 3.7E+05 | 2.1E−04 | 5.6E−10 |
| 1565 | chimeric (EGFR) | 1.7E+06 | 5.8E−04 | 3.5E−10 | 5.8E+05 | 1.6E−02 | 2.8E−08 |
| 10560 | 1565 (EGFR) | 1.7E+06 | 4.6E−04 | 2.7E−10 | 8.9E+05 | 2.7E−03 | 3.1E−09 |
| 11302 | 1565 (EGFR) | 4.9E+05 | 9.6E−05 | 2.0E−10 | 4.2E+05 | 4.9E−04 | 1.2E−09 |

TABLE 6-continued

Binding affinity of chimeric parent antibodies and humanized antibodies

| Ab ID | Source library (specificity) | Human antigen | | | Cynomolgus antigen | | |
|---|---|---|---|---|---|---|---|
| | | $k_a$ (M$^{-1}$s$^{-1}$) | $k_d$ (s$^{-1}$) | $K_D$ (M) | $k_a$ (M$^{-1}$s$^{-1}$) | $k_d$ (s$^{-1}$) | $K_D$ (M) |
| 4384 | chimeric (HER2) | 4.0E+05 | 3.0E−04 | 7.5E−10 | 1.8E+05 | 5.0E−04 | 2.9E−09 |
| 10704 | 4384 (HER2) | 3.6E+05 | 1.4E−04 | 3.9E−10 | 1.9E+05 | 2.7E−04 | 1.4E−09 |
| 11249 | 4384 (HER2) | 2.2E+05 | 1.1E−04 | 5.0E−10 | 1.5E+05 | 3.8E−04 | 2.5E−09 |
| 4517 | chimeric (HER2) | 2.6E+05 | 2.9E−04 | 1.1E−09 | 2.3E+05 | 8.6E−04 | 3.7E−09 |
| 11145 | 4517 (HER2) | 1.27E+05 | 1.24E−04 | 9.8E−10 | 5.3E+04 | 6.3E−04 | 1.2E−08 |
| 5038 | chimeric (HER3) | 3.0E+05 | 4.8E−04 | 1.6E−09 | 4.6E+05 | 4.1E−04 | 8.9E−10 |
| 10738 | 5038 (HER3) | 2.6E+05 | 1.9E−04 | 7.5E−10 | 5.4E+05 | 2.9E−04 | 5.4E−10 |
| 10810 | 5038 (HER3) | 1.9E+05 | 2.0E−04 | 1.1E−09 | 4.7E+05 | 3.4E−04 | 7.1E−10 |
| 5082 | chimeric (HER3) | 9.1E+05 | 7.3E−05 | 8.0E−11 | 1.7E+06 | 1.6E−04 | 9.8E−11 |
| 11006 | 5082 (HER3) | 7.4E+05 | <2E−6 | ND* | 1.5E+06 | 8.7E−05 | 5.9E−11 |
| 11052 | 5082 (HER3) | 8.7E+05 | 1.6E−04 | 1.8E−10 | 1.3E+06 | 2.6E−04 | 1.9E−10 |

*KD could not be determined due to a very slow off-rate. Estimated to be in the picomolar range.

In Vitro Functional Evaluation of Humanized Variants

Humanized antibody variants were tested for functional effect in a viability assay in combination with a chimeric "partner antibody" in an antibody mixture containing two antibodies against different epitopes of a particular target (where "partner antibody" refers to the fact that antibody 1277 variants (anti-EGFR) were tested together with the chimeric anti-EGFR antibody 1565, antibody 4:384 variants (anti-HER2) were tested in combination with the chimeric anti-HER2 antibody 4517, and so forth) to determine if the functional synergy between the two antibodies targeting the same receptor was preserved after humanization. Each humanized variant was tested in two cell lines and compared to the parental mixture of two chimeric antibodies and to a negative control antibody. The cell lines used were selected on the basis of their previously determined receptor-dependency, i.e., A431NS epidermoid, H358 non-small cell lung, and FaDu head and neck cancers for EGFR, OE19 esophageal and BT474 breast cancer for HER2, and MDA-MB-175 VII and MCF-7 breast cancer for HER3. In addition, a combination of six humanized variants (11294, 11302, 11249, 11145, 10738 and 11052; Humanized Pan-HER) was tested in a number of cell lines and compared to the combination of the six chimeric antibodies (1277, 1555, 4384, 4517, 5038 and 5082; Chimeric Pan-HER). The cell lines used, N87 gastric, FaDu head and neck, A431NS epidermoid, OE19 esophageal, HN5 head and neck, MDA-MB-175 VII breast and MFE-280 endometrial cancer, were selected on the basis of their previously determined dependency on the HER family receptors.

Prior to performing the viability assay the appropriate antibodies and antibody mixtures were diluted to a final total antibody concentration of 100 µg/ml in appropriate media supplemented with 0.5-2% FBS and 1% P/S (penicillin/streptomycin), yielding a final total antibody concentration of 50 µg/ml in the well containing the highest antibody concentration. A threefold serial dilution of the antibodies was then performed in a 384-well plate, followed by addition of relevant numbers of cells to the experimental wells. The MCF-7 cells were also stimulated with 1 nM heregulin beta. The plates were incubated for 4 days in a humidified incubator at 37° C. WST-1 reagent (Roche Applied Science, Mannheim, Germany) was added to the plates and the plates were incubated for 1-3 h at 37° C. Plates were transferred to an orbital plate shaker for one h and the absorbance was measured at 450 and 620 nm (reference wavelength) using an ELISA reader. The percentage of metabolically active cells (MAC) is calculated as a percentage of the untreated control as follows:

$$\% \ MAC = \left( \frac{(OD\text{exp.} - OD\text{medium})}{(OD\text{untreat.} - OD\text{medium})} \right) \times 100$$

The in vitro activity of selected humanized antibody variants is shown in FIGS. 7-15 and 17-19. The results show that all of the selected humanized variants display an antiproliferative effect when combined with their chimeric or humanized partner that is very similar to the effect of the relevant mixture of the two chimeric parent antibodies. Furthermore, the combination of six humanized variants also displays an effect very similar to the effect of the combination of the six chimeric parent antibodies (FIG. 20).

Specificity of Humanized Variants (Cross-Ractivity)

The chimeric parent antibodies and selected humanized variants were tested for binding to EGFR, HER2 and HER3 from humans, cynomolgus monkeys and mice, as well as human and murine HER4, to determine whether the humanization had introduced any changes in the cross-reactivity pattern.

Antibody-antigen binding was measured by ELISA with coated antigens. Human antigens were obtained from Sino Biologicals. All other antigens were produced in-house by transient expression in CHO or HEK293 cells. Chimeric and humanized antibodies, as well as an isotype control antibody, were incubated with the coated antigens at different concentrations. After wash, bound antibodies were detected by HRP—(horse radish peroxidase)-conjugated secondary antibodies. The OD signal from 40 nM antibody, measured at 450 nm using an ELISA reader, was scored from negative (−; OD<0.1) to strongly positive (+++; OD>2.5).

The results, shown in the table in FIG. 16, demonstrate that cross-reactivity between the respective human and cynomolgus antigens is conserved in all humanized antibody variants, and that no new reactivity to members of the epidermal growth factor receptor family has been introduced.

Summary and Conclusions

A number of humanized variants of the chimeric anti-EGFR, anti-HER2 and anti-HER3 antibodies disclosed in PCT/IB2011/054834 were produced by screening of CDR-grafted libraries generated by back mutation of potentially critical framework positions and in some cases by alteration of unwanted CDR sequence motifs. Approximately 100 hits from each library selected for binding affinity to the relevant target antigen were subjected to off-rate ranking, and variants with a dissociation rate similar to or slower than that of the parent chimeric antibody were selected and sequenced. Between four and ten hits from each library screening were selected on the basis of retained or improved binding to human and cynomolgus antigen, number of back-mutations and absence of unwanted sequence motifs for larger scale expression and purification. Selected purified humanized antibody variants were subjected to a kinetic binding analysis to determine binding affinity to human and cynomolgus antigen, to in vitro functional analysis in a viability assay in combination with a chimeric partner antibody binding to a different epitope of the same receptor, and to a cross-reactivity assay.

Each of the humanized variant antibodies 10292, 10460, 11294, 10560, 11302, 10704, 112449, 11145, 10738, 10810, 11006 and 11052 were found to exhibit functional properties that were very similar to those of the original chimeric parent antibody from which they were derived, including:
  similar or higher binding affinity;
  similar or slower dissociation rate;
  binding to the same human and cynomolgus antigen combined with lack of binding to the mouse antigen or to other EGFR family receptors; and
  highly similar anti-proliferative effects in two different cell lines when tested in a functional in vitro assay in combination with the chimeric partner antibody.

These results thus demonstrate that the humanized antibody variants of the invention have functional characteristics that are highly similar to the respective parent chimeric antibodies from which they are derived. This strongly suggests that mixtures of the humanized antibodies of the invention, e.g. mixtures containing one or two such antibodies against each of the EGFR family receptors EGFR, HER2 and HER3, can be expected to demonstrate anti-cancer effects in vivo that are similar to the effects of the mixtures of the parent chimeric antibodies described in PCT/IB2011/054834.

Figure 21A:
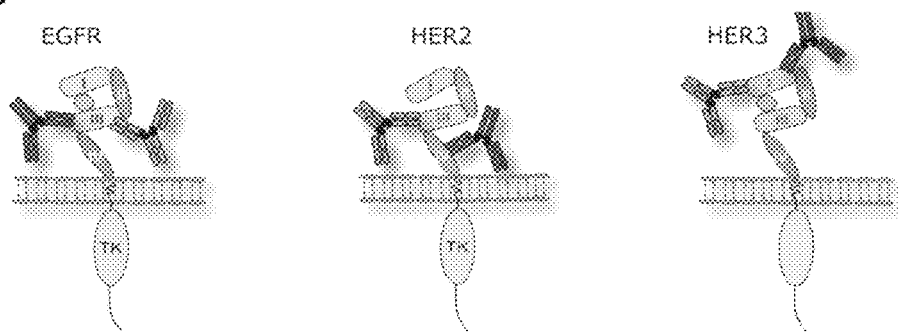
FIG. 21A is a schematic illustrating the interaction of Pan-HER with its EGFR (left), HER2 (middle) and HER3 (right) target proteins.

Example 2: Two Monoclonal Antibodies Against Non-Overlapping Epitopes on EGFR, HER2 or HER3 Display Synergistic in Vitro Growth Inhibitory Activity and Effectively Induce Target Down-Regulation Antibodies against non-overlapping epitopes on EGFR (i.e., 1277 and 1565), HER2 (i.e., 4384 and 4517), and HER3 (i.e., 5038 and 5082) as illustrated in FIG. 21A, were tested for their ability to inhibit the growth and proliferation of the cancer cell lines A431NS, HCC202, and MDA-MB-175-VII, respectively, using a viability assay. Antibody treatments consisted of antibodies to each receptor administered either alone or in the following combinations: 1277 and 1565 mixture, 4384 and 4517 mixture, and 5038 and 5082 mixture. Cellular damage will inevitably result in loss of the ability of the cell to maintain and provide energy for metabolic cell function and growth. Metabolic activity assays are based on this premise and usually measure mitochondrial activity. The Cell Proliferation Reagent WST-1 (Roche Cat. No 11 644 807 001) is a ready-to-use substrate that measures the metabolic activity of viable cells. It is assumed that the metabolic activity correlates with the number of viable cells. In this example, the WST-1 assay was used to measure the number of metabolically active cells after treatment of cancer cells with different concentrations of antibodies for 96 hours.

Prior to performing the WST-1 assay, the appropriate antibodies and antibody mixes were diluted to a final total antibody concentration of 100 µg/ml in appropriate media supplemented with 2% of FBS and 1% P/S yielding a final total antibody concentration of 50 µg/ml in the well containing the highest antibody concentration. A threefold serial dilution of the antibodies was then performed. Relevant numbers of cells were then added to the experimental wells in a 384-well plate. The plates were incubated for 4 days in a humidified incubator at 37° C. WST-1 reagent was then added to the plates and the plates were incubated for one hour at 37° C., Plates were transferred to an orbital plate shaker for one hour and the absorbance was measured at 450 and 620 nm (reference wavelength) using an EISA reader. The amount of metabolically active cells (MAC) is calculated as a percentage of the untreated control as follows:

$$\% \ MAC = \left(\frac{(ODexp. - ODmedia)}{(ODuntreat. - ODmedia)}\right) \times 100$$

Figure 21B:
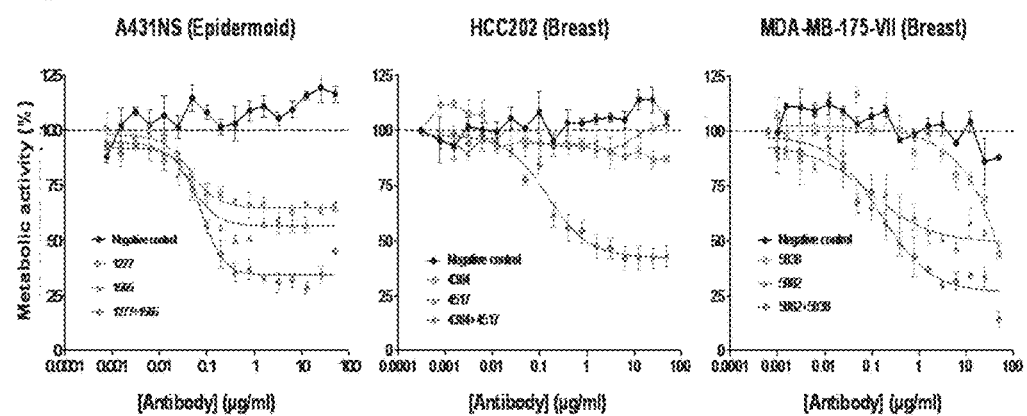
FIG. 21B is a series of charts showing the effects of treatment with EGFR (left), HER2 (middle) and HER3 (right) antibodies on the metabolic activity of A431N5, HCC202, and MDA-MB-175-VII cell lines, respectively. The figure legend in the left panel lists from top to bottom: Negative control, 1277, 1565, 1277+1565. The figure legend in the center panel lists from top to bottom: Negative control, 4384, 4517, 4384+4517. The figure legend in the right panel lists from top to bottom: Negative control, 5038, 5082, 5038+5082.
Figure 21C:
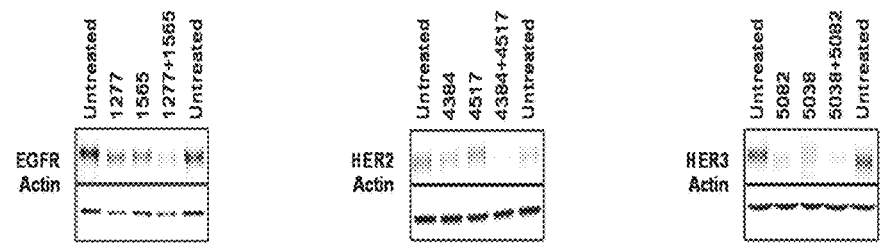
FIG. 21C is a series of Western blot images showing the levels EGFR (left), HER2 (middle), and HER3 (right) in the total cell lysates of A431NS, HCC202 and MDA-MB-175-VII cancer cells, respectively, that had been treated with the indicated antibodies and antibody mixtures.

The in vitro effects of antibody treatment showed that mixtures of antibodies are superior to the individual antibodies to each of the three HER receptors tested (FIG. 21B). Furthermore, analysis of EGFR, HER2 and HER3 levels in cell lysates isolated from antibody treated A431NS, HCC202 and MDA-MB-175-VII cells (20 µg/ml total antibody for each treatment for 48 hours) by Western Blot analysis showed that antibody treated cells exhibited reduced levels of EGFR, HER2 and HER3 compared to untreated cells (FIG. 21C).

This example demonstrates that two antibodies against EGFR, HER2 or HER3 display synergistic in vitro growth inhibitory activity and effectively induce target down-regulation.

Figure 22:
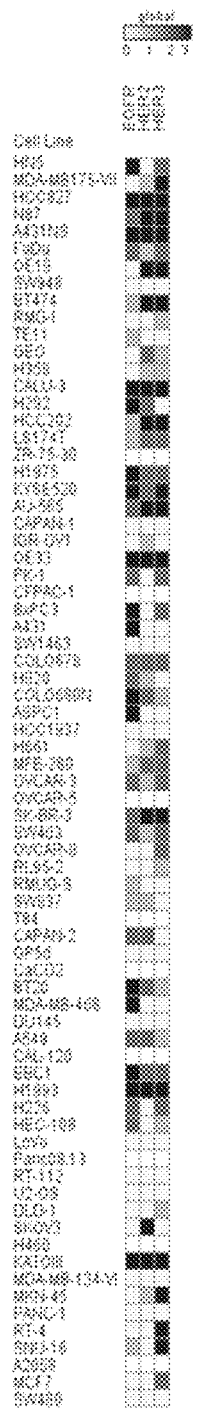
FIG. 22 is an image showing the receptor phosphorylation levels of EGFR (left), HER2 (middle), and HER3 (right) in 73 cancer cell lines treated with Pan-HER (1277, 1565, 4384, 4517, 5038 and 5082; chimeric Pan-HER).

Example 3: Pan-HER is Broadly Inhibitory in a Large Number of Cell Lines of Different Tissue Origin and Genetic Background Mixtures of antibodies against non-overlapping epitopes on EGFR, HER2, and/or HER3 were tested for their ability to inhibit the growth and proliferation of a broad range of cancer cell lines. The effects of treatment with Pan-HER (a mixture of six monoclonal antibodies against EGFR, HER2 and HER3; antibodies 1277, 1565, 4384, 4517, 5038, and 5082), antibody mixtures targeting two HER family members (i.e., EGFR and HER2, EGFR and HER3, and HER2 and HER3), and antibody mixtures targeting one HER family member (i.e., EGFR, HER2 and HER3) were measured in the following cell lines: HN5, MDA-MB175-VII, HCC827, N87, A431NS, FaDu, OE19, SW948, BT474, RMG-1, TE11, GEO, H358, CALU-3, H292, HCC202, LS174T, ZR-75-30, H1975, KYSE520, AU-565, CAPAN-1, IGR-OV1, OE33, PK-1, CFPAC-1, BxPC3, A431, SW1463, COL0678, H820, COL0680N, ASPC1, HCC1937, H661, MFE-280, OVCAR-3, OVCAR-5, SK-BR-3, SW403, OVCAR-8, RL95-2, RMUG-S, SW837, T84, CAPAN-2, GP5d, CaCO2, BT20, MDA-MB-468, DU145, A549, CAL- 120, EBC1, H11993, H226, HEC-108, LoVo, Panc08.13, RT-112, U2-OS, DLD-1, SKOV3, H460, KATOIII, MDA-MB-134-VI, MKN-45, PANC-1, RT-4, SNU-16, A2058, MCF7, SW480. Characterization of the receptor phosphorylation levels of EGFR, HER2 and HER3 in these 73 cell lines using PathScan RTK Signaling Antibody Arrays (Cell Signaling Technology) demonstrated elevated HER family activation (FIG. 22).

Effects of antibody treatments in over 70 cancer cell lines (out of more than 100 cell lines tested) on metabolic activity were determined after 96 hours incubation using a similar WST-1 assay as described in Example 2. Results showed that Pan-HER is broadly inhibitory in a large number of cancer cell lines of different tissue origin and genetic background in the presence of Heregulin (FIG. 24), EGF (FIG. 25), or neither ligand (FIG. 23), "EGFR" refers to a mixture of antibodies 1277 and 1565. "HER2" refers to a mixture of antibodies 4384 and 4517, "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 50:38, and 5082. "HER2+HER3" refers to a mixture of antibodies 4384, 4517, 5038, and 5082, "Pan-HER" refers to a mixture of antibodies 1277, 1565, 4384, 4517, 5038, and 5082. These results further demonstrated that simultaneous targeting of three receptors provided broader efficacy than targeting of a single receptor or any combination of two receptors in the HER family.

Example 4: Pan-HER Effectively Inhibits Ligand-Induced Proliferation

Figure 26:
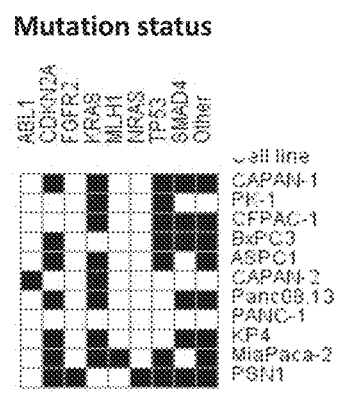
FIG. 26 is an image showing the mutation status of genes listed across the top of the image of seven pancreatic cancer cell lines (CAPAN-1, PK-1, CFPAC-1, BxPC3, ASPC1, CAPAN-2, Pan08.13, PANC-1, KP4, MiaPaca-2 and PSN1).
Figure 27:
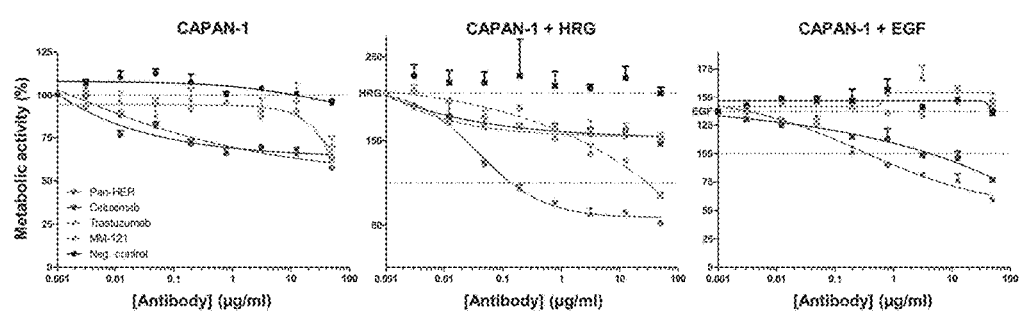
FIG. 27 is a series of graphs showing the dose-response of the CAPAN-1 cell line to Pan-HER treatment in the absence (left) or presence of Heregulin (middle) and EGF (right) ligands. "Pan-HER" refers to a mixture of antibodies 1277, 1565, 4384, 4517, 5038, and 5082.

To determine if antibody mixtures are efficacious in the presence of EGFR and HER3 ligands, antibodies mixtures against one, two or three HER family receptors were tested for their ability to inhibit the growth and proliferation of pancreatic cancer cell lines in the presence of Heregulin, EGF, or neither ligand. The effects of treatment with Pan-HER (a mixture of six monoclonal antibodies against EGFR, HER2 and HER3; antibodies 1277, 1565, 4384, 4517, 5038, and 5082), antibody mixtures targeting two HER family members (i.e., EGFR and HER2, EGFR and HER3, and HER2 and HER3), and antibody mixtures targeting one HER family member (i.e., EGFR, HER2 and HER3) were measured on the following cell lines: CAPAN-1, PK-1, CFPAC-1, BxPC 3, ASPC1, CAPAN-2, Panc08.13, PANC-1, KP4, MiaPaca-2 and PSN1). The mutation status of these cell lines is shown in FIG. 26. The ability of antibodies mixtures against one, two or three HER family receptors to inhibit the growth and proliferation of a wide variety of cancer cell lines in the presence of Heregulin, EGF, or neither ligand was also tested (FIGS. 23-25). Cells were exposed to medium containing antibodies and ligands for 96 hours (ligand and antibody were added simultaneously to the cells). Metabolic activity was determined after 96 hours incubation using a similar WST-1 assay as described in Example 2. "EGFR" refers to a mixture of antibodies 1277 and 1565. "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 5038, and 5082. "HER2+HER3" refers to a mixture of antibodies 4384, 4517, 5038, and 5082. Pan-Her exhibited effective inhibition of a wide variety of cancer cell lines in the presence of EGF or Heregulin.

Example 5: Pan-HER Maintains Inhibitory Effect in Cells with Acquired Resistance to Approved Therapeutic Antibodies Pan-HER (a mixture of six monoclonal antibodies against EGFR, HER2 and HER3; antibodies 1277, 1565, 4384, 4517, 5038, and 5082) was tested for its ability to inhibit the growth and proliferation of FINS, OE19 and MDA-MB-175-VII cell lines or cell pools with acquired resistance to cetuximab, trastuzumab, or pertuzumab, respectively. Cetuximab resistant HN5 cell lines were generated as described in Example 11. Trastuzumab resistant OE19 cells and pertuzumab resistant MDA-MB-175-VII cells were established by exposing parental cells to increasing concentrations of trastuzumab [10-10 µg/ml] and pertuzumab [1-50 µg/ml] respectively, during a period of eight months and 12 months respectively. Cells were split once or twice a week in order to keep cells in expotential growth. The level of resistance was tested every month in a WST-1 viability assay as described in Example 2, until a pool of resistant cells was established. Single cell clones of trastuzumab resistant OE19 cells were generated through limited dilution cloning of the acquired trastuzumab resistant pool of OE19 cells as described in Example 11.

Figure 28:
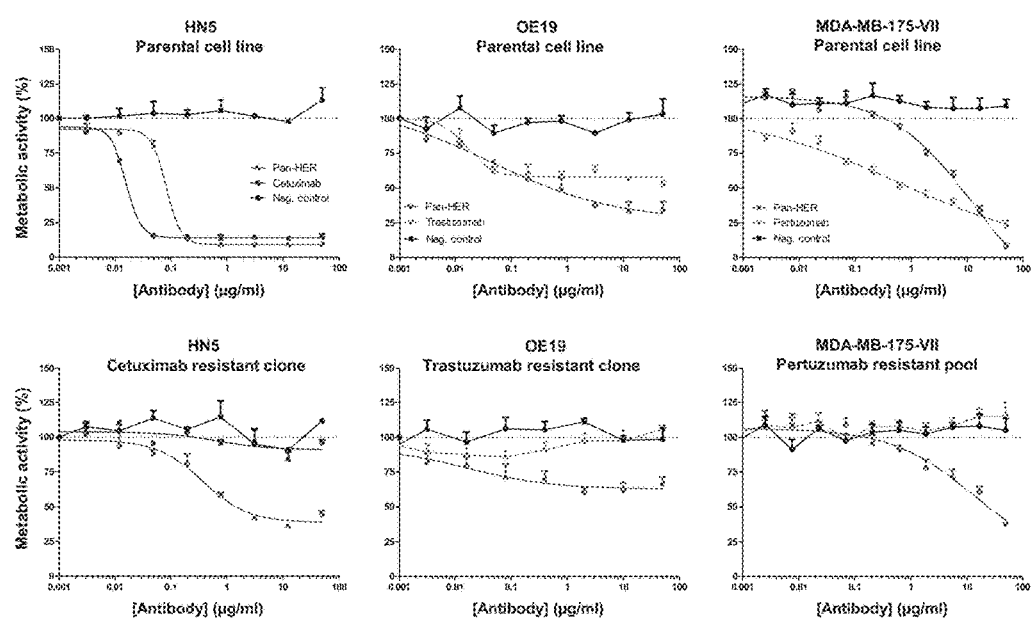
FIG. 28 is a series of graphs showing the effects of Pan-HER and reference antibodies on the metabolic activity of parental cell lines (top) and the corresponding resistant clones that have acquired resistance to cetuximab, trastuzumab or pertuzumab (bottom). "Pan-HER" refers to a mixture of antibodies 1277, 1565, 4384, 4517, 5038, and 5082. The figure legend in the left top panel lists from top to bottom: Pan-HER, cetuximab, Neg. control. The figure legend in the center top panel lists from top to bottom: Pan-HER, trastuzumab, Neg. control. The figure legend in the right top panel lists from top to bottom: Pan-HER, pertuzumab, Neg. control.

Metabolic activity was determined after 96 hours incubation using a similar WST-1 assay as described in Example 2. Pan-HER-treated resistant cells as well as parental cells exhibited reduced levels of metabolic activity (FIG. 28). In contrast, metabolic activity was reduced in parental HN5, OE19 and MDA-MB-175-VII cells, but unaltered in resistant clones treated with cetuximab, trastuzumab, or pertuzumab, respectively. This example demonstrates that Pan-HER maintains inhibitory effect in cells with acquired resistance to approved therapeutic antibodies.

Figure 29:
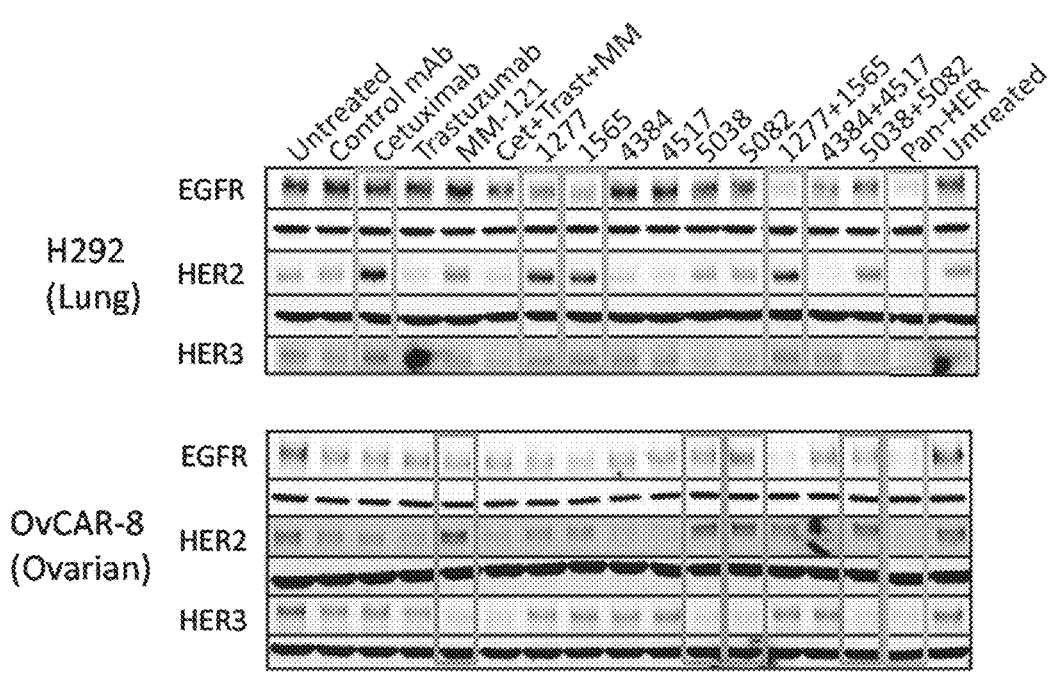
FIG. 29 is a series of Western blot images showing the levels of EGFR, HER2 and HER3 in whole cell lysates of H292 (top) and OVCAR-8 (bottom) cell lines after antibody treatment. "Pan-HER" refers to a mixture of antibodies 1277, 1565, 4384, 4517, 5038, and 5082.

Example 6: Pan-HER Effectively Prevents Compensatory Receptor Up-Regulation in Vitro To determine if compensatory receptor up-regulation occurs as a result of treatment with antibody mixtures of the present invention, EGFR, HER2 and HER3 levels were measured in whole cell lysates from H292 and OVCAR8 cell lines after antibody treatment (20 µg/ml) for 48 hour by western blot analysis. The effects of treatment with Pan-HER (a mixture of six monoclonal antibodies against EGFR, HER2 and HER3; antibodies 1277, 1565, 4384, 4517, 5038, and 5082) and antibody mixtures targeting one HER family member (i.e., EGFR (antibodies 1277, 1565, or 1277+1565), HER2 (antibodies 4384, 4517, or 4384+4517) and HER3 (antibodies 5038, 5082, or 5038+5082)) were determined. β-Actin was used as a loading control. Results showed that anti-EGFR treatment lead to HER2 upregulation in H292 cells (FIG. 29, top; cetuximab lane, 1277, 1565, and 1277+1565 lanes), and anti-HER3 treatment lead to HER2 up-regulation in OVCAR-8 (FIG. 29, bottom; MM-121 lane, 5038, 5082, and 5038+5082 lanes), while Pan-HER treatment lead to the downregulation of EGFR, HER2 and HER3 (FIG. 29; Pan-Her lanes). These results demonstrated that Pan-HER effectively induced simultaneous down-regulation of all three targets and prevented compensatory receptor up-regulation, a potential mechanism for acquiring resistance.

Example 7: Synergistic Effect of Targeting Multiple HER Family Receptors in BxPC-3 (Pancreatic Cancer) Xenograft Model To evaluate the efficacy of antibody mixtures against EGFR, HER2, HER3 and combinations of two and three receptor targets in xenograft model of human cancer, BxPC-3 (pancreatic cancer) xenograft models were treated with antibody mixtures and the effect on tumor size assayed.

In this assay, BxPC-3 pancreatic cancer cells were inoculated into mice. In brief, 5×106 BxPC3 cells were inoculated subcutaneously into the left flank of eight to ten week old female athymic nude mice. Tumors were measured thrice weekly with calipers and tumor volume in mm3 was calculated according to the formula: (width)$^2$×length×0.5. At an average tumor size of 140 mm$^3$ the mice were randomized and treatment initiated. The mice were treated with thrice weekly intraperitoneal injections of 50 mg/kg (10 injections in total) followed by an observation period. Graphical representations of tumor volume data were presented as means±SEM.

Figure 30:
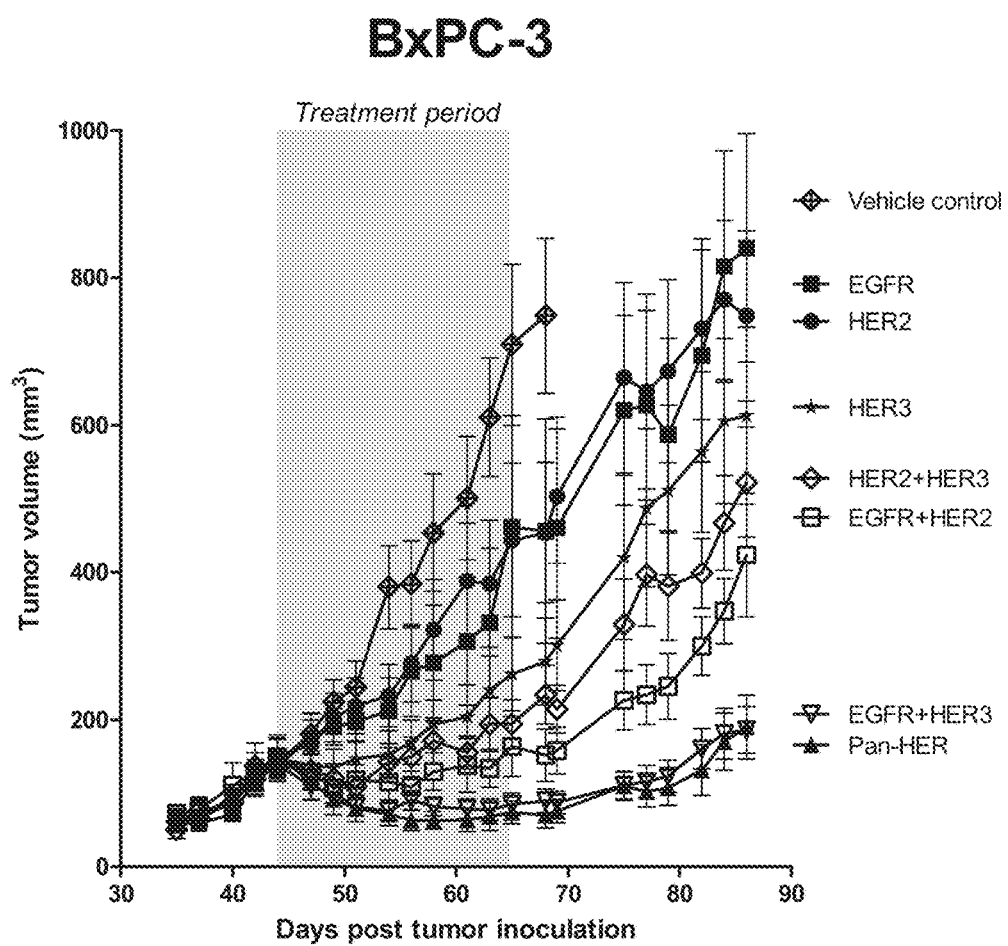
FIG. 30 is a graph showing the effects of treatment with Pan-HER or its subcomponents on tumor volume in the BxPC-3 xenograft model. "Pan-HER" refers to a mixture of antibodies 1277, 1565, 4384, 4517, 5038, and 5082. "EGFR" refers to a mixture of antibodies 1277 and 1565. "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 5038, and 5082. "HER2+HER3" refers to a mixture of antibodies 4384, 4517, 5038, and 5082.
Figure 31:
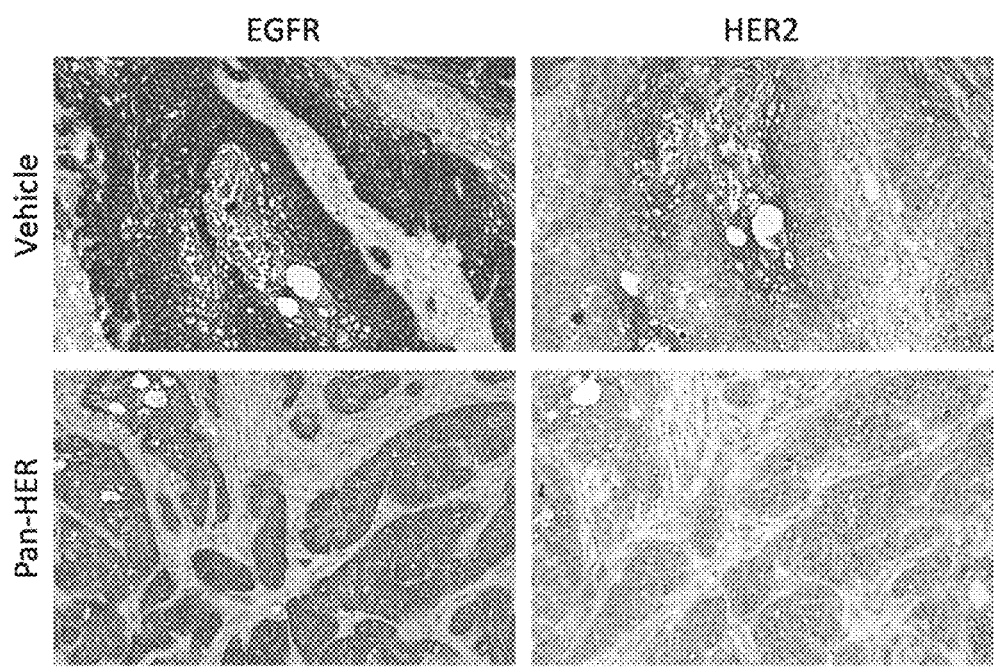
FIG. 31 is a series of images showing EGFR and HER2 immunolabeled sections of tumors resected from vehicle and Pan-HER treated BxPC-3 xenografts three days after withdrawal of treatment. "Pan-HER" refers to a mixture of antibodies 1277, 1565, 4384, 4517, 5038, and 5082.

Results showed that Pan-HER (antibodies 1277, 1565, 4384, 4517, 5038, and 5082) effectively suppressed tumor growth in the BxPC-3 xenograft model (FIG. 30; N=7/group; treatment period indicated by the light grey area on the graph). A clear synergy was observed when targeting EGFR and HER3 as well as EGFR and HER2, with the former combination being most efficient at controlling growth of the BxPC3 tumor xenografts. "EGFR" refers to a mixture of antibodies 1277 and 1565, "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 5038, and 5082. "HER2+HER3" refers to a mixture of antibodies 4384, 4517, 5038, and 5082. "Pan-HER" refers to a mixture of antibodies 1277, 1565, 4384, 4517, 5038, and 5082. Furthermore, EGFR and HER2 down-regulation by Pan-HER in vivo was confirmed by immunohistochemistry on tissue sections from tumors resected 3 days after withdrawal of treatment (FIG. 31).

Example 8: Synergistic Effect of Targeting Multiple HER Family Receptors in Calu-3 (NSCLC) Xenograft Model To evaluate the efficacy of antibody mixtures against EGFR, HER2, HER3 and combinations of two and three receptor targets in xenograft models of human cancer, the Calu-3 (NSCLC) xenograft model were treated with antibody mixtures and the effect on tumor size assayed. In this assay, Calu-3 NSCLC cells were inoculated into mice. In brief, 1×107 Calu-3 cells were inoculated subcutaneously into the left flank of eight to ten week old female athymic nude mice. Tumors were measured thrice weekly with calipers and tumor volume in mm3 was calculated according to the formula: (width)2×length×0.5. At an average tumor size of 170 mm3 the mice were randomized and treatment initiated. The mice were treated with thrice weekly intraperitoneal injections of 50 mg/kg (8 injections in total). Graphical representations of tumor volume data were presented as means±SEM.

Figure 32:
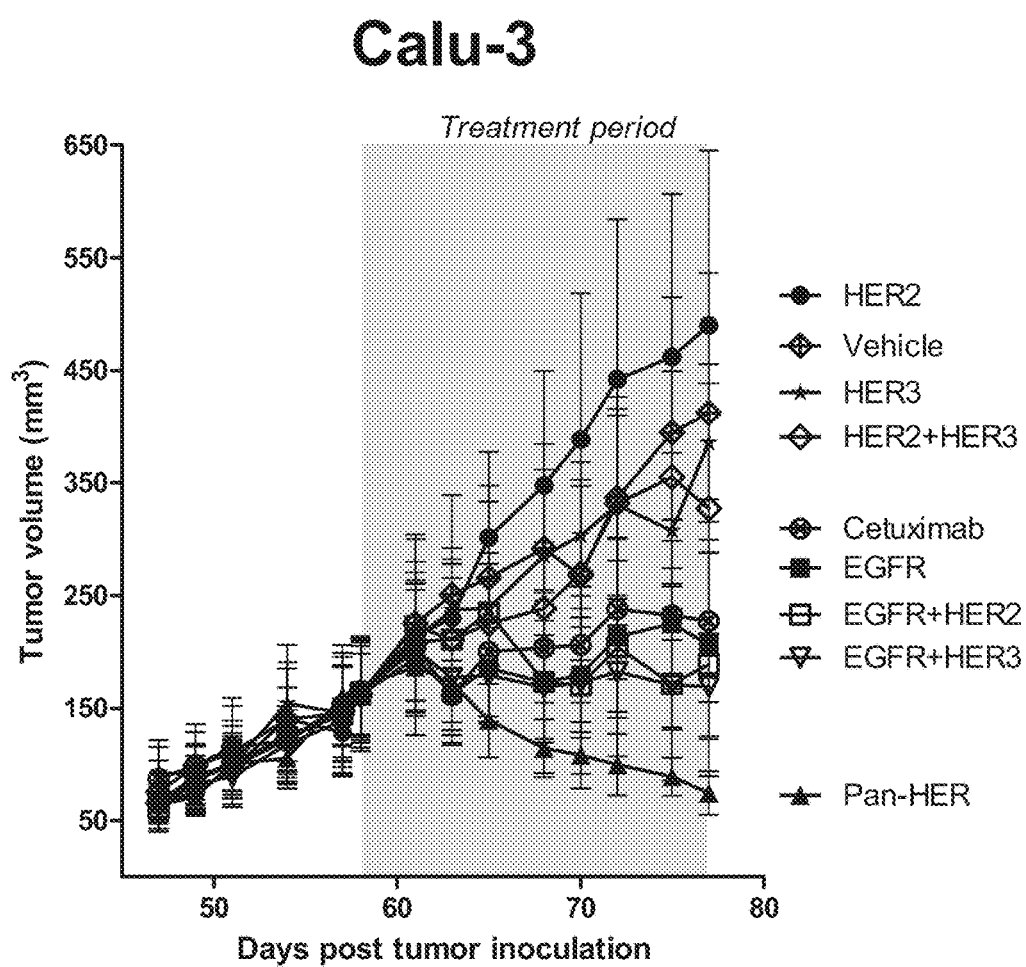
FIG. 32 is a graph showing the effects of treatment with Pan-HER or its subcomponents on tumor volume in the Calu-3 xenograft model. "Pan-HER" refers to a mixture of antibodies 1277, 1565, 4384, 4517, 5038, and 5082. "EGFR" refers to a mixture of antibodies 1277 and 1565. "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1555, 5038, and 5082. "HER2+HER3" refers to a mixture of antibodies 4384, 4517, 5038, and 5082.

Results showed that Pan-HER (antibodies 1277, 1565, 4384, 4517, 5038, and 5082) effectively suppressed tumor growth in the Calu-3 xenograft model (FIG. 32; N=5/group; treatment period indicated by the light grey area on the graph). The results show a synergistic effect of targeting EGFR, HER2 and HER3 simultaneously whereas no clear synergy could be observed when targeting EGFR and HER2 or EGFR and HER3 compared to the anti-tumor response of EGFR mono-targeting, "EGFR" refers to a mixture of antibodies 1277 and 1565. "HER2" refers to a mixture of antibodies 4:384 and 4517. "HER3" refers to a mixture of antibodies 5038 and 5082. "EGFR+HER2" refers to a mixture of antibodies 1277, 1565, 4384, and 4517, "EGFR+HER3" refers to a mixture of antibodies 1277, 1555, 5038, and 5082. "HER2+HER3" refers to a mixture of antibodies 4384, 4517, 5038, and 5082. "Pan-HER" refers to a mixture of antibodies 1277, 1565, 4384, 4517, 5038, and 5082.

Figure 33:
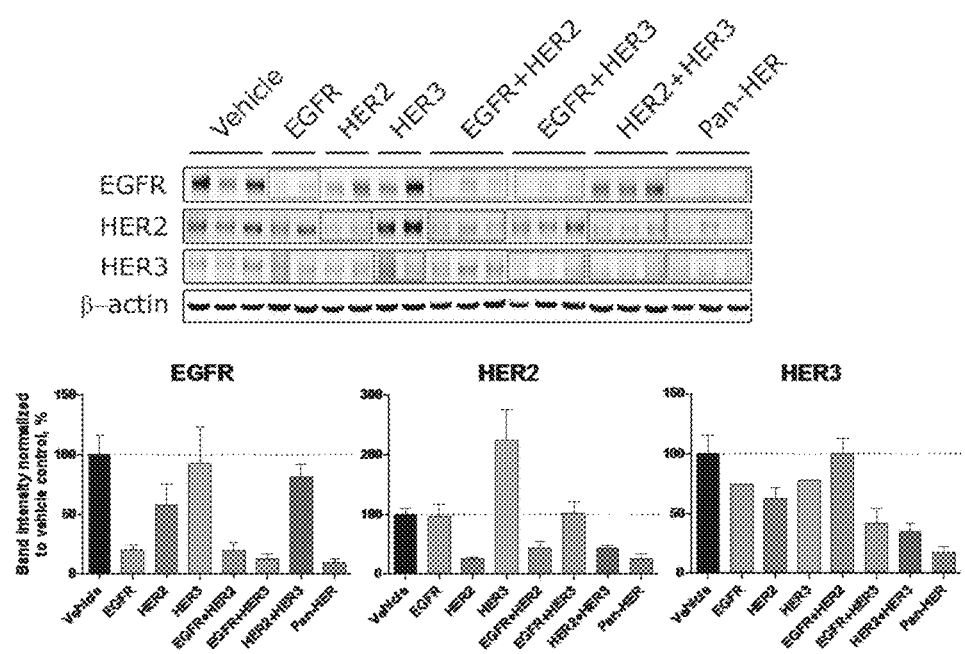
FIG. 33 (top) is a series of Western blot images showing the levels of EGFR, HER2, HER3 and a β-actin loading control in BxPC-3 tumor lysates after antibody treatment. The relative quantification of EGFR, HER2, and HER3 levels in the Western blot band intensities is shown in a series of charts (bottom), "Pan-HER" refers to a mixture of antibodies 1277, 1565, 4384, 4517, 5038, and 5082, "EGFR" refers to a mixture of antibodies 1277 and 1565, "HER2" refers to a mixture of antibodies 4384 and 4517, "HER3" refers to a mixture of antibodies 5038 and 5082, "EGFR+HER2" refers to a mixture of antibodies 1277, 1565, 4384, and 4517, "EGFR+HER3" refers to a mixture of antibodies 1277, 1565, 5038, and 5082, "HER2+HER3" refers to a mixture of antibodies 4:384, 4517, 5038, and 5082.

Example 9: Pan-HER Effectively Prevents Compensatory Receptor Up-Regulation in Vivo To determine if prevention of compensatory receptor up-regulation occurs in vivo as a result of treatment with antibody mixtures of the present invention, EGFR, HER2 and HER3 levels were measured in antibody-treated BxPC-3 tumor lysates by Western Blot analysis. The effects of treatment with Pan-HER (a mixture of six monoclonal antibodies against EGFR, HER2 and HER3; antibodies 1277, 1565, 4384, 4517, 5038, and 5082), antibody mixtures targeting two HER family members (i.e., EGFR and HER2, EGFR and HER3, and HER2 and HER3), and antibody mixtures targeting one HER family member (i.e., EGFR, HER2 and HER3) were determined. β-Actin was used as a loading control. Results showed that anti-EGFR treatment lead to EGFR downregulation (FIG. 33 top), anti-HER2 treatment lead to HER2 downregulation (FIG. 33 top), and anti-HER3 treatment lead to HER3 downregulation (FIG. 33 top). Relative quantification of the Western blot band intensities showed that HER2 was significantly up-regulated in response to anti-HER3 treatment (FIG. 33; bottom). In contrast, Pan-HER treatment resulting in the simultaneous and effective downregulation of EGFR, HER2 and HER3 (FIG. 33 top; green boxes and FIG. 33 bottom). "EGFR" refers to a mixture of antibodies 1277 and 1565. "HER2" refers to a mixture of antibodies 4384 and 4517. "HER3" refers to a mixture of antibodies 5038 and 5082. "EGFR-HER2" refers to a mixture of antibodies 1277, 1565, 4384, and 4517. "EGFR-HER3" refers to a mixture of antibodies 1277, 1565, 5038, and 5082. "HER2+HER3" refers to a mixture of antibodies 4384, 4517, 5038, and 5082. "Pan-HER" refers to a mixture of antibodies 1277, 1565, 4384, 4517, 5038, and 5082.

This example demonstrated that Pan-HER is capable of effectively inducing simultaneous down-regulation of all three targets and preventing compensatory receptor up-regulation in vivo.

Example 10: Synergistic Effect of Targeting Multiple HER Family Receptors in Patient-Derived KRAS Mutated Pancreatic Tumor Xenograft Models To evaluate the in vivo efficacy of antibody mixtures against EGFR, HER2, HER3 and combinations of two and three receptor targets, patient-derived tumor xenograft models of KRAS mutated pancreatic cancer (START Discovery, San Antonio, Tex.) were treated with antibody mixtures and the effect on tumor size assayed.

In this assay, patient-derived pancreatic cancer cells were inoculated into mice. In brief, viable resected patient tumor material was implanted in immunocompromised mice and serially passaged in vivo. At a tumor volume of 100-200 mm3, animals were randomized into treatment and control groups and dosing was initiated. Dosing schedule: 50 mg/kg i.p, three times weekly. 10 doses in total (day 0-20), N=5/group. Data are presented as means±SEM. Asterix indicates first day with p<0.05. The statistically significant difference in treatment response between the groups was maintained throughout the study period.

Figure 34:
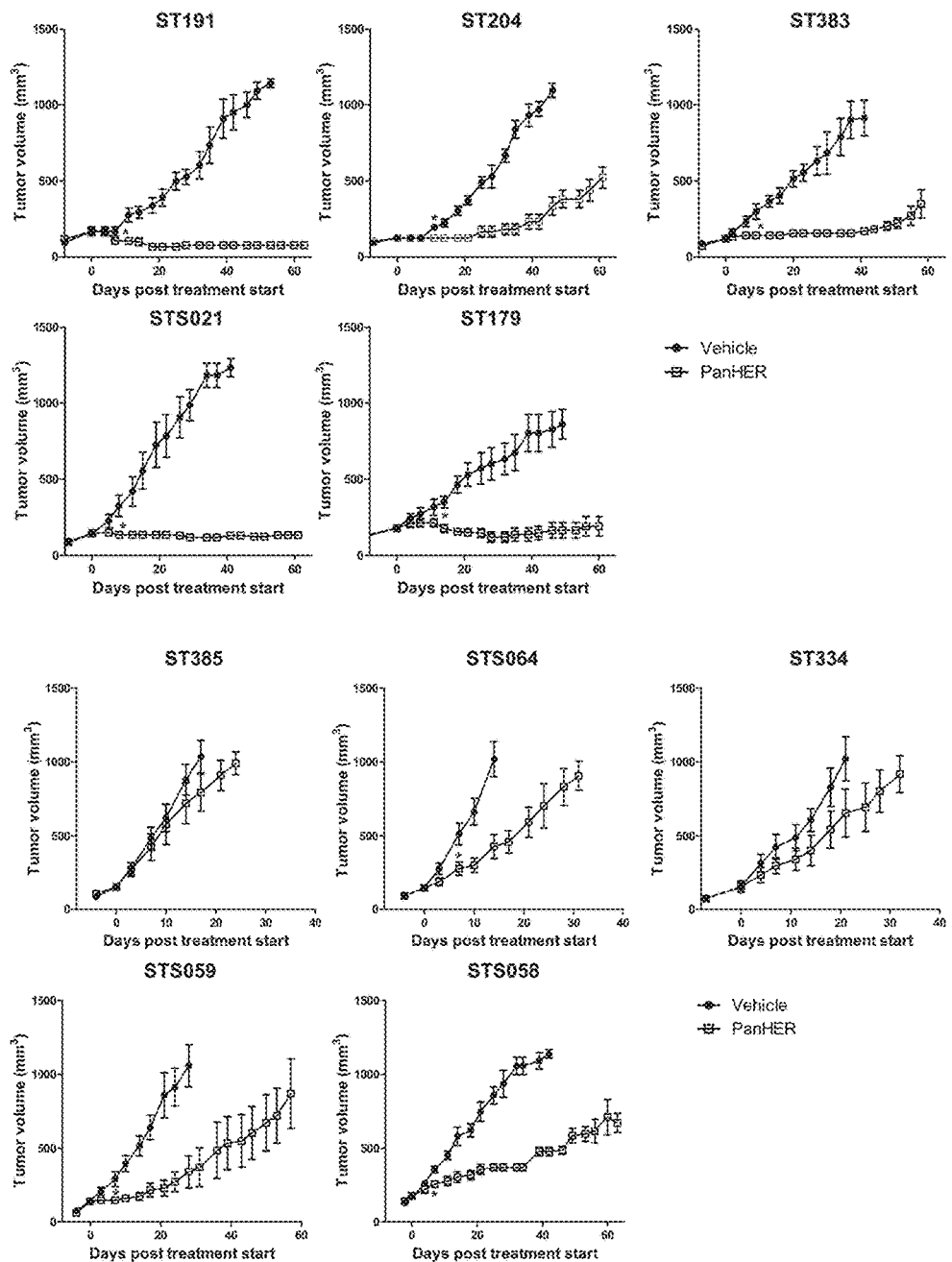
FIG. 34 is a series of graphs showing the effects of Pan-HER on tumor volume in ST191, ST204, ST383, STS021, ST179, ST385, ST5064, ST334, STS059, and STS058 patient-derived tumor xenograft models of KRAS mutated pancreatic cancer. "Pan-HER" refers to a mixture of antibodies 1277, 1565, 4384, 4517, 5038, and 5082.

Results showed that Pan-HER effectively suppressed tumor growth in hard-to-treat patient-derived models of pancreatic cancer. (FIG. 34; N=5/group). Furthermore, deconvolution studies revealed strong synergy of EGFR and HER2 targeting in the ST179 xenograft model and of EGFR and HER3, and to a lesser extent of EGFR and HER2, targeting in the ST383 xenograft model (FIG. 35; N=7-8/group; treatment period indicated by the light grey area on the graph). "EGFR" refers to a mixture of antibodies 1277 and 1565, "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 5038, and 5082. "HER2+HER3" refers to a mixture of antibodies 4384, 4517, 5038, and 5082. "Pan-HER" refers to a mixture of antibodies 1277, 1565, 4384, 4517, 5038, and 5082.

TABLE 7

Patient-derived xenograft models of pancreatic cancer

| Model | KRAS mut. | p53 mut. | Erlotinib resistant | Cet. resp. (20 mg/kg) | Other |
|---|---|---|---|---|---|
| ST383 | G12D | wt | Yes | ND | |
| ST204 | G12D | wt | ND | PD | |
| ST334 | G12D | R273C | Yes | PD | Trastuzumab resist. |
| ST385 | G12D | G245S | Yes | PD | |
| STS059 | G12D | K120R | Yes | ND | |
| STS058 | G12D | R273C | Yes | ND | |
| STS021 | G12R | wt | No | ND | |
| ST179 | G12V | wt | ND | ND | |
| STS064 | G12V | Y234C | ND | ND | |
| ST191 | G12S | wt | Yes | PD | | wt: wild-type, PD: Progressive disease, ND: Not determined.

Figure 35:
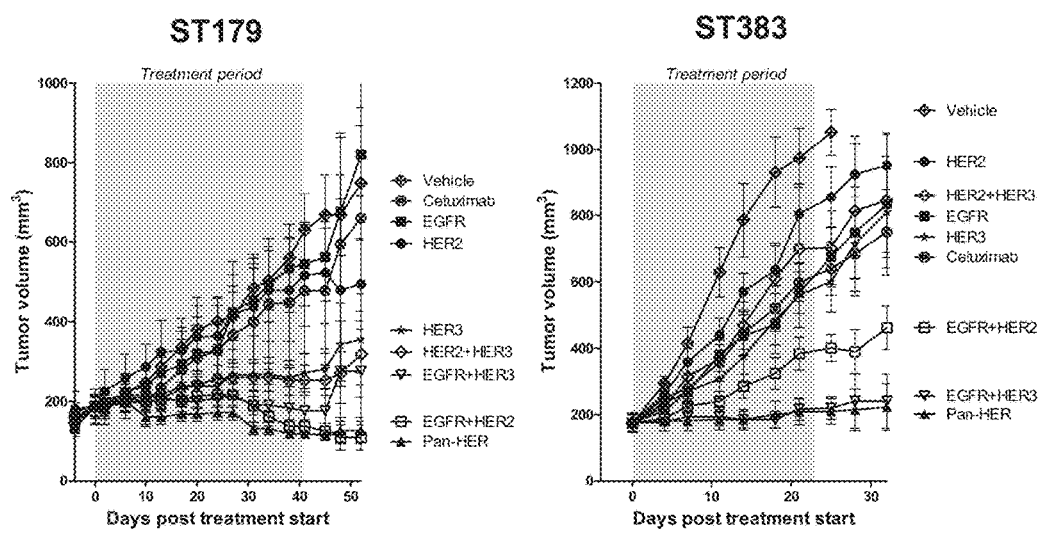
FIG. 35 is a series of graphs showing the effects of treatment with Pan-HER or its subcomponents on tumor volume in ST179 and ST383 patient-derived tumor xenograft models of KRAS mutated pancreatic cancer, "Pan-HER" refers to a mixture of antibodies 1277, 1565, 4384, 4517, 5038, and 5082. "EGFR" refers to a mixture of antibodies 1277 and 1565. "HER2" refers to a mixture of antibodies 4384 and 4517. "HER3" refers to a mixture of antibodies 5038 and 5082. "EGFR+HER2" refers to a mixture of antibodies 1277, 1565, 4384, and 4517. "EGFR+HER3" refers to a mixture of antibodies 1277, 1565, 5038, and 5082. "HER2+HER3" refers to a mixture of antibodies 4384, 4517, 5038, and 5082.
Figure 36:
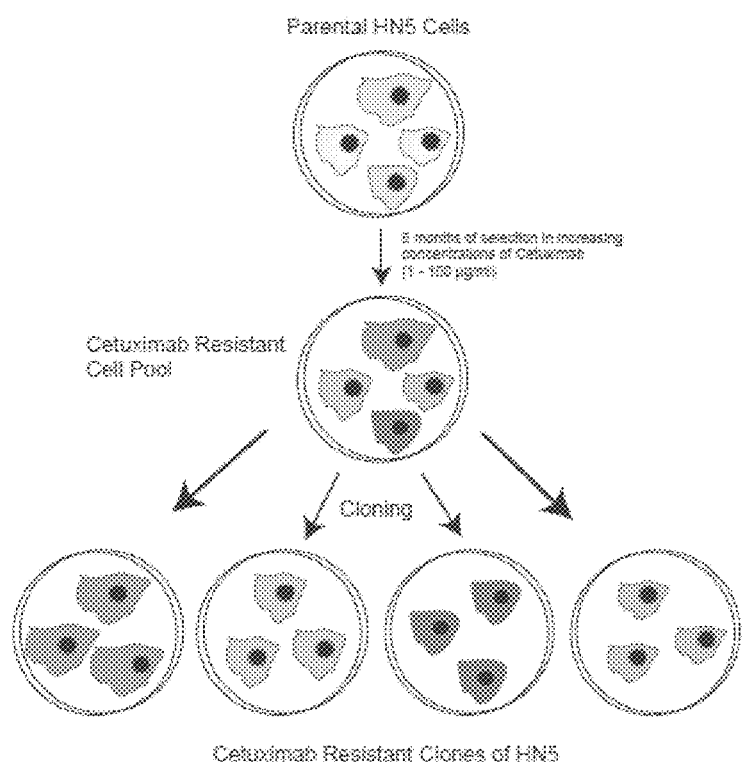
FIG. 36 is a schematic illustrating the development and cloning of acquired cetuximab resistant HN5 clones.

Example 11: Acquired Cetuximab Resistant HN5 Clones Show Decreased Total Levels of EGFR Together with High EGFR Activity Cetuximab resistant HN5 clones were established by exposing parental HN5 cells to increasing concentraions of cetuximab [1-100 μg/ml] during a period of six months. Cells were split twice a week in order to keep cells in expotential growth. The level of resistance to cetuximab was tested every month in a WST-1 viability assay as described in Example 2 until a pool of cetuximab resistant cells was established. Single cell clones were generated through limited dilution cloning of the acquired cetuximab resistant pool of HN5 cells. 0.5 cells/well were plated in 384 well plates. Growth and proliferation of single cell colonies was followed using Novartis Cellavista Imager. The most resistant individual clones, HN5 CR2, HN5 CR6, HN5 CR13, and HN5 CR14, were selected for further characterization (FIG. 35).

Figure 37:
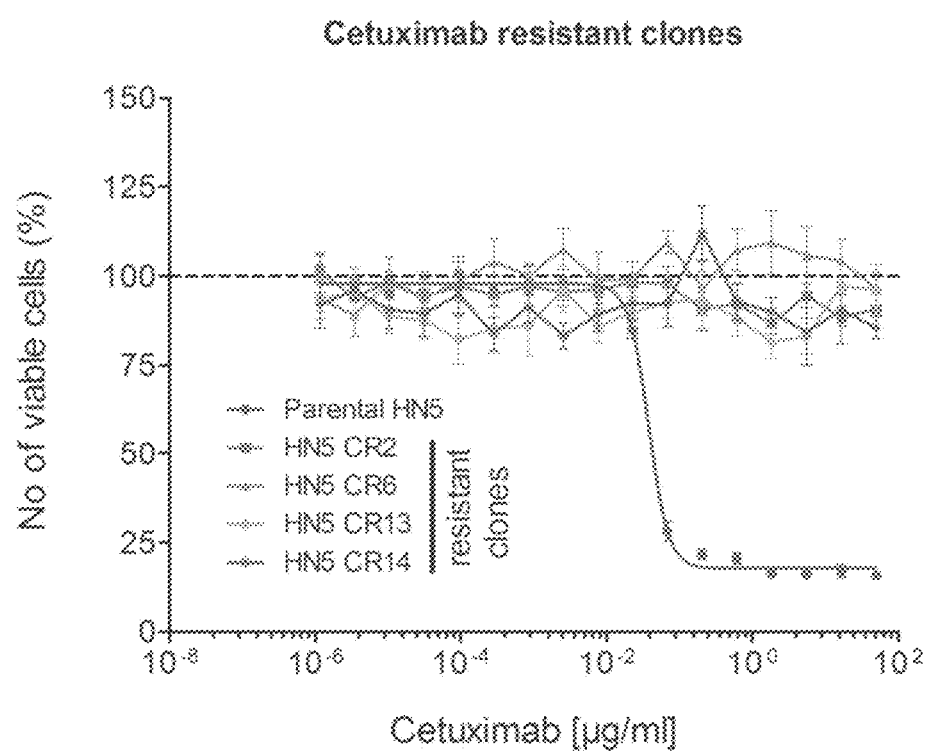
FIG. 37 is a graph showing the dose-response effects of cetuximab treatment on parental HN5 cells and cetuximab resistant clones HN5 CR2, HN5 CR6, HN5 CR13, and HN5 CR14.

Viabilty:

The level of cetuximab resistance of individual clones HN5 CR2, HN5 CR6, HN5 CR13, and HN5 CR14 was tested in a WST-1 viability assay as previously described in Example 1. Briefly, cells were treated with cetuximab at a range of concentrations and assayed 96 hours later. Unlike parental NH5 cells, resistant clones were viable with increasing concentrations of cetuximab treatment (FIG. 37).

Figure 38:
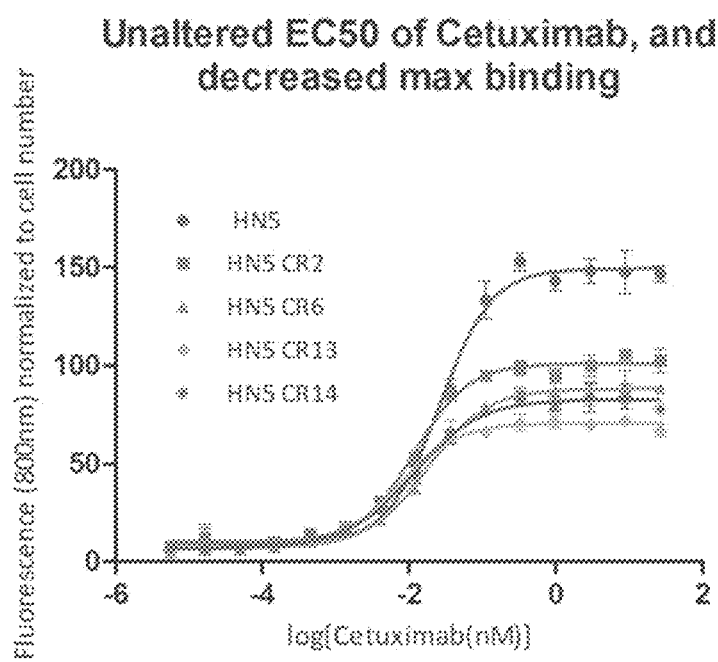
FIG. 38 is a graph showing the binding curve of cetuximab to fixed parental HN5 cells and cetuximab resistant clones HN5 CR2, HN5 CR6, HN5 CR13, and HN5 CR14.

Cetuximab Binding to Fixed Cells:

The binding strength of cetuximab to parental HN5 and resistant clones HN5 CR2, HN5 CR6, HN5 CR13, and HN5 CR14 was determined. Binding curves were generated by plotting fluorescence signals that were normalized to the number of cells (DRAQ-5 staining) and cetuximab concentrations. The results demonstrate that while half-maximal binding (i.e., EC50 value) of cetuximab was unaltered, maximal binding was decreased in the resistant clones compared to parental cells (FIG. 38).

Figure 39:
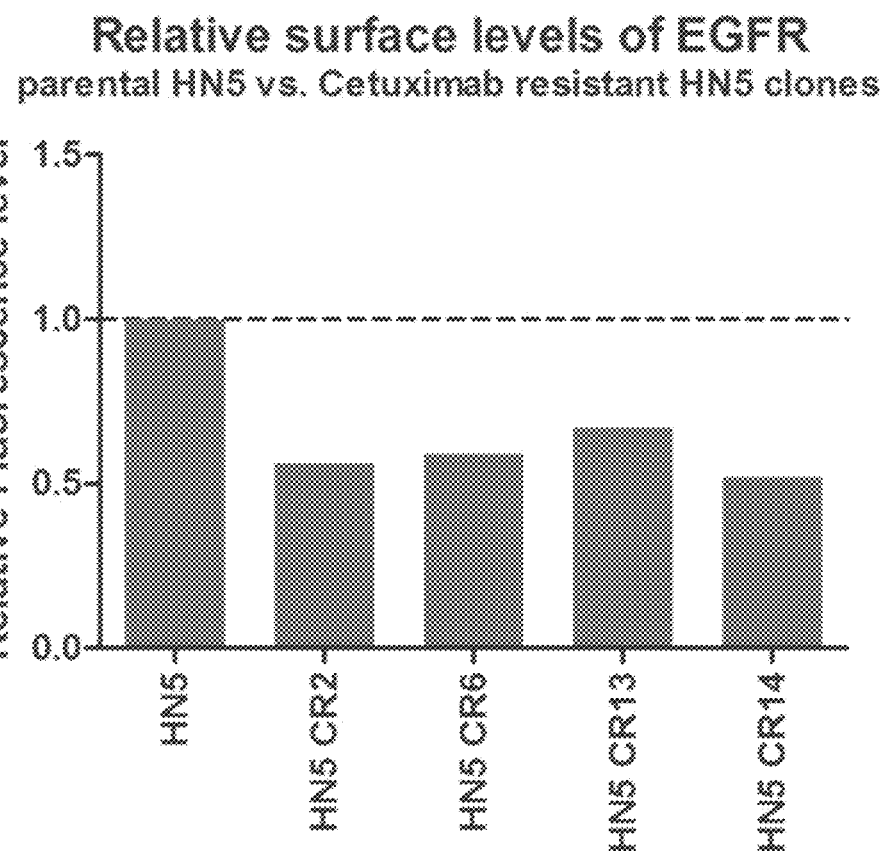
FIG. 39 is a graph showing the relative surface levels of EGFR found by fluorescence flow cytometry in parental HN5 cells and cetuximab resistant clones HN5 CR2, HN5 CR6, HN5 CR13, and HN5 CR14.

EGFR Expression and Signaling:

The relative surface levels of EGFR were determined in parental HN5 and resistant clones HN5 CR2, HN5 CR6, HN5 CR13, and HN5 CR14. Briefly, cells were stained with anti-EGFR-FITC (abcam, #11400) or an isotype control (abcam, #18446) and the relative fluorescence of live cells quantified by flow cytometry. The relative surface levels of EGFR were lower in cetuximab resistant HN5 clones compared to the parental cells (FIG. 39).

Figure 40:
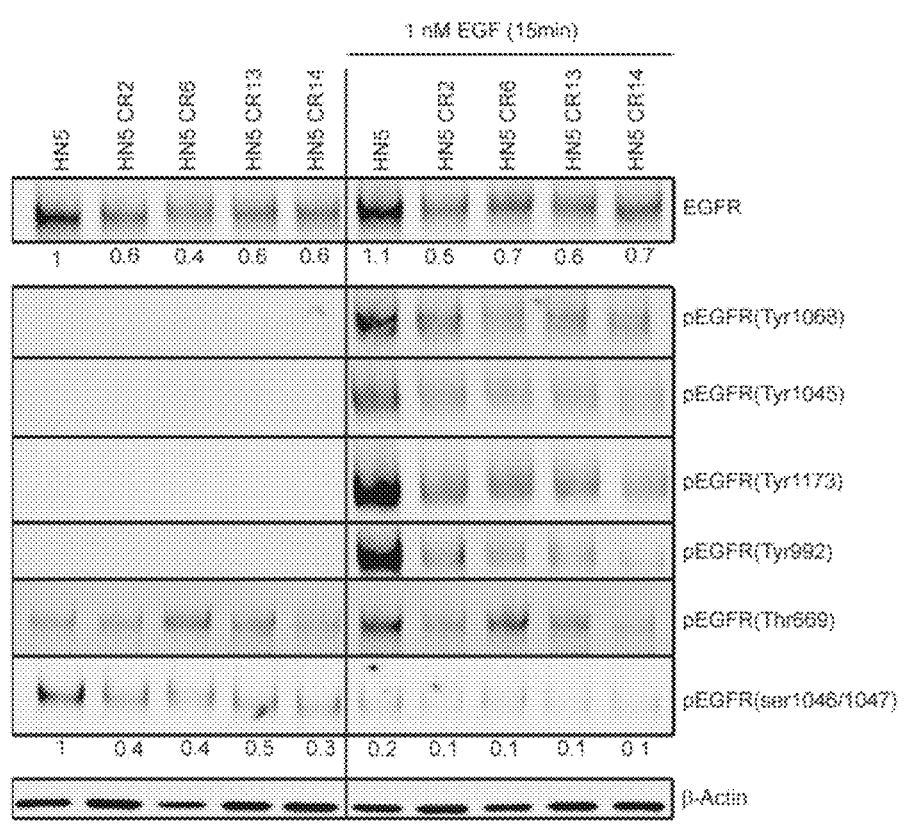
FIG. 40 is a series of Western blot images showing the total levels of EGFR, phosphorylated EGFR species, and a β-actin loading control in cell lysates from parental HN5 cells and cetuximab resistant clones HN5 CR2, HN5 CR6, HN5 CR13, and HN5 CR14 that were either untreated (left) or stimulated with EGF (right).
Figure 41:
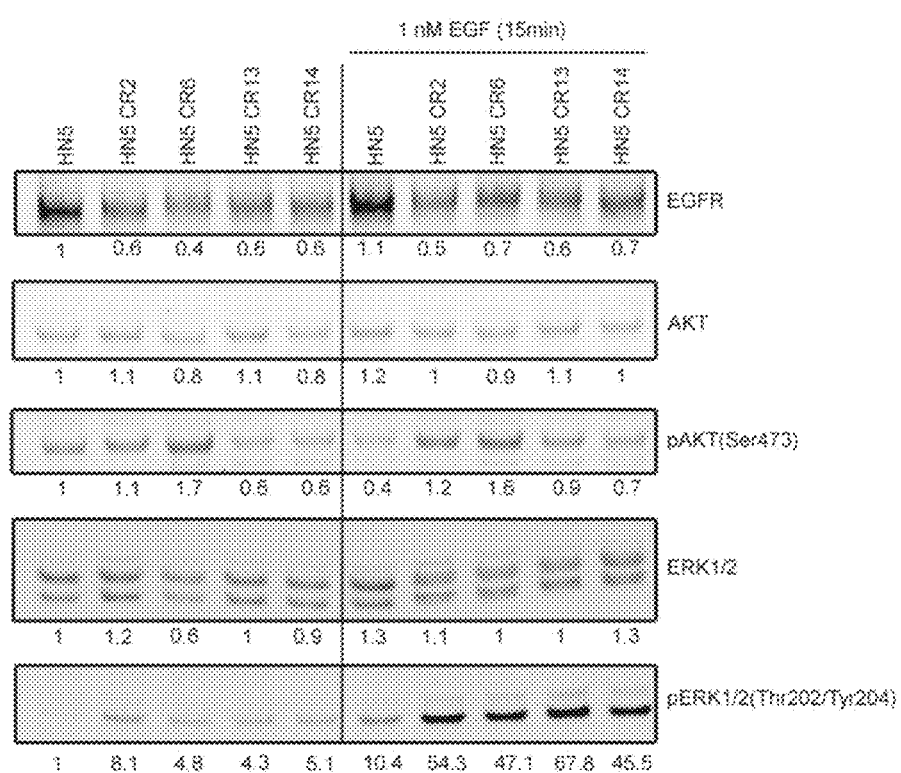
FIG. 41 is a series of Western blot images showing the total levels of EGFR, AKT, pAKT (Ser473), ERK1/2, pERK1/2(Thr202/Tyr204), and a β-actin loading control in cell lysates from parental HN5 cells and cetuximab resistant clones HN5 CR2, HN5 CR6, HN5 CR13, and HN5 CR14 that were either untreated (left) or stimulated with EGF (right).

The response of cetuximab resistant clones to EGF stimulation was tested. The total levels of EGFR, levels of phosphorylated EGFR and downstream signaling molecules were determined in parental HN5 and resistant clones HN5 CR2, HN5 CR6, HN5 CR13, and HN5 CR14. Parental HN5 cells and cetuximab resistant clones HN5 CR2, HN5 CR6, HN5 CR13, and HN5 CR14 were untreated or stimulated with 1 nM EGF for 15 min before harvesting. Lysates were fractionated on SDS-PAGE followed by Western Blotting for EGFR, the phosphorylated EGFR species pEGFR (Tyr1068), pEGFR(Tyr1045), pEGFR(Tyr1173), pEGFR (Tyr992), pEGFR(Thr669), and pEGFR(Ser1046/1047), and the signalling molecules AKT, pAKT (Ser473), ERK1/2, pERK1/2(Thr202/Tyr204) (FIGS. 40 and 41). β-Actin was used as a loading control. Results showed that the total levels of EGFR and phosphorylated EGFR were lower in cetuximab resistant HN5 clones compared to the parental cells (FIG. 40). The results also showed a decreased level of pEGFR(Ser1046/1047) in the cetuximab resistant clones, indicating that the feedback mechanism regulating EGFR is less active in the cetuximab resistant clones (FIG. 40). Stimulation with EGF induced a stronger activation of pAKT and pERK1/2 in the cetuximab resistant clones compared to parental HN5 cells (FIG. 41). Together, these results demonstrate that EGFR is still active in the cetuximab resistant clones, although EGFR expression is decreased compared to parental HN5 cells.

Figure 42:
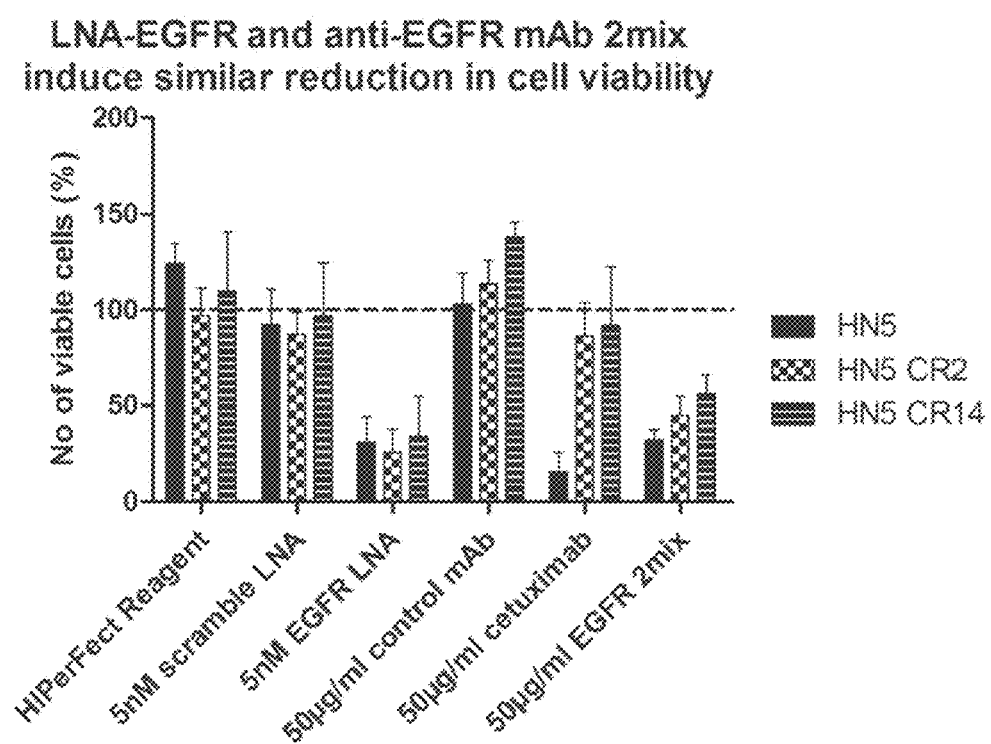
FIG. 42 is a graph showing the viability of parental HN5 cells and cetuximab resistant clones HN5 CR2 and HN5 CR14 treated with EGFR-LNA, cetuximab, EGFR-2mix (antibodies 1277 and 1565) or controls.

Example 12: Antibody Mixtures Targeting EGFR Overcome Cetuximab Resistance Through Efficient EGFR Internalization Followed by Degradation of the Receptor A mixture of antibodies targeting non-overlapping epitopes on EGFR was tested for its ability to partially overcome the cetuximab induced resistance in cetuximab resistant HN5 clones HN5 CR2 and HN5 CR14. Parental HN5, HN5 CR2, and HN5 CR14 cells were treated with EGFR-LNA™ (EGFR targeting Locked Nucleic Acid, Exiqon), Cetuximab or EGFR-2mix (antibodies 1277 and 1555) for 48 hours. Growth and proliferation was measured using a WST-1 assay as described in Example 2 and quantification of the effects were plotted with data points representing a mean+/−SEM (n=4) (FIG. 42). EGFR-LNA, and EGFR-2mix both induced a similar reduction in cell viability. These results demonstrated that a mixture of antibodies targeting non-overlapping epitopes on EGFR partially overcame the cetuximab induced resistance and that the cetuximab resistant clones remain dependent on EGFR for growth and proliferation (FIG. 42).

Figure 43:
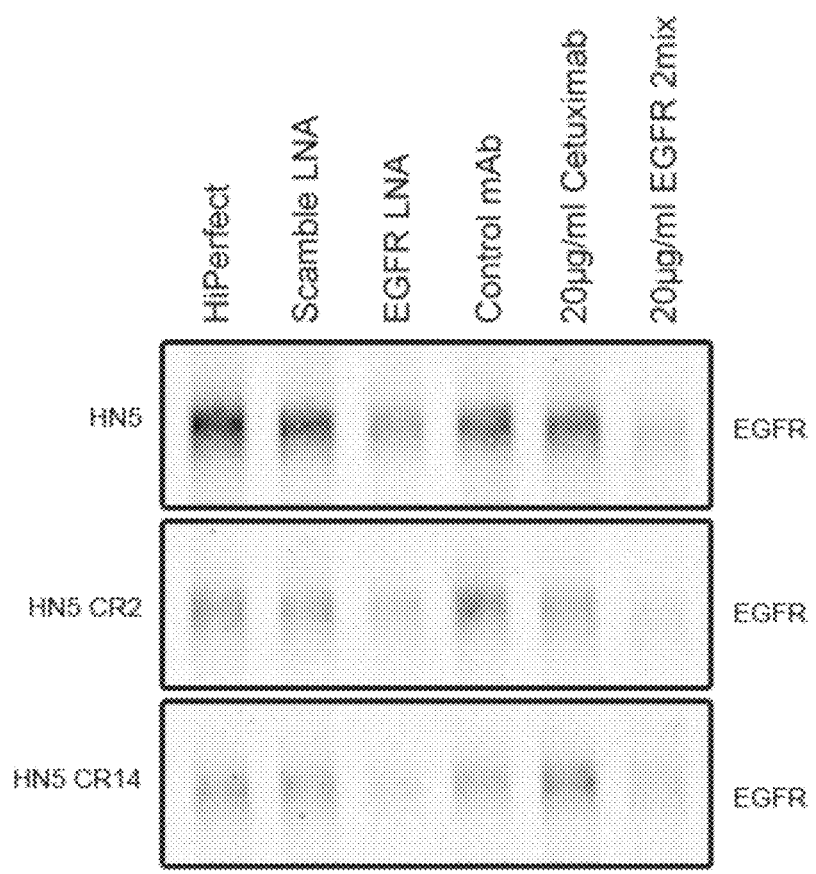
FIG. 43 is a series of Western blot images showing the total levels of EGFR in parental HN5 cells and cetuximab resistant clones HN5 CR2 and HN5 CR14 treated with EGFR-LNA, cetuximab, EGFR-2mix (antibodies 1277 and 1565) or controls.

The levels of EGFR in cells treated with EGFR-LNA, cetuximab or EGFR-2mix for 48 hour was determined by fractionating cellular lysates on a SDS-PAGE followed by Western Blotting for EGFR. The results showed that efficient EGFR internalization followed by lysosomal degradation of the receptor was induced in antibody treated resistant cells (FIG. 43), and thus providing a mechanism for the ability of the antibody mixture targeting EGFR overcome cetuximab resistance.

Figure 44:
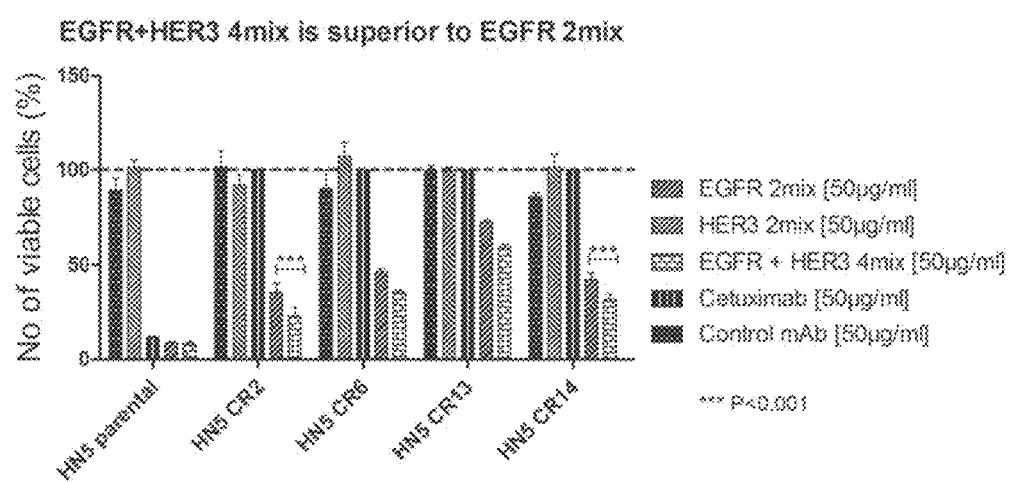
FIG. 44 is a graph showing the viability of parental HN5 cells and cetuximab resistant clones HN5 CR2, HN5 CR6, HN5 CR13, and HN5 CR14 treated with the indicated EGFR antibodies. "EGFR 2mix" refers to a mixture of antibodies 1277 and 1565. "Her3 2mix" refers to a mixture of antibodies 5038 and 5082.
Figure 45A:
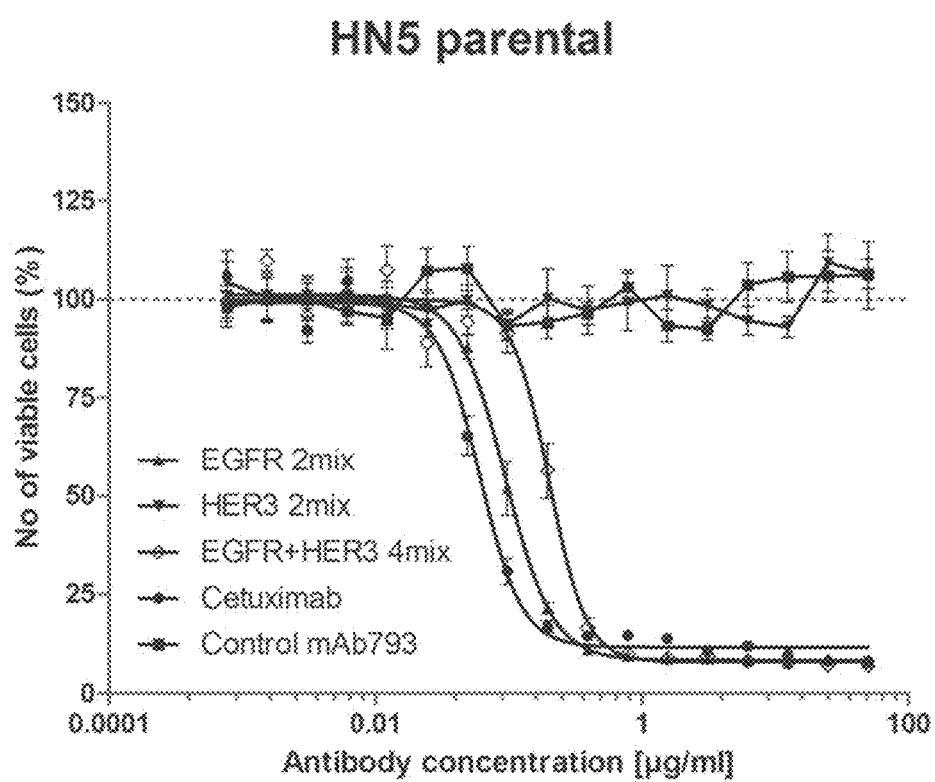
FIG. 45A shows the dose-response of parental HN5 cell viability to treatment with the indicated antibodies. "EGFR 2mix" refers to a mixture of antibodies 1277 and 1565. "Her3 2mix" refers to a mixture of antibodies 5038 and 5082. "EGFR+HER3 4mix" refers to a mixture of antibodies 1277, 1565, 5038 and 5082.
Figure 45B:
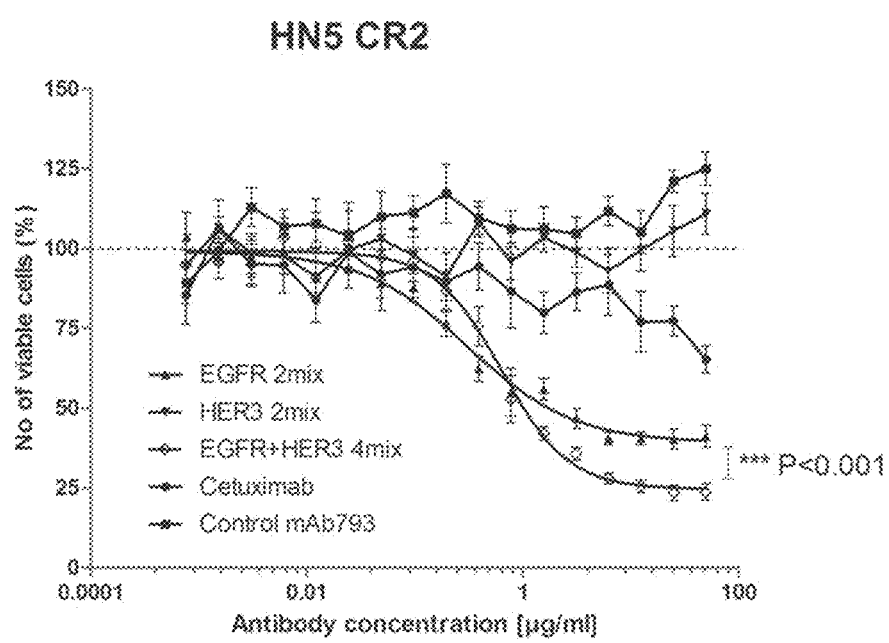
FIG. 45B shows the dose-response of cetuximab resistant clone HN5 CR2 viability to treatment with the indicated antibodies. "EGFR 2mix" refers to a mixture of antibodies 1277 and 1565. "Her3 2mix" refers to a mixture of antibodies 5038 and 5082. "EGFR+HER3 4mix" refers to a mixture of antibodies 1277, 1565, 5038 and 5082.

Example 13: Cetuximab Resistant HN5 Clones Escape Treatment Through HER3 and IGF1R The observed level of inhibition of the resistant clones by the anti-EGFR mixture did not, however, induce as efficient growth inhibition as in the parental cells, suggesting that alternative receptor tyrosine kinases (RTKs) may be involved in the mechanism of acquired cetuximab resistance. To test the role of HER3 activity in parental NH5 and resistant clones HN5 CR2, HN5 CR6, HN5 CR13, and HN5 CR14, cells were treated with a mixture of two EGFR antibodies (antibodies 1277 and 1565), a mixture of two HER3 antibodies (antibodies 5038 and 5082), a mixture of two EGFR and two HER3 antibodies (antibodies 1277, 1565, 5038 and 5082), or cetuximab for 48 hours. Growth and proliferation was measured using a WST-1 assay as described in Example 2 and quantification of the effects were plotted with data points representing as a mean+/−SEM (n=6). The results showed superior effects of the mixture containing antibodies targeting both HER3 and EGFR compared to effects induced by the EGFR antibody mixture alone. These results support the hypothesis of involvement of alternative RTKs in the acquired cetuximab resistance (FIG. 44). The dose response curves of parental HN5 and resistant HN5 CR2 cells to the antibody mixtures are shown in FIGS. 45A and B.

The involvement of HER3 in the acquired resistance to cetuximab shown here indicates the plasticity of the RTK family as a mechanism of acquired resistance to cetuximab in vitro.

TABLE 8

Sequences of selected chimeric antibodies

Antibody 1277: VH nucleotide sequence
cgcgccgaag tgcagctggt ggagtctggg ggaggcttag tgaagcctgg agagtccttg
aaactctcct gtgcagcctc tggattcgct ttcagttact ctgacatgtc ttgggttcgc
cagactccgg agaagaggct ggagtgggtc gcatacatga gtagtgctgg tgatgtcacc
ttctattcag acactgtgaa gggccgattc accatctcca gagacaatgc caagaacacc
ctgtatctgc aagtgagcag tctgaagtct gaggacacag ccatatatta ctgtgtaaga
caccgggacg tggctatgga ctactgggt caaggaacct cagtcaccgt ctcg (SEQ ID NO: 14)

Antibody 1277: VH amino acid sequence
Arg Ala Glu Val Gln Leu Val Glu Ser Gly Gly Gly Leu Val Lys Pro
Gly Glu Ser Leu Lys Leu Ser Cys Ala Ala Ser Gly Phe Ala Phe Ser
Tyr Ser Asp Met Ser Trp Val Arg Gln Thr Pro Glu Lys Arg Leu Glu
Trp Val Ala Tyr Met Ser Ser Ala Gly Asp Val Thr Phe Tyr Ser Asp
Thr Val Lys Gly Arg Phe Thr Ile Ser Arg Asp Asn Ala Lys Asn Thr
Leu Tyr Leu Gln Val Ser Ser Leu Lys Ser Glu Asp Thr Ala Ile Tyr
Tyr Cys Val Arg His Arg Asp Val Ala Met Asp Tyr Trp Gly Gln Gly
Thr Ser Val Thr Val Ser (SEQ ID NO: 15)

Antibody 1277: light chain nucleotide sequence
ctagccgatg ttgtgatgac ccagactcca ctctccctgc ctgtcagtct tggagatcaa
gcctccatct cttgcagatc tagtcagagc cttgtacaca gtaatggaaa caccctattta
cattggtacc tgcagaagcc aggccagtct ccaaagctcc tgatctacaa agtttccaac
cgattttctg gggtcccaga caggttcagt ggcagtggat cagggacaga tttcacactc
aagatcagca gagtggaggc tgaggatctg ggagtttatt tctgctctca aagtacacat
gttccgacgt tcggtggagg caccaagctg gaaatcaaac gaactgtggc tgcaccatct
gtcttcatct tcccgccatc tgatgagcag ttgaaatctg gaactgcctc tgttgtgtgc
ctgctgaata actctatcc cagagaggcc aaagtacagt ggaaggtgga taacgccctc
caatcgggta actcccagga gagtgtcaca gagcaggaca gcaaggacag cacctacagc
ctcagcagca ccctgacgct gagcaaagca gactacgaga aacacaaagt ctacgcctgc
gaagtcaccc atcagggcct gagctcgccc gtcacaaaga gcttcaacag gggagagtgt
(SEQ ID NO: 16)

Antibody 1277: light chain amino acid sequence
Leu Ala Asp Val Val Met Thr Gln Thr Pro Leu Ser Leu Pro Val Ser
Leu Gly Asp Gln Ala Ser Ile Ser Cys Arg Ser Ser Gln Ser Leu Val
His Ser Asn Gly Asn Thr Tyr Leu His Trp Tyr Leu Gln Lys Pro Gly
Gln Ser Pro Lys Leu Leu Ile Tyr Lys Val Ser Asn Arg Phe Ser Gly
Val Pro Asp Arg Phe Ser Gly Ser Gly Ser Gly Thr Asp Phe Thr Leu
Lys Ile Ser Arg Val Glu Ala Glu Asp Leu Gly Val Tyr Phe Cys Ser
Gln Ser Thr His Val Pro Thr Phe Gly Gly Gly Thr Lys Leu Glu Ile
Lys Arg Thr Val Ala Ala Pro Ser Val Phe Ile Phe Pro Pro Ser Asp
Glu Gln Leu Lys Ser Gly Thr Ala Ser Val Val Cys Leu Leu Asn Asn
Phe Tyr Pro Arg Glu Ala Lys Val Gln Trp Lys Val Asp Asn Ala Leu
Gln Ser Gly Asn Ser Gln Glu Ser Val Thr Glu Gln Asp Ser Lys Asp
Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser
Ser Pro Val Thr Lys Ser Phe Asn Arg Gly Glu Cys (SEQ ID NO: 17)

TABLE 8 -continued

Sequences of selected chimeric antibodies

Antibody 1565: VH nucleotide sequence
ggcgcgccga ggtccaactg caacagtctg ggactgaatt ggtgaagcct ggggcttcag
tgatactgtc ctgtaaggcc tctggctaca ccttcaccag ctactggatg cagtgggtga
agcagaggcc tggacaaggc cttgagtgga ttggaaatat taatcctagc aatggtggaa
ctagtttcaa tgaggagttc aagagtaggg ccacactgac tgtagacaaa tcctccagta
cagcctacat gcaactcagc agcctgacat ctgaggactc tgcggtctat tattgtgcaa
gagacggggg cctttacgac ggatactact ttgacttctg gggccaaggc accactctca
cagtctcgag (SEQ ID NO: 18)

Antibody 1565: VH amino acid sequence
Arg Ala Glu Val Gln Leu Gln Gln Ser Gly Thr Glu Leu Val Lys Pro
Gly Ala Ser Val Ile Leu Ser Cys Lys Ala Ser Gly Tyr Thr Phe Thr
Ser Tyr Trp Met Gln Trp Val Lys Gln Arg Pro Gly Gln Gly Leu Glu
Trp Ile Gly Asn Ile Asn Pro Ser Asn Gly Gly Thr Ser Phe Asn Glu
Glu Phe Lys Ser Arg Ala Thr Leu Thr Val Asp Lys Ser Ser Ser Thr
Ala Tyr Met Gln Leu Ser Ser Leu Thr Ser Glu Asp Ser Ala Val Tyr
Tyr Cys Ala Arg Asp Gly Gly Leu Tyr Asp Gly Tyr Tyr Phe Asp Phe
Trp Gly Gln Gly Thr Thr Leu Thr Val Ser (SEQ ID NO: 19)

Antibody 1565: light chain nucleotide sequence
gctagccaac attgtgatga cacagtctca caaattcatg tccacattaa taggagccag
ggtctccatc acctgcaagg ccagtcagga tgtggatacg gclgtagcct ggtatcaaca
gaaaccaggt caatccctaa aattattaat ttattgggca tccacccggc acactggagt
ccctgatcgc ttcacaggca gtggatctgg gacagatttc tctctcaccg ttagcaatgt
gcaatctaag gacttaacag attatttctg tcagcaatat agcagctatc ctctcacgtt
cggtgctggg accaagctgg agctgaaacg aactgtggct gcaccatctg tcttcatctt
cccgccatct gatgagcagt tgaaatctgg aactgcctct gttgtgtgcc tgctgaataa
cttctatccc aqagaggcca agtacagtg gaaggtgata aacgccctcc aatcgggtaa
ctcccagqag agtgtcacaq agcaggacag caaggacagc acctacagcc tcagcagcac
cctgacgctg agcaaagcag actacgaqaa cacaaaqtc tacgcctgcg aagtcaccca
tcagggcctg agctcgcccg tcacaaagag cttcaacagg gagaqtgtt aataaqcggc
cgc (SEQ ID NO: 20)

Antibody 1565: light chain amino acid sequence
Leu Ala Asn Ile Val Met Thr Gln Ser His Lys Phe Met Ser Thr Leu
Ile Gly Ala Arg Val Ser Ile Thr Cys Lys Ala Ser Gln Asp Val Asp
Thr Ala Val Ala Trp Tyr Gln Gln Lys Pro Gly Gln Ser Pro Lys Leu
Leu Ile Tyr Trp Ala Ser Thr Arg His Thr Gly Val Pro Asp Arg Phe
Thr Gly Ser Gly Ser Gly Thr Asp Phe Ser Leu Thr Val Ser Asn Val
Gln Ser Glu Asp Lau Thr Asp Tyr Phe Cys Gln Gln Tyr Ser Ser Tyr
Pro Leu Thr Phe Gly Ala Gly Thr Lys Leu Glu Leu Lys Arg Thr Val
Ala Ala Pro Ser Val Phe Ile Phe Pro Pro Ser Asp Glu Gln Leu Lys
Ser Gly Thr Ala Ser Val Val Cys Leu Leu Asn Asn Phe Tyr Pro Arg
Glu Ala Lys Val Gln Trp Lys Val Asp Asn Ala Leu Gln Ser Gly Asn
Ser Gln Glu Ser Val Thr Glu Gln Asp Ser Lys Asp Ser Thr Tyr Ser
Leu Ser Ser Thr Leu Thr Leu Ser Lys Ala Asp Tyr Glu Lys His Lys
Val Tyr Ala Cys Glu Val Thr His Gln Gly Leu Ser Ser Pro Val Thr
Lys Ser Phe Asn Arg Gly Glu Cys (SEQ ID NO: 21)

Antibody 4384: VH nucleotide sequence
caggtgcagc tgcagcagcc tggcacagag ctggtgaaac ctggcgcctc cgtgaagctg
tcctgcaagg cctccggcta caccttcacc tcccactgga tgcactgggt gaaacagcgg
cctgacaggg gcctggaatg gatcggcaac atcaaccctt ccaacggcgg caccaactac
aacgagaagt tcaagtcccg ggccaccctg accgtggaca aggcctcctc caccgcctac
atgcagctgt cctccctgac ctccgaggac tccgccgtgt actactgcgc cagagcctac
tacgacttca gttggttcgt gtactggggc cagggcaccc tggtgacagt ctcg (SEQ ID NO: 22)

Antibody 4384: VH amino acid sequence
Gln Val Gln Leu Gln Gln Pro Gly Thr Glu Leu Val Lys Pro Gly Ala
Ser Val Lys Leu Ser Cys Lys Ala Ser Gly Tyr Thr Phe Thr Ser His
Trp Met His Trp Val Lys Gln Arg Pro Gly Gln Gly Leu Glu Trp Ile
Gly Asn Ile Asn Pro Ser Asn Gly Gly Thr Asn Tyr Asn Glu Lys Phe
Lys Ser Arg Ala Thr Leu Thr Val Asp Lys Ala Ser Ser Thr Ala Tyr
Met Gln Leu Ser Ser Leu Thr Ser Glu Asp Ser Ala Val Tyr Tyr Cys
Ala Arg Ala Tyr Tyr Asp Phe Ser Trp Phe Val Tyr Trp Gly Gln Gly
Thr Leu Val Thr Val Ser (SEQ ID NO: 23)

Antibody 4384: light chain nucleotide sequence
gatatccaga tgacccagac ctcctccagc ctgtccgcct ccctgggcga cagagtgacc
atctcctgcc ggtcctccca ggacatctcc aactacctga actggtatca gcagaaaccc
gacqgcaccg tgaagctgct gatgtacatc tccggctgc actccggcgt gccctccaga
ttctccgact ctgactccag caccgagtac tccctgacca tcagcaacct ggaacaggaa
gatatcgcta cctacttctg tcagcagggc aacaccctgc cctgaccttc ggcgctggc
accaagctgg aactgaagcg gacgtggcc gctccctccg tgttcatctt cccacccctcc
gacgagcagc tgaagtccgg caccgcctcc gtggtgtgcc tgctgaacaa cttctacccc TABLE 8 -continued Sequences of selected chimeric antibodies

```
cgcgaggcca aggtgcagtg gaaggtggac aacgccctgc agtccggcaa ctcccaggaa
tccgtgaccg agcaggactc caaggacagc acctactccc tgtcctccac cctgaccctg
tccaaggccg actacgagaa gcacaaggtg tacgcctgcg aagtgaccca ccagggcctg
tccagcccg tgaccaagtc cttcaaccgg ggcgagtgc (SEQ ID NO: 24)
```

Antibody 4384: light chain amino acid sequence
Asp Ile Gln Met Thr Gln Thr Ser Ser Ser Leu Ser Ala Ser Leu Gly
Asp Arg Val Thr Ile Ser Cys Arg Ser Ser Gln Asp Ile Ser Asn Tyr
Leu Asn Trp Tyr Gln Gln Lys Pro Asp Gly Thr Val Lys Leu Leu Met
Tyr Ile Ser Arg Leu His Ser Gly Val Pro Ser Arg Phe Ser Gly Ser
Gly Ser Gly Thr Glu Tyr Ser Leu Thr Ile Ser Asn Leu Glu Gln Glu
Asp Ile Ala Thr Tyr Phe Cys Gln Gln Gly Asn Thr Leu Pro Leu Thr
Phe Gly Ala Gly Thr Lys Leu Glu Leu Lys Arg Thr Val Ala Ala Pro
Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys
Val Gln Trp Lys Val Asp Asn Ala Leu Gln Ser Gly Asn Ser Gln Glu
Ser Val Thr Glu Gln Asp Ser Lys Asp Ser Thr Tyr Ser Leu Ser Ser
Thr Leu Thr Leu Ser Lys Ala Asp Tyr Glu Lys His Lys Val Tyr Ala
Cys Glu Val Thr His Gln Gly Leu Ser Ser Pro Val Thr Lys Ser Phe
Asn Arg Gly Glu Cys (SEQ ID NO: 25)

Antibody 4517: VH nucleotide sequence
```
gaagtgcagc tggtggaatc tggcggcgac ctggtgaaac ctggcggctc cctgaagctg
tcctgcgccg cctccggctt caccttctcc agctacggca tgtcctgggt gcgactgacc
cccgacaagc ggctggaatg ggtggcaacc atctccggcg gaggctccta cacctactac
cccgactccg tgaagggccg gttcaccatc tcccgggata tcgccaagtc caccctgtac
ctgcagatgt cctccctgaa gtccgaggac accgccgtgt actactgcgc ccggaagggc
aactacggca attacggcaa gctggcctac tggggccagg gcacctccgt gacagtctcg
(SEQ ID NO: 26)
```

Antibody 4517: VH amino acid sequence
Glu Val Gln Leu Val Glu Ser Gly Gly Asp Leu Val Lys Pro Gly Gly
Ser Leu Lys Leu Ser Cys Ala Ala Ser Gly Phe Thr Phe Ser Ser Tyr
Gly Met Ser Trp Val Arg Leu Thr Pro Asp Lys Arg Leu Glu Trp Val
Ala Thr Ile Ser Gly Gly Gly Ser Tyr Thr Tyr Tyr Pro Asp Ser Val
Lys Gly Arg Phe Thr Ile Ser Arg Asp Ile Ala Lys Ser Thr Leu Tyr
Leu Gln Met Ser Ser Leu Lys Ser Glu Asp Thr Ala Val Tyr Tyr Cys
Ala Arg Lys Gly Asn Tyr Gly Asn Tyr Gly Lys Leu Ala Tyr Trp Gly
Gln Gly Thr Ser Val Thr Val Ser (SEQ ID NO: 27)

Antibody 4517: light chain nucleotide sequence
```
gatatccaga tgacccagtc ccccgcctcc ctgtccgtgt ctgtgggcga cacagtgacc
atcacctgtc gggcctccga aacatctac tccaacctgg cctggtatca gcaggaacag
ggcaagtccc cccagctgct ggtgtacgcc gccaccaatc tggccgacgg cgtgccctcc
agattctccg gctctggctc cggcacccag tactccctga agatcaactc cctgcagtcc
gaggacttcg gctcctacta ctgccagcac ttctggggca ccccctggac cttcggcgga
ggcaccaagc tggaaatcaa gcggaccgtg gccgctccct ccgtgttcat cttcccaccc
tccgacgagc agctgaagtc cggcaccgcc tccgtggtgt gcctgctgaa caacttctac
ccccgcgagg ccaaggtgca gtggaaggtg gacaacgccc tgcagagcgg caactcccag
gaatccgtga ccgagcagga ctccaaggac agcaccact ccctgtcctc caccctgacc
ctgtccaagg ccgactacga gaagcacaag gtgtacgcct gcgaagtgac ccaccagggc
ctgtccagcc ccgtgaccaa gtccttcaac cggggcgagt gc (SEQ ID NO: 28)
```

Antibody 4517: light chain amino acid sequence
Asp Ile Gln Met Thr Gln Ser Pro Ala Ser Leu Ser Val Ser Val Gly
Glu Thr Val Thr Ile Thr Cys Arg Ala Ser Glu Asn Ile Tyr Ser Asn
Leu Ala Trp Tyr Gln Gln Glu Gln Gly Lys Ser Pro Gln Leu Leu Val
Tyr Ala Ala Thr Asn Leu Ala Asp Gly Val Pro Ser Arg Phe Ser Gly
Ser Gly Ser Gly Thr Gln Tyr Ser Leu Lys Ile Asn Ser Leu Gln Ser
Glu Asp Phe Gly Ser Tyr Tyr Cys Gln His Phe Trp Gly Thr Pro Trp
Thr Phe Gly Gly Gly Thr Lys Leu Glu Ile Lys Arg Thr Val Ala Ala
Pro Ser Val Phe Ile Phe Pro Pro Ser Asp Glu Gln Leu Lys Ser Gly
Thr Ala Ser Val Val Cys Leu Leu Asn Asn Phe Tyr Pro Arg Glu Ala
Lys Val Gln Trp Lys Val Asp Asn Ala Leu Gln Ser Gly Asn Ser Gln
Glu Ser Val Thr Glu Gln Asp Ser Lys Asp Ser Thr Tyr Ser Leu Ser
Ser Thr Leu Thr Leu Ser Lys Ala Asp Tyr Glu Lys His Lys Val Tyr
Ala Cys Glu Val Thr His Gln Gly Leu Ser Ser Pro Val Thr Lys Ser
Phe Asn Arg Gly Glu Cys (SEQ ID NO: 29)

Antibody 5038: VH nucleotide sequence
```
cgcgccgaga tgaagctagt tgagtcagga cctggcctcg tgaaaccttc tcagtctctg
tctctcacct gctctgtcac tggctactcc atcaccagtg gttttacta gacctggatc
cggcagtttc caggcaacaa attggaataa atgagcttca taagctacga tggtagcaat
aactacaacc catctctcaa aaatcgaatc tccatcactc gtgacacatc taagaaccaa
ttttttcctga agttgaattc tgtgactact gaggacacag ccacatatta ctgtgcaaga
ggcggagact atatggtaa cctctttgac tactggggcc aaggcaccac tctcacagtc
tcga (SEQ ID NO: 30)
```

TABLE 8 -continued

Sequences of selected chimeric antibodies

Antibody 5038: VH amino acid sequence
Arg Ala Glu Val Lys Leu Val Glu Ser Gly Pro Gly Leu Val Lys Pro
Ser Gln Ser Leu Ser Leu Thr Cys Ser Val Thr Gly Tyr Ser Ile Thr
Ser Gly Phe Tyr Trp Thr Trp Ile Arg Gln Phe Pro Gly Asn Lys Leu
Glu Trp Met Gly Phe Ile Ser Tyr Asp Gly Ser Asn Asn Tyr Asn Pro
Ser Leu Lys Asn Arg Ile Ser Ile Thr Arg Asp Thr Ser Lys Asn Gln
Phe Phe Leu Lys Leu Asn Ser Val Thr Thr Glu Asp Thr Ala Thr Tyr
Tyr Cys Ala Arg Gly Gly Tyr Tyr Gly Asn Leu Phe Asp Tyr Trp
Gly Gln Gly Thr Thr Leu Thr Val Ser (SEQ ID NO: 31)

Antibody 5038: light chain nucleotide sequence
ctagccgata ttgtgatgac tcaaactaca tcctccctgt ccgcctctct gggagacaga
gtcaccatca gttgcaggcc aagtcaggac attagcaatt atgtaaactg gtttcagcag
aaaccaggtg aactgttaa gctcctgatc ttccacacat caagattaca ctcaggagtc
ccatcaaggt tcagtggcag tgggtctgga acagattatt ctctcaccat tagcaccctg
gaacaggaag atattgccat ttactttgc aacagggta ttacgcttcc gtggacgttc
ggtggcggca ccaagctgga aataaaacga actgtggctg caccatctgt cttcatcttc
ccgccatctg atgagcagtt gaaatctgga actgcctctg ttgtgtgcct gctgaataac
ttctatccca gagaggccaa agtacagtgg aaggtgtta acgccctcca atcgggtaac
tcccaggaga gtgtcacaga gcaggacagc aaggacagca cctacagcct cagcagcacc
ctgacgctga gcaaagcaga ctacgagaaa cacaaagtct acgcctgcga agtcacccat
cagggcctga gctcgcccgt cacaaagagc ttcaacaggg gagagtgtta ataagcggcc
(SEQ ID NO: 32)

Antibody 5038: light chain amino acid sequence
Leu Ala Asp Ile Val Met Thr Gln Thr Thr Ser Ser Leu Ser Ala Ser
Leu Gly Asp Arg Val Thr Ile Ser Cys Arg Pro Ser Gln Asp Ile Ser
Asn Tyr Val Asn Trp Phe Gln Gln Lys Pro Gly Gly Thr Val Lys Leu
Leu Ile Phe His Thr Ser Arg Leu His Ser Gly Val Pro Ser Arg Phe
Ser Gly Ser Gly Ser Gly Thr Asp Tyr Ser Leu Thr Ile Ser Thr Leu
Glu Gln Glu Asp Ile Ala Ile Tyr Phe Cys Gln Gln Gly Ile Thr Leu
Pro Trp Thr Phe Gly Gly Gly Thr Lys Leu Glu Ile Lys Arg Thr Val
Ala Ala Pro Ser Val Phe Ile Phe Pro Pro Ser Asp Glu Gln Leu Lys
Ser Gly Thr Ala Ser Val Val Cys Leu Leu Asn Asn Phe Tyr Pro Arg
Glu Ala Lys Val Gln Trp Lys Val Asp Asn Ala Leu Gln Ser Gly Asn
Ser Gln Glu Ser Val Thr Glu Gln Asp Ser Lys Asp Ser Thr Tyr Ser
Leu Ser Ser Thr Leu Thr Leu Ser Lys Ala Asp Tyr Glu Lys His Lys
Val Tyr Ala Cys Glu Val Thr His Gln Gly Leu Ser Ser Pro Val Thr
Lys Ser Phe Asn Arg Gly Glu Cys (SEQ ID NO: 33)

Antibody 5082: VH nucleotide sequence
cgcgccgagg tgcagctgaa ggagtcagga cctggcctcg tgaaaccttc tcagtctctg
tctctcacct gctctgtcac cggctactcc atcaccagtg cttattactg gaactggatc
cggcagtttc caggaaacaa agtggaatgg atgggctaca taggctacga tggtcgtaat
acctacaacc catctctcaa aaatcgaatc tccatcactc gtgacacatc taagaaccag
tttttcctga aattgaattc tctgactact gaggacacag ccacatatta ttgttcaaga
gaggggggact acggttactc tgactactgg ggccaaggca ccactctcac agtctcga (SEQ ID NO: 34)

Antibody 5082: VH amino acid sequence
Arg Ala Glu Val Gln Leu Lys Glu Ser Gly Pro Gly Leu Val Lys Pro
Ser Gln Ser Leu Ser Leu Thr Cys Ser Val Thr Gly Tyr Ser Ile Thr
Ser Ala Tyr Tyr Trp Asn Trp Ile Arg Gln Phe Pro Gly Asn Lys Val
Glu Trp Met Gly Tyr Ile Gly Tyr Asp Gly Arg Asn Thr Tyr Asn Pro
Ser Leu Lys Asn Arg Ile Ser Ile Thr Arg Asp Thr Ser Lys Asn Gln
Phe Phe Leu Lys Leu Asn Ser Leu Thr Thr Glu Asp Thr Ala Thr Tyr
Tyr Cys Ser Arg Glu Gly Asp Tyr Gly Tyr Ser Asp Tyr Trp Gly Gln
Gly Thr Thr Leu Thr Val Ser (SEQ ID NO: 35)

Antibody 5082: light chain nucleotide sequence
ctagccgata ttgtgatgac gcaagctaca tcctccctgt ctgcctctct gggagacaga
gtcaccgtca gttgcagggc aagtcaggac attaacaatt atttaaattg gtatcagcag
aagccagatg aactgttaa actcctgatc tactacacat caagattaca gtcaggagtc
ccatcaaggt tcagtggcag tgggtctgga atagattatt ctctcaccat tagcaacctg
gagcaggaag attttgtcac ttactttgc aacagagtg aaacgcttcc gtggacgttc
ggtggaggca ccaagctgga gatgaaacga actgtggctg caccatctgt cttcatcttc
ccgccatctg atgagcagtt gaaatctgga actgcctctg ttgtgtgcct gctgaataac
ttctatccca gagaggccaa agtacagtgg aaggtggata acgccctcca atcgggtaac
tcccaggaga gtgtcacaga gcaggacagc aaggacagca cctacagcct cagcagcacc
ctgacgctga gcaaagcaga ctacgagaaa cacaaagtct acgcctgcga agtcacccat
cagggcctga gctcgcccgt cacaaagagc ttcaacaggg gagagtgtta ataagcggcc
(SEQ ID NO: 36)

Antibody 5082: light chain amino acid sequence
Leu Ala Asp Ile Val Met Thr Gln Ala Thr Ser Ser Leu Ser Ala Ser
Leu Gly Asp Arg Val Thr Val Ser Cys Ara Ala Ser Gln Asp Ile Asn
Asn Tyr Leu Asn Trp Tyr Gln Gln Lys Pro Asp Gly Thr Val Lys Leu
Leu Ile Tyr Tyr Thr Ser Arg Leu Gln Ser Gly Val Pro Ser Arg Phe
Ser Gly Ser Gly Ser Gly Ile Asp Tyr Ser Leu Thr Ile Ser Asn Leu TABLE 8 -continued Sequences of selected chimeric antibodies Glu Gln Glu Asp Phe Val Thr Tyr Phe Cys Gln Gln Ser Glu Thr Leu
Pro Trp Thr Phe Gly Gly Gly Thr Lys Leu Glu Leu Lys Arg Thr Val
Ala Ala Pro Ser Val Phe Ile Phe Pro Pro Ser Asp Gln Gln Leu Lys
Ser Gly Thr Ala Ser Val Val Cys Leu Leu Asn Asn Phe Tyr Pro Arg
Glu Ala Lys Val Gln Trp Lys Val Asp Asn Ala Leu Gln Ser Gly Asn
Ser Gln Glu Ser Val Thr Glu Gln Asp Ser Lys Asp Ser Thr Tyr Ser
Leu Ser Ser Thr Leu Thr Leu Ser Lys Ala Asp Tyr Glu Lys His Lys
Val Tyr Ala Cys Glu Val Thr His Gln Gly Leu Ser Ser Pro Val Thr
Lys Ser Phe Asn Arg Gly Glu Cys (SEQ ID NO: 37)

SEQUENCE LISTING

<160> NUMBER OF SEQ ID NOS: 74

<210> SEQ ID NO 1
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 1277 VH polypeptide"
<220> FEATURE:
<221> NAME/KEY: VARIANT
<222> LOCATION: (44)..(44)
<223> OTHER INFORMATION: /replace="Arg"
<220> FEATURE:
<221> NAME/KEY: VARIANT
<222> LOCATION: (49)..(49)
<223> OTHER INFORMATION: /replace="Ala"
<220> FEATURE:
<221> NAME/KEY: VARIANT
<222> LOCATION: (83)..(83)
<223> OTHER INFORMATION: /replace="Val"
<220> FEATURE:
<221> NAME/KEY: VARIANT
<222> LOCATION: (104)..(104)
<223> OTHER INFORMATION: /replace="Ile"
<220> FEATURE:
<221> NAME/KEY: misc_feature
<222> LOCATION: (1)..(117)
<223> OTHER INFORMATION: /note="Variant residues given in the sequence
      have no preference with respect to those in the annotations for
      variant positions"

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Tyr Ser
            20                  25                  30

Asp Met Ser Trp Val Arg Gln Ala Pro Gly Lys Gly Leu Glu Trp Val
        35                  40                  45

Ser Tyr Met Ser Ser Ala Gly Asp Val Thr Phe Tyr Ser Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg His Arg Asp Val Ala Met Asp Tyr Trp Gly Gln Gly Thr Thr
        100                 105                 110

Val Thr Val Ser Ser
        115

<210> SEQ ID NO 2

```
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 1277 VL polypeptide"
<220> FEATURE:
<221> NAME/KEY: VARIANT
<222> LOCATION: (13)..(13)
<223> OTHER INFORMATION: /replace="Val"
<220> FEATURE:
<221> NAME/KEY: VARIANT
<222> LOCATION: (19)..(19)
<223> OTHER INFORMATION: /replace="Ala"
<220> FEATURE:
<221> NAME/KEY: MOD_RES
<222> LOCATION: (33)..(34)
<223> OTHER INFORMATION: Any naturally occurring amino acid
<220> FEATURE:
<221> NAME/KEY: VARIANT
<222> LOCATION: (42)..(42)
<223> OTHER INFORMATION: /replace="Leu"
<220> FEATURE:
<221> NAME/KEY: VARIANT
<222> LOCATION: (48)..(48)
<223> OTHER INFORMATION: /replace="Ser"
<220> FEATURE:
<221> NAME/KEY: VARIANT
<222> LOCATION: (83)..(83)
<223> OTHER INFORMATION: /replace="Val"
<220> FEATURE:
<221> NAME/KEY: VARIANT
<222> LOCATION: (89)..(89)
<223> OTHER INFORMATION: /replace="Gly"
<220> FEATURE:
<221> NAME/KEY: VARIANT
<222> LOCATION: (92)..(92)
<223> OTHER INFORMATION: /replace="Phe"
<220> FEATURE:
<221> NAME/KEY: VARIANT
<222> LOCATION: (108)..(108)
<223> OTHER INFORMATION: /replace="Leu"
<220> FEATURE:
<221> NAME/KEY: misc_feature
<222> LOCATION: (1)..(111)
<223> OTHER INFORMATION: /note="Variant residues given in the sequence
      have no preference with respect to those in the annotations for
      variant positions"

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Xaa Xaa Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Thr Phe Gly Gly Gly Thr Lys Val Glu Ile Lys
            100                 105                 110

<210> SEQ ID NO 3
<211> LENGTH: 111
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic Humanized 1277A VL polypeptide"
<220> FEATURE:
<221> NAME/KEY: VARIANT
<222> LOCATION: (33)..(33)
<223> OTHER INFORMATION: /replace="Ser"
<220> FEATURE:
<221> NAME/KEY: VARIANT
<222> LOCATION: (34)..(34)
<223> OTHER INFORMATION: /replace="Leu"
<220> FEATURE:
<221> NAME/KEY: VARIANT
<222> LOCATION: (41)..(41)
<223> OTHER INFORMATION: /replace="Tyr"
<220> FEATURE:
<221> NAME/KEY: VARIANT
<222> LOCATION: (42)..(42)
<223> OTHER INFORMATION: /replace="Leu"
<220> FEATURE:
<221> NAME/KEY: VARIANT
<222> LOCATION: (51)..(51)
<223> OTHER INFORMATION: /replace="Leu"
<220> FEATURE:
<221> NAME/KEY: VARIANT
<222> LOCATION: (92)..(92)
<223> OTHER INFORMATION: /replace="Phe"
<220> FEATURE:
<221> NAME/KEY: VARIANT
<222> LOCATION: (108)..(108)
<223> OTHER INFORMATION: /replace="Leu"
<220> FEATURE:
<221> NAME/KEY: misc_feature
<222> LOCATION: (1)..(111)
<223> OTHER INFORMATION: /note="Variant residues given in the sequence
      have no preference with respect to those in the annotations for
      variant positions"

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys
            100                 105                 110

<210> SEQ ID NO 4
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 1565 VH polypeptide"
<220> FEATURE:
<221> NAME/KEY: VARIANT
<222> LOCATION: (20)..(20)
<223> OTHER INFORMATION: /replace="Leu"
<220> FEATURE:
<221> NAME/KEY: VARIANT
<222> LOCATION: (38)..(38)
<223> OTHER INFORMATION: /replace="Lys"
<220> FEATURE:
```

```
<221> NAME/KEY: VARIANT
<222> LOCATION: (40)..(40)
<223> OTHER INFORMATION: /replace="Arg"
<220> FEATURE:
<221> NAME/KEY: VARIANT
<222> LOCATION: (48)..(48)
<223> OTHER INFORMATION: /replace="Ile"
<220> FEATURE:
<221> NAME/KEY: MOD_RES
<222> LOCATION: (55)..(56)
<223> OTHER INFORMATION: Any naturally occurring amino acid
<220> FEATURE:
<221> NAME/KEY: VARIANT
<222> LOCATION: (68)..(68)
<223> OTHER INFORMATION: /replace="Ala"
<220> FEATURE:
<221> NAME/KEY: VARIANT
<222> LOCATION: (70)..(70)
<223> OTHER INFORMATION: /replace="Leu"
<220> FEATURE:
<221> NAME/KEY: VARIANT
<222> LOCATION: (72)..(72)
<223> OTHER INFORMATION: /replace="Val"
<220> FEATURE:
<221> NAME/KEY: VARIANT
<222> LOCATION: (74)..(74)
<223> OTHER INFORMATION: /replace="Lys"
<220> FEATURE:
<221> NAME/KEY: VARIANT
<222> LOCATION: (79)..(79)
<223> OTHER INFORMATION: /replace="Ala"
<220> FEATURE:
<221> NAME/KEY: misc_feature
<222> LOCATION: (1)..(121)
<223> OTHER INFORMATION: /note="Variant residues given in the sequence
      have no preference with respect to those in the annotations for
      variant positions"

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Asn Ile Asn Pro Ser Xaa Xaa Gly Thr Ser Phe Asn Glu Glu Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Leu Tyr Asp Gly Tyr Tyr Phe Asp Phe Trp Gly
            100                 105                 110

Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 1565 VL polypeptide"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
```

-continued

```
<222> LOCATION: (75)..(75)
<223> OTHER INFORMATION: /replace="Val"
<220> FEATURE:
<221> NAME/KEY: VARIANT
<222> LOCATION: (87)..(87)
<223> OTHER INFORMATION: /replace="Phe"
<220> FEATURE:
<221> NAME/KEY: misc_feature
<222> LOCATION: (1)..(107)
<223> OTHER INFORMATION: /note="Variant residues given in the sequence
      have no preference with respect to those in the annotations for
      variant positions"

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys
            100                 105

<210> SEQ ID NO 6
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 4384 VH polypeptide"
<220> FEATURE:
<221> NAME/KEY: VARIANT
<222> LOCATION: (38)..(38)
<223> OTHER INFORMATION: /replace="Lys"
<220> FEATURE:
<221> NAME/KEY: VARIANT
<222> LOCATION: (48)..(48)
<223> OTHER INFORMATION: /replace="Ile"
<220> FEATURE:
<221> NAME/KEY: VARIANT
<222> LOCATION: (55)..(55)
<223> OTHER INFORMATION: /replace="Ser"
<220> FEATURE:
<221> NAME/KEY: VARIANT
<222> LOCATION: (68)..(68)
<223> OTHER INFORMATION: /replace="Ala"
<220> FEATURE:
<221> NAME/KEY: VARIANT
<222> LOCATION: (70)..(70)
<223> OTHER INFORMATION: /replace="Leu"
<220> FEATURE:
<221> NAME/KEY: VARIANT
<222> LOCATION: (72)..(72)
<223> OTHER INFORMATION: /replace="Val"
<220> FEATURE:
<221> NAME/KEY: VARIANT
<222> LOCATION: (74)..(74)
<223> OTHER INFORMATION: /replace="Lys"
<220> FEATURE:
<221> NAME/KEY: VARIANT
<222> LOCATION: (79)..(79)
<223> OTHER INFORMATION: /replace="Ala"
<220> FEATURE:
<221> NAME/KEY: misc_feature
```

```
<222> LOCATION: (1)..(119)
<223> OTHER INFORMATION: /note="Variant residues given in the sequence
      have no preference with respect to those in the annotations for
      variant positions"

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Gln Ala Pro Gly Gln Gly Leu Glu Trp Met
            35                  40                  45

Gly Asn Ile Asn Pro Ser Asn Gly Gly Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Asp Phe Ser Trp Phe Val Tyr Trp Gly Gln Gly
            100                 105                 110

Thr Leu Val Thr Val Ser Ser
        115

<210> SEQ ID NO 7
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 4384 VL polypeptide"
<220> FEATURE:
<221> NAME/KEY: VARIANT
<222> LOCATION: (44)..(44)
<223> OTHER INFORMATION: /replace="Val"
<220> FEATURE:
<221> NAME/KEY: VARIANT
<222> LOCATION: (48)..(48)
<223> OTHER INFORMATION: /replace="Met"
<220> FEATURE:
<221> NAME/KEY: VARIANT
<222> LOCATION: (70)..(70)
<223> OTHER INFORMATION: /replace="Tyr"
<220> FEATURE:
<221> NAME/KEY: VARIANT
<222> LOCATION: (72)..(72)
<223> OTHER INFORMATION: /replace="Leu"
<220> FEATURE:
<221> NAME/KEY: VARIANT
<222> LOCATION: (86)..(86)
<223> OTHER INFORMATION: /replace="Phe"
<220> FEATURE:
<221> NAME/KEY: misc_feature
<222> LOCATION: (1)..(106)
<223> OTHER INFORMATION: /note="Variant residues given in the sequence
      have no preference with respect to those in the annotations for
      variant positions"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Ile Ser Arg Leu His Ser Gly Val Pro Ser Arg Phe Ser Gly Ser
```

```
                50                  55                  60
Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Gly Asn Thr Leu Pro Leu Thr
                 85                  90                  95

Phe Gly Gly Gly Thr Lys Val Glu Ile Lys
                100                 105
```

<210> SEQ ID NO 8
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 4517 VH polypeptide"
<220> FEATURE:
<221> NAME/KEY: VARIANT
<222> LOCATION: (39)..(39)
<223> OTHER INFORMATION: /replace="Leu"
<220> FEATURE:
<221> NAME/KEY: VARIANT
<222> LOCATION: (40)..(40)
<223> OTHER INFORMATION: /replace="Thr"
<220> FEATURE:
<221> NAME/KEY: VARIANT
<222> LOCATION: (44)..(44)
<223> OTHER INFORMATION: /replace="Arg"
<220> FEATURE:
<221> NAME/KEY: VARIANT
<222> LOCATION: (49)..(49)
<223> OTHER INFORMATION: /replace="Ala"
<220> FEATURE:
<221> NAME/KEY: VARIANT
<222> LOCATION: (74)..(74)
<223> OTHER INFORMATION: /replace="Ile"
<220> FEATURE:
<221> NAME/KEY: VARIANT
<222> LOCATION: (77)..(77)
<223> OTHER INFORMATION: /replace="Ser"
<220> FEATURE:
<221> NAME/KEY: misc_feature
<222> LOCATION: (1)..(121)
<223> OTHER INFORMATION: /note="Variant residues given in the sequence
      have no preference with respect to those in the annotations for
      variant positions"

<400> SEQUENCE: 8

```
Glu Val Gln Leu Val Glu Ser Gly Gly Gly Leu Val Lys Pro Gly Gly
 1                5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
         35                  40                  45

Ser Thr Ile Ser Gly Gly Gly Ser Tyr Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Lys Gly Asn Tyr Gly Asn Tyr Gly Lys Leu Ala Tyr Trp Gly
                100                 105                 110

Gln Gly Thr Thr Val Thr Val Ser Ser
        115                 120
```

<210> SEQ ID NO 9

```
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 4517 VL polypeptide"
<220> FEATURE:
<221> NAME/KEY: VARIANT
<222> LOCATION: (13)..(13)
<223> OTHER INFORMATION: /replace="Val"
<220> FEATURE:
<221> NAME/KEY: VARIANT
<222> LOCATION: (48)..(48)
<223> OTHER INFORMATION: /replace="Val"
<220> FEATURE:
<221> NAME/KEY: VARIANT
<222> LOCATION: (56)..(56)
<223> OTHER INFORMATION: /replace="Thr"
<220> FEATURE:
<221> NAME/KEY: VARIANT
<222> LOCATION: (71)..(71)
<223> OTHER INFORMATION: /replace="Tyr"
<220> FEATURE:
<221> NAME/KEY: VARIANT
<222> LOCATION: (84)..(84)
<223> OTHER INFORMATION: /replace="Gly"
<220> FEATURE:
<221> NAME/KEY: VARIANT
<222> LOCATION: (85)..(85)
<223> OTHER INFORMATION: /replace="Ser"
<220> FEATURE:
<221> NAME/KEY: VARIANT
<222> LOCATION: (104)..(104)
<223> OTHER INFORMATION: /replace="Leu"
<220> FEATURE:
<221> NAME/KEY: misc_feature
<222> LOCATION: (1)..(107)
<223> OTHER INFORMATION: /note="Variant residues given in the sequence
      have no preference with respect to those in the annotations for
      variant positions"

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Trp
                85                  90                  95

Thr Phe Gly Gln Gly Thr Lys Val Glu Ile Lys
            100                 105

<210> SEQ ID NO 10
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 5038 VH polypeptide"
<220> FEATURE:
<221> NAME/KEY: VARIANT
<222> LOCATION: (44)..(44)
<223> OTHER INFORMATION: /replace="Asn"
<220> FEATURE:
```

```
<221> NAME/KEY: VARIANT
<222> LOCATION: (49)..(49)
<223> OTHER INFORMATION: /replace="Met"
<220> FEATURE:
<221> NAME/KEY: VARIANT
<222> LOCATION: (55)..(55)
<223> OTHER INFORMATION: /replace="Ser"
<220> FEATURE:
<221> NAME/KEY: VARIANT
<222> LOCATION: (68)..(68)
<223> OTHER INFORMATION: /replace="Ile"
<220> FEATURE:
<221> NAME/KEY: VARIANT
<222> LOCATION: (72)..(72)
<223> OTHER INFORMATION: /replace="Arg"
<220> FEATURE:
<221> NAME/KEY: VARIANT
<222> LOCATION: (93)..(93)
<223> OTHER INFORMATION: /replace="Thr"
<220> FEATURE:
<221> NAME/KEY: misc_feature
<222> LOCATION: (1)..(120)
<223> OTHER INFORMATION: /note="Variant residues given in the sequence
      have no preference with respect to those in the annotations for
      variant positions"

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Phe Tyr Trp Thr Trp Ile Arg Gln His Pro Gly Lys Gly Leu Glu Trp
        35                  40                  45

Ile Gly Phe Ile Ser Tyr Asp Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Tyr Tyr Gly Asn Leu Phe Asp Tyr Trp Gly Gln
            100                 105                 110

Gly Thr Leu Val Thr Val Ser Ser
        115                 120

<210> SEQ ID NO 11
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 5038 VL polypeptide"
<220> FEATURE:
<221> NAME/KEY: VARIANT
<222> LOCATION: (36)..(36)
<223> OTHER INFORMATION: /replace="Phe"
<220> FEATURE:
<221> NAME/KEY: VARIANT
<222> LOCATION: (44)..(44)
<223> OTHER INFORMATION: /replace="Val"
<220> FEATURE:
<221> NAME/KEY: VARIANT
<222> LOCATION: (49)..(49)
<223> OTHER INFORMATION: /replace="Phe"
<220> FEATURE:
<221> NAME/KEY: VARIANT
<222> LOCATION: (71)..(71)
<223> OTHER INFORMATION: /replace="Tyr"
<220> FEATURE:
<221> NAME/KEY: VARIANT
```

```
<222> LOCATION: (73)..(73)
<223> OTHER INFORMATION: /replace="Leu"
<220> FEATURE:
<221> NAME/KEY: VARIANT
<222> LOCATION: (85)..(85)
<223> OTHER INFORMATION: /replace="Ile"
<220> FEATURE:
<221> NAME/KEY: VARIANT
<222> LOCATION: (87)..(87)
<223> OTHER INFORMATION: /replace="Phe"
<220> FEATURE:
<221> NAME/KEY: misc_feature
<222> LOCATION: (1)..(107)
<223> OTHER INFORMATION: /note="Variant residues given in the sequence
      have no preference with respect to those in the annotations for
      variant positions"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Val Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ile Thr Leu Pro Trp
                85                  90                  95

Thr Phe Gly Gln Gly Thr Lys Val Glu Ile Lys
            100                 105

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Humanized 5082 VH polypeptide"
<220> FEATURE:
<221> NAME/KEY: VARIANT
<222> LOCATION: (41)..(41)
<223> OTHER INFORMATION: /replace="Phe"
<220> FEATURE:
<221> NAME/KEY: VARIANT
<222> LOCATION: (46)..(46)
<223> OTHER INFORMATION: /replace="Val"
<220> FEATURE:
<221> NAME/KEY: VARIANT
<222> LOCATION: (49)..(49)
<223> OTHER INFORMATION: /replace="Met"
<220> FEATURE:
<221> NAME/KEY: VARIANT
<222> LOCATION: (55)..(55)
<223> OTHER INFORMATION: /replace="Ser"
<220> FEATURE:
<221> NAME/KEY: VARIANT
<222> LOCATION: (68)..(68)
<223> OTHER INFORMATION: /replace="Ile"
<220> FEATURE:
<221> NAME/KEY: VARIANT
<222> LOCATION: (72)..(72)
<223> OTHER INFORMATION: /replace="Arg"
<220> FEATURE:
<221> NAME/KEY: VARIANT
<222> LOCATION: (86)..(86)
<223> OTHER INFORMATION: /replace="Leu"
<220> FEATURE:
<221> NAME/KEY: misc_feature
```

<222> LOCATION: (1)..(118)
<223> OTHER INFORMATION: /note="Variant residues given in the sequence
have no preference with respect to those in the annotations for
variant positions"

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Ala
            20                  25                  30

Tyr Tyr Trp Asn Trp Ile Arg Gln His Pro Gly Lys Gly Leu Glu Trp
        35                  40                  45

Ile Gly Tyr Ile Gly Tyr Asp Gly Arg Asn Thr Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ser Arg Glu Gly Asp Tyr Gly Tyr Ser Asp Tyr Trp Gly Gln Gly Thr
            100                 105                 110

Leu Val Thr Val Ser Ser
        115

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic Humanized 5082 VL polypeptide"
<220> FEATURE:
<221> NAME/KEY: VARIANT
<222> LOCATION: (21)..(21)
<223> OTHER INFORMATION: /replace="Val"
<220> FEATURE:
<221> NAME/KEY: VARIANT
<222> LOCATION: (29)..(29)
<223> OTHER INFORMATION: /replace="Thr"
<220> FEATURE:
<221> NAME/KEY: VARIANT
<222> LOCATION: (44)..(44)
<223> OTHER INFORMATION: /replace="Val"
<220> FEATURE:
<221> NAME/KEY: VARIANT
<222> LOCATION: (69)..(69)
<223> OTHER INFORMATION: /replace="Ile"
<220> FEATURE:
<221> NAME/KEY: VARIANT
<222> LOCATION: (71)..(71)
<223> OTHER INFORMATION: /replace="Tyr"
<220> FEATURE:
<221> NAME/KEY: VARIANT
<222> LOCATION: (87)..(87)
<223> OTHER INFORMATION: /replace="Phe"
<220> FEATURE:
<221> NAME/KEY: VARIANT
<222> LOCATION: (104)..(104)
<223> OTHER INFORMATION: /replace="Leu"
<220> FEATURE:
<221> NAME/KEY: misc_feature
<222> LOCATION: (1)..(107)
<223> OTHER INFORMATION: /note="Variant residues given in the sequence
have no preference with respect to those in the annotations for
variant positions"

<400> SEQUENCE: 13

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Thr Leu Pro Trp
                85                  90                  95

Thr Phe Gly Gln Gly Thr Lys Val Glu Ile Lys
            100                 105

<210> SEQ ID NO 14
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
cgcgccgaag tgcagctggt ggagtctggg ggaggcttag tgaagcctgg agagtccttg      60
aaactctcct gtgcagcctc tggattcgct ttcagttact ctgacatgtc ttgggttcgc    120
cagactccgg agaagaggct ggagtgggtc gcatacatga gtagtgctgg tgatgtcacc    180
ttctattcag acactgtgaa gggccgattc accatctcca gagacaatgc caagaacacc    240
ctgtatctgc aagtgagcag tctgaagtct gaggacacag ccatatatta ctgtgtaaga    300
caccgggacg tggctatgga ctactggggt caaggaacct cagtcaccgt ctcg          354

<210> SEQ ID NO 15
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Arg Ala Glu Val Gln Leu Val Glu Ser Gly Gly Gly Leu Val Lys Pro
1               5                   10                  15

Gly Glu Ser Leu Lys Leu Ser Cys Ala Ala Ser Gly Phe Ala Phe Ser
            20                  25                  30

Tyr Ser Asp Met Ser Trp Val Arg Gln Thr Pro Glu Lys Arg Leu Glu
        35                  40                  45

Trp Val Ala Tyr Met Ser Ser Ala Gly Asp Val Thr Phe Tyr Ser Asp
    50                  55                  60

Thr Val Lys Gly Arg Phe Thr Ile Ser Arg Asp Asn Ala Lys Asn Thr
65                  70                  75                  80

Leu Tyr Leu Gln Val Ser Ser Leu Lys Ser Glu Asp Thr Ala Ile Tyr
                85                  90                  95

Tyr Cys Val Arg His Arg Asp Val Ala Met Asp Tyr Trp Gly Gln Gly
            100                 105                 110

Thr Ser Val Thr Val Ser
        115
```

<210> SEQ ID NO 16
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
ctagccgatg ttgtgatgac ccagactcca ctctccctgc ctgtcagtct tggagatcaa      60
gcctccatct cttgcagatc tagtcagagc cttgtacaca gtaatggaaa cacctattta     120
cattggtacc tgcagaagcc aggccagtct ccaaagctcc tgatctacaa agtttccaac     180
cgatttctg gggtcccaga caggttcagt ggcagtggat cagggacaga tttcacactc      240
aagatcagca gagtggaggc tgaggatctg ggagtttatt tctgctctca agtacacat      300
gttccgacgt tcggtggagg caccaagctg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc      600
gaagtcaccc atcagggcct gagctcgccc gtcacaaaga gcttcaacag gggagagtgt     660
```

<210> SEQ ID NO 17
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Leu Ala Asp Val Val Met Thr Gln Thr Pro Leu Ser Leu Pro Val Ser
 1               5                  10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Ile Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 18
<211> LENGTH: 370
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
ggcgcgccga ggtccaactg caacagtctg ggactgaatt ggtgaagcct ggggcttcag     60
tgatactgtc ctgtaaggcc tctggctaca ccttcaccag ctactggatg cagtgggtga    120
agcagaggcc tggacaaggc cttgagtgga ttggaaatat taatcctagc aatggtggaa    180
ctagtttcaa tgaggagttc aagagtaggg ccacactgac tgtagacaaa tcctccagta    240
cagcctacat gcaactcagc agcctgacat ctgaggactc tgcggtctat tattgtgcaa    300
gagacggggg cctttacgac ggatactact ttgacttctg gggccaaggc accactctca    360
cagtctcgag                                                           370

<210> SEQ ID NO 19
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Arg Ala Glu Val Gln Leu Gln Gln Ser Gly Thr Glu Leu Val Lys Pro
1               5                   10                  15

Gly Ala Ser Val Ile Leu Ser Cys Lys Ala Ser Gly Tyr Thr Phe Thr
            20                  25                  30

Ser Tyr Trp Met Gln Trp Val Lys Gln Arg Pro Gly Gln Gly Leu Glu
        35                  40                  45

Trp Ile Gly Asn Ile Asn Pro Ser Asn Gly Gly Thr Ser Phe Asn Glu
    50                  55                  60

Glu Phe Lys Ser Arg Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Asp Gly Gly Leu Tyr Asp Gly Tyr Tyr Phe Asp Phe
            100                 105                 110

Trp Gly Gln Gly Thr Thr Leu Thr Val Ser
        115                 120

<210> SEQ ID NO 20
<211> LENGTH: 663
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 20

```
gctagccaac attgtgatga cacagtctca caaattcatg tccacattaa taggagccag      60
ggtctccatc acctgcaagg ccagtcagga tgtggatacg gctgtagcct ggtatcaaca     120
gaaaccaggt caatctccta aattattaat ttattgggca tccacccggc acactggagt     180
ccctgatcgc ttcacaggca gtggatctgg gacagatttc tctctcaccg ttagcaatgt     240
gcagtctgag gacttaacag attatttctg tcagcaatat agcagctatc ctctcacgtt     300
cggtgctggg accaagctgg agctgaaacg aactgtggct gcaccatctg tcttcatctt     360
cccgccatct gatgagcagt tgaaatctgg aactgcctct gttgtgtgcc tgctgaataa     420
cttctatccc agagaggcca agtacagtg aaggtggat aacgccctcc aatcgggtaa      480
ctcccaggag agtgtcacag agcaggacag caaggacagc acctacagcc tcagcagcac     540
cctgacgctg agcaaagcag actacgagaa acacaaagtc tacgcctgcg aagtcaccca     600
tcagggcctg agctcgcccg tcacaaagag cttcaacagg ggagagtgtt aataagcggc     660
cgc                                                                   663
```

<210> SEQ ID NO 21
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Leu Ala Asn Ile Val Met Thr Gln Ser His Lys Phe Met Ser Thr Leu
1               5                   10                  15

Ile Gly Ala Arg Val Ser Ile Thr Cys Lys Ala Ser Gln Asp Val Asp
            20                  25                  30

Thr Ala Val Ala Trp Tyr Gln Gln Lys Pro Gly Gln Ser Pro Lys Leu
        35                  40                  45

Leu Ile Tyr Trp Ala Ser Thr Arg His Thr Gly Val Pro Asp Arg Phe
    50                  55                  60

Thr Gly Ser Gly Ser Gly Thr Asp Phe Ser Leu Thr Val Ser Asn Val
65                  70                  75                  80

Gln Ser Glu Asp Leu Thr Asp Tyr Phe Cys Gln Gln Tyr Ser Ser Tyr
                85                  90                  95

Pro Leu Thr Phe Gly Ala Gly Thr Lys Leu Glu Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205
```

Lys Ser Phe Asn Arg Gly Glu Cys
    210                 215

<210> SEQ ID NO 22
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
caggtgcagc tgcagcagcc tggcacagag ctggtgaaac ctggcgcctc cgtgaagctg      60
tcctgcaagg cctccggcta caccttcacc tcccactgga tgcactgggt gaaacagcgg     120
cctggacagg gcctggaatg gatcggcaac atcaaccct ccaacggcgg caccaactac      180
aacgagaagt tcaagtcccg ggccaccctg accgtggaca aggcctcctc caccgcctac    240
atgcagctgt cctccctgac ctccgaggac tccgccgtgt actactgcgc cagagcctac    300
tacgacttca gttggttcgt gtactggggc cagggcaccc tggtgacagt ctcg           354

<210> SEQ ID NO 23
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Arg Ala Thr Leu Thr Val Asp Lys Ala Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Tyr Asp Phe Ser Trp Phe Val Tyr Trp Gly Gln Gly
            100                 105                 110

Thr Leu Val Thr Val Ser
        115

<210> SEQ ID NO 24
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gatatccaga tgacccagac ctcctccagc ctgtccgcct ccctgggcga cagagtgacc      60
atctcctgcc ggtcctccca ggacatctcc aactacctga actggtatca gcagaaaccc    120

```
gacggcaccg tgaagctgct gatgtacatc tcccggctgc actccggcgt gccctccaga      180
ttctccggct ctggctccgg caccgagtac tccctgacca tcagcaacct ggaacaggaa      240
gatatcgcta cctacttctg tcagcagggc aacaccctgc ccctgacctt cggcgctggc      300
accaagctgg aactgaagcg gaccgtggcc gctccctccg tgttcatctt cccaccctcc      360
gacgagcagc tgaagtccgg caccgcctcc gtggtgtgcc tgctgaacaa cttctacccc      420
cgcgaggcca aggtgcagtg gaaggtggac aacgccctgc agtccggcaa ctcccaggaa      480
tccgtgaccg agcaggactc caaggacagc acctactccc tgtcctccac cctgaccctg      540
tccaaggccg actacgagaa gcacaaggtg tacgcctgcg aagtgaccca ccagggcctg      600
tccagccccg tgaccaagtc cttcaaccgg ggcgagtgc                             639
```

```
<210> SEQ ID NO 25
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25
```

Asp Ile Gln Met Thr Gln Thr Ser Ser Leu Ser Ala Ser Leu Gly
1               5                   10                  15

Asp Arg Val Thr Ile Ser Cys Arg Ser Ser Gln Asp Ile Ser Asn Tyr
            20                  25                  30

Leu Asn Trp Tyr Gln Gln Lys Pro Asp Gly Thr Val Lys Leu Leu Met
        35                  40                  45

Tyr Ile Ser Arg Leu His Ser Gly Val Pro Ser Arg Phe Ser Gly Ser
    50                  55                  60

Gly Ser Gly Thr Glu Tyr Ser Leu Thr Ile Ser Asn Leu Glu Gln Glu
65                  70                  75                  80

Asp Ile Ala Thr Tyr Phe Cys Gln Gln Gly Asn Thr Leu Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 26
<211> LENGTH: 360
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 26

```
gaagtgcagc tggtggaatc tggcggcgac ctggtgaaac ctggcggctc cctgaagctg      60
tcctgcgccg cctccggctt caccttctcc agctacggca tgtcctgggt gcgactgacc     120
cccgacaagc ggctggaatg ggtggcaacc atctccggcg aggctcctga cacctactac     180
cccgactccg tgaagggccg gttcaccatc tcccggata  tcgccaagtc caccctgtac     240
ctgcagatgt cctccctgaa gtccgaggac accgccgtgt actactgcgc ccggaagggc     300
aactacggca attacggcaa gctggcctac tggggccagg gcacctccgt gacagtctcg     360
```

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 27

```
Glu Val Gln Leu Val Glu Ser Gly Gly Asp Leu Val Lys Pro Gly Gly
1               5                  10                  15

Ser Leu Lys Leu Ser Cys Ala Ala Ser Gly Phe Thr Phe Ser Ser Tyr
            20                  25                  30

Gly Met Ser Trp Val Arg Leu Thr Pro Asp Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Ile Ala Lys Ser Thr Leu Tyr
65                  70                  75                  80

Leu Gln Met Ser Ser Leu Lys Ser Glu Asp Thr Ala Val Tyr Tyr Cys
                85                  90                  95

Ala Arg Lys Gly Asn Tyr Gly Asn Tyr Gly Lys Leu Ala Tyr Trp Gly
            100                 105                 110

Gln Gly Thr Ser Val Thr Val Ser
        115                 120
```

<210> SEQ ID NO 28
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 28

```
gatatccaga tgacccagtc ccccgcctcc ctgtccgtgt ctgtgggcga cagtgacc       60
atcacctgtc gggcctccga aacatctac  tccaacctgg cctggtatca gcaggaacag    120
ggcaagtccc cccagctgct ggtgtacgcc gccaccaatc tggccgacgg cgtgccctcc    180
agattctccg gctctggctc cggcacccag tactccctga gatcaactc  cctgcagtcc    240
gaggacttcg ctcctactac tgccagcac ttctgggca  cccctggac  cttcggcgga    300
ggcaccaagc tggaaatcaa gcggaccgtg gccgctccct ccgtgttcat cttcccaccc    360
tccgacgagc agctgaagtc cggcaccgcc tccgtggtgt gcctgctgaa caacttctac    420
```

```
ccccgcgagg ccaaggtgca gtggaaggtg gacaacgccc tgcagagcgg caactcccag      480
gaatccgtga ccgagcagga ctccaaggac agcacctact ccctgtcctc caccctgacc      540
ctgtccaagg ccgactacga gaagcacaag gtgtacgcct gcgaagtgac ccaccagggc      600
ctgtccagcc ccgtgaccaa gtccttcaac cggggcgagt gc                         642
```

<210> SEQ ID NO 29
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Glu Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 364
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
cgcgccgagg tgaagctggt tgagtcagga cctggcctcg tgaaaccttc tcagtctctg      60
tctctcacct gctctgtcac tggctactcc atcaccagtg gttttactg gacctggatc      120 cggcagtttc caggcaacaa attggaatgg atgggcttca taagctacga tggtagcaat      180
```

```
aactacaacc catctctcaa aaatcgaatc tccatcactc gtgacacatc taagaaccag      240
tttttcctga agttgaattc tgtgactact gaggacacag ccacatatta ctgtgcaaga      300
ggcggaggct actatggtaa cctctttgac tactggggcc aaggcaccac tctcacagtc      360
tcga                                                                   364
```

```
<210> SEQ ID NO 31
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31
```

Arg Ala Glu Val Lys Leu Val Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Gly Phe Tyr Trp Thr Trp Ile Arg Gln Phe Pro Gly Asn Lys Leu
        35                  40                  45

Glu Trp Met Gly Phe Ile Ser Tyr Asp Gly Ser Asn Asn Tyr Asn Pro
    50                  55                  60

Ser Leu Lys Asn Arg Ile Ser Ile Thr Arg Asp Thr Ser Lys Asn Gln
65                  70                  75                  80

Phe Phe Leu Lys Leu Asn Ser Val Thr Thr Glu Asp Thr Ala Thr Tyr
                85                  90                  95

Tyr Cys Ala Arg Gly Gly Tyr Tyr Gly Asn Leu Phe Asp Tyr Trp
            100                 105                 110

Gly Gln Gly Thr Thr Leu Thr Val Ser
        115                 120

```
<210> SEQ ID NO 32
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
ctagccgata ttgtgatgac tcaaactaca tcctccctgt ccgcctctct gggagacaga      60
gtcaccatca gttgcaggcc aagtcaggac attagcaatt atgtaaactg gtttcagcag     120
aaaccaggtg aactgttaa gctcctgatc ttccacacat caagattaca ctcaggagtc      180
ccatcaaggt tcagtggcag tgggtctgga acagattatt ctctcaccat tagcaccctg     240
gaacaggaag atattgccat ttacttttgc aacagggta ttcgcttcc gtggacgttc       300 ggtggcggca ccaagctgga aataaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata cgccctcca atcgggtaac      480 tcccaggaga gtgtcacaga gcaggacagc aaggacagca cctacagcct cagcagcacc     540
ctgacgctga gcaaagcaga ctacgagaaa cacaaagtct acgcctgcga agtcaccat      600 cagggcctga gctcgcccgt cacaaagagc ttcaacaggg gagagtgtta ataagcggcc     660
```

<210> SEQ ID NO 33
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Leu Ala Asp Ile Val Met Thr Gln Thr Thr Ser Ser Leu Ser Ala Ser
1               5                   10                  15

Leu Gly Asp Arg Val Thr Ile Ser Cys Arg Pro Ser Gln Asp Ile Ser
            20                  25                  30

Asn Tyr Val Asn Trp Phe Gln Gln Lys Pro Gly Gly Thr Val Lys Leu
        35                  40                  45

Leu Ile Phe His Thr Ser Arg Leu His Ser Gly Val Pro Ser Arg Phe
    50                  55                  60

Ser Gly Ser Gly Ser Gly Thr Asp Tyr Ser Leu Thr Ile Ser Thr Leu
65                  70                  75                  80

Glu Gln Glu Asp Ile Ala Ile Tyr Phe Cys Gln Gln Gly Ile Thr Leu
                85                  90                  95

Pro Trp Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 34
<211> LENGTH: 358
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
cgcgccgagg tgcagctgaa ggagtcagga cctggcctcg tgaaaccttc tcagtctctg      60
tctctcacct gctctgtcac cggctactcc atcaccagtg cttattactg gaactggatc     120
cggcagtttc caggaaacaa agtggaatgg atgggctaca taggctacga tggtcgtaat     180
acctacaacc catctctcaa aaatcgaatc tccatcactc gtgacacatc taagaaccag     240 ttttcctga aattgaattc tctgactact gaggacacag ccacatatta ttgttcaaga     300
gagggggact acggttactc tgactactgg ggccaaggca ccactctcac agtctcga     358

<210> SEQ ID NO 35
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Arg Ala Glu Val Gln Leu Lys Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Ala Tyr Tyr Trp Asn Trp Ile Arg Gln Phe Pro Gly Asn Lys Val
        35                  40                  45

Glu Trp Met Gly Tyr Ile Gly Tyr Asp Gly Arg Asn Thr Tyr Asn Pro
    50                  55                  60

Ser Leu Lys Asn Arg Ile Ser Ile Thr Arg Asp Thr Ser Lys Asn Gln
65                  70                  75                  80

Phe Phe Leu Lys Leu Asn Ser Leu Thr Thr Glu Asp Thr Ala Thr Tyr
                85                  90                  95

Tyr Cys Ser Arg Glu Gly Asp Tyr Gly Tyr Ser Asp Tyr Trp Gly Gln
            100                 105                 110

Gly Thr Thr Leu Thr Val Ser
        115
```

<210> SEQ ID NO 36
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

```
ctagccgata ttgtgatgac gcaagctaca tcctccctgt ctgcctctct gggagacaga     60
gtcaccgtca gttgcagggc aagtcaggac attaacaatt atttaaattg gtatcagcag    120
aagccagatg gaactgttaa actcctgatc tactacacat caagattaca gtcaggagtc    180
ccatcaaggt tcagtggcag tgggtctgga atagattatt ctctcaccat tagcaacctg    240
gagcaggaag attttgtcac ttactttttgc aacagagtg aaacgcttcc gtggacgttc     300
ggtggaggca ccaagctgga gctgaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcaccat    600 cagggcctga gctcgcccgt cacaaagagc ttcaacaggg gagagtgtta ataagcggcc    660
```

<210> SEQ ID NO 37
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

```
<400> SEQUENCE: 37

Leu Ala Asp Ile Val Met Thr Gln Ala Thr Ser Ser Leu Ser Ala Ser
1               5                   10                  15

Leu Gly Asp Arg Val Thr Val Ser Cys Arg Ala Ser Gln Asp Ile Asn
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Arg Leu Gln Ser Gly Val Pro Ser Arg Phe
    50                  55                  60

Ser Gly Ser Gly Ser Gly Ile Asp Tyr Ser Leu Thr Ile Ser Asn Leu
65                  70                  75                  80

Glu Gln Glu Asp Phe Val Thr Tyr Phe Cys Gln Gln Ser Glu Thr Leu
                85                  90                  95

Pro Trp Thr Phe Gly Gly Gly Thr Lys Leu Glu Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 38
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Tyr Ser
            20                  25                  30

Asp Met Ser Trp Val Arg Gln Ala Pro Gly Lys Arg Leu Glu Trp Val
        35                  40                  45

Ser Tyr Met Ser Ser Ala Gly Asp Val Thr Phe Tyr Ser Asp Thr Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Arg Ala Glu Asp Thr Ala Val Tyr Tyr Cys
                85                  90                  95

Val Arg His Arg Asp Val Ala Met Asp Tyr Trp Gly Gln Gly Thr Thr
            100                 105                 110

Val Thr Val Ser Ser
            115
```

<210> SEQ ID NO 39
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Gln Met Thr Gln Ser Pro Ser Ser Leu Ser Ala Ser Val Gly
1               5                   10                  15

Asp Arg Ala Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Ser
                85                  90                  95

Thr His Val Pro Thr Phe Gly Gly Gly Thr Lys Val Glu Ile Lys
            100                 105                 110

<210> SEQ ID NO 40
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Tyr Ser
            20                  25                  30

Asp Met Ser Trp Val Arg Gln Ala Pro Gly Lys Arg Leu Glu Trp Val
        35                  40                  45

Ser Tyr Met Ser Ser Ala Gly Asp Val Thr Phe Tyr Ser Asp Thr Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Arg Ala Glu Asp Thr Ala Val Tyr Tyr Cys
                85                  90                  95

Val Arg His Arg Asp Val Ala Ile Asp Tyr Trp Gly Gln Gly Thr Thr
            100                 105                 110

Val Thr Val Ser Ser
        115

<210> SEQ ID NO 41
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Thr Phe Gly Gly Gly Thr Lys Leu Glu Ile Lys
            100                 105                 110

<210> SEQ ID NO 42
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Tyr Ser
            20                  25                  30

Asp Met Ser Trp Val Arg Gln Ala Pro Gly Lys Arg Leu Glu Trp Val
        35                  40                  45

Ser Tyr Met Ser Ser Ala Gly Asp Val Thr Phe Tyr Ser Asp Thr Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Arg Ala Glu Asp Thr Ala Val Tyr Tyr Cys
                85                  90                  95

Val Arg His Arg Asp Val Ala Ile Asp Tyr Trp Gly Gln Gly Thr Thr
            100                 105                 110

Val Thr Val Ser Ser
        115

<210> SEQ ID NO 43
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Leu Asn Thr Tyr Leu His Trp Tyr Gln Gln Arg Pro Gly Gln Ser

```
                35                  40                  45
Pro Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Thr Phe Gly Gly Gly Thr Lys Val Glu Ile Lys
            100                 105                 110

<210> SEQ ID NO 44
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ser Tyr
                20                  25                  30

Trp Met Gln Trp Val Arg Gln Ala Pro Gly Gln Gly Leu Glu Trp Ile
             35                  40                  45

Gly Asn Ile Asn Pro Ser Asn Gly Gly Thr Ser Phe Asn Glu Glu Phe
 50                  55                  60

Lys Ser Arg Ala Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Gly Leu Tyr Asp Gly Tyr Tyr Phe Asp Phe Trp Gly
            100                 105                 110

Gln Gly Thr Leu Val Thr Val Ser Ser
        115                 120

<210> SEQ ID NO 45
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Ala Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
             35                  40                  45

Tyr Trp Ala Ser Thr Arg His Thr Gly Val Pro Ser Arg Phe Ser Gly
         50                  55                  60

Ser Gly Ser Gly Thr Asp Phe Thr Leu Thr Val Ser Ser Leu Gln Pro
 65                  70                  75                  80

Glu Asp Phe Ala Thr Tyr Phe Cys Gln Gln Tyr Ser Ser Tyr Pro Leu
                 85                  90                  95
```

```
Thr Phe Gly Gly Gly Thr Lys Val Glu Ile Lys
            100                 105
```

```
<210> SEQ ID NO 46
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46
```

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Ile
        35                  40                  45

Gly Asn Ile Asn Pro Ser Asn Leu Gly Thr Ser Phe Asn Glu Glu Phe
    50                  55                  60

Lys Ser Arg Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Leu Tyr Asp Gly Tyr Tyr Phe Asp Phe Trp Gly
            100                 105                 110

Gln Gly Thr Leu Val Thr Val Ser Ser
        115                 120
```

```
<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47
```

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Val Ser Ser Leu Gln Pro
65                  70                  75                  80

Glu Asp Phe Ala Thr Tyr Phe Cys Gln Gln Tyr Ser Ser Tyr Pro Leu
                85                  90                  95

Thr Phe Gly Gly Gly Thr Lys Val Glu Ile Lys
            100                 105
```

```
<210> SEQ ID NO 48
<211> LENGTH: 119
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Met
        35                  40                  45

Gly Asn Ile Asn Pro Ser Ser Gly Gly Thr Asn Tyr Asn Glu Lys Phe
    50                  55                  60

Lys Ser Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Asp Phe Ser Trp Phe Val Tyr Trp Gly Gln Gly
            100                 105                 110

Thr Leu Val Thr Val Ser Ser
        115

<210> SEQ ID NO 49
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asn Tyr
            20                  25                  30

Leu Asn Trp Tyr Gln Gln Lys Pro Gly Lys Ala Val Lys Leu Leu Met
        35                  40                  45

Tyr Ile Ser Arg Leu His Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Gly Asn Thr Leu Pro Leu Thr
                85                  90                  95

Phe Gly Gly Gly Thr Lys Val Glu Ile Lys
            100                 105

<210> SEQ ID NO 50
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
```

```
                     20                  25                  30

Trp Met His Trp Val Arg Gln Ala Pro Gly Gln Gly Leu Glu Trp Met
         35                  40                  45

Gly Asn Ile Asn Pro Ser Ser Gly Gly Thr Asn Tyr Asn Glu Lys Phe
 50                  55                  60

Lys Ser Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Ala Tyr Tyr Asp Phe Ser Trp Phe Val Tyr Trp Gly Gln Gly
            100                 105                 110

Thr Leu Val Thr Val Ser Ser
        115
```

<210> SEQ ID NO 51
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Asp Ile Ser Asn Tyr
             20                  25                  30

Leu Asn Trp Tyr Gln Gln Lys Pro Gly Lys Ala Pro Lys Leu Leu Met
         35                  40                  45

Tyr Ile Ser Arg Leu His Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Gly Asn Thr Leu Pro Leu Thr
             85                  90                  95

Phe Gly Gly Gly Thr Lys Val Glu Ile Lys
            100                 105
```

<210> SEQ ID NO 52
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Gly Met Ser Trp Val Arg Gln Ala Pro Gly Lys Gly Leu Glu Trp Val
         35                  40                  45

Ala Thr Ile Ser Gly Gly Gly Ser Tyr Thr Tyr Tyr Pro Asp Ser Val
 50                  55                  60

Lys Gly Arg Phe Thr Ile Ser Arg Asp Ile Ala Lys Ser Ser Leu Tyr
 65                  70                  75                  80
```

Leu Gln Met Asn Ser Leu Arg Ala Glu Asp Thr Ala Val Tyr Tyr Cys
                85                  90                  95

Ala Arg Lys Gly Asn Tyr Gly Asn Tyr Gly Lys Leu Ala Tyr Trp Gly
            100                 105                 110

Gln Gly Thr Thr Val Thr Val Ser Ser
        115                 120

<210> SEQ ID NO 53
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln His Phe Trp Gly Thr Pro Trp
                85                  90                  95

Thr Phe Gly Gln Gly Thr Lys Leu Glu Ile Lys
            100                 105

<210> SEQ ID NO 54
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Phe Tyr Trp Thr Trp Ile Arg Gln His Pro Gly Lys Gly Leu Glu Trp
        35                  40                  45

Met Gly Phe Ile Ser Tyr Ser Gly Ser Asn Asn Tyr Asn Pro Ser Leu
    50                  55                  60

Lys Asn Arg Ile Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Tyr Tyr Gly Asn Leu Phe Asp Tyr Trp Gly Gln
            100                 105                 110

Gly Thr Leu Val Thr Val Ser Ser
        115                 120

```
<210> SEQ ID NO 55
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Val Asn Trp Phe Gln Gln Lys Pro Gly Lys Ala Val Lys Leu Leu Ile
        35                  40                  45

Phe His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Ile Tyr Tyr Cys Gln Gln Gly Ile Thr Leu Pro Trp
                85                  90                  95

Thr Phe Gly Gln Gly Thr Lys Val Glu Ile Lys
            100                 105

<210> SEQ ID NO 56
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Phe Tyr Trp Thr Trp Ile Arg Gln His Pro Gly Asn Gly Leu Glu Trp
        35                  40                  45

Ile Gly Phe Ile Ser Tyr Ser Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Thr Tyr Tyr Cys
                85                  90                  95

Ala Arg Gly Gly Gly Tyr Tyr Gly Asn Leu Phe Asp Tyr Trp Gly Gln
            100                 105                 110

Gly Thr Leu Val Thr Val Ser Ser
            115                 120

<210> SEQ ID NO 57
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Val Asn Trp Phe Gln Gln Lys Pro Gly Lys Ala Pro Lys Leu Leu Ile
        35                  40                  45

Phe His Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Ile Thr Leu Pro Trp
                85                  90                  95

Thr Phe Gly Gln Gly Thr Lys Val Glu Ile Lys
            100                 105

<210> SEQ ID NO 58
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Ala
            20                  25                  30

Tyr Tyr Trp Asn Trp Ile Arg Gln His Pro Gly Lys Gly Val Glu Trp
        35                  40                  45

Met Gly Tyr Ile Gly Tyr Ser Gly Arg Asn Thr Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Glu Gly Asp Tyr Gly Tyr Ser Asp Tyr Trp Gly Gln Gly Thr
            100                 105                 110

Leu Val Thr Val Ser Ser
        115

<210> SEQ ID NO 59
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asp Thr Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Glu Thr Leu Pro Trp
                85                  90                  95

Thr Phe Gly Gln Gly Thr Lys Val Glu Ile Lys
            100                 105

<210> SEQ ID NO 60
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Ala
            20                  25                  30

Tyr Tyr Trp Asn Trp Ile Arg Gln Phe Pro Gly Lys Gly Val Glu Trp
        35                  40                  45

Met Gly Tyr Ile Gly Tyr Ser Gly Arg Asn Thr Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Glu Gly Asp Tyr Gly Tyr Ser Asp Tyr Trp Gly Gln Gly Thr
            100                 105                 110

Leu Val Thr Val Ser Ser
        115

<210> SEQ ID NO 61
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Asp Ile Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Glu Thr Leu Pro Trp
                85                  90                  95

Thr Phe Gly Gln Gly Thr Lys Leu Glu Ile Lys
            100                 105

<210> SEQ ID NO 62
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Val Gln Leu Val Glu Ser Gly Gly Leu Val Gln Pro Gly Gly
1               5                   10                  15

Ser Leu Arg Leu Ser Cys Ala Ala Ser Gly Phe Ala Phe Ser Tyr Ser
            20                  25                  30

Asp Met Ser Trp Val Arg Gln Ala Pro Gly Lys Gly Leu Glu Trp Val
        35                  40                  45

Ser Tyr Met Ser Ser Ala Gly Asp Val Thr Phe Tyr Ser Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg His Arg Asp Val Ala Met Asp Tyr Trp Gly Gln Gly Thr Thr
            100                 105                 110

Val Thr Val Ser Ser
        115

<210> SEQ ID NO 63
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Thr Phe Gly Gly Gly Thr Lys Val Glu Ile Lys
            100                 105                 110

<210> SEQ ID NO 64
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Val Glu Ile Lys
            100                 105                 110

<210> SEQ ID NO 65
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Asn Ile Asn Pro Ser Asn Gly Gly Thr Ser Phe Asn Glu Glu Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Leu Tyr Asp Gly Tyr Tyr Phe Asp Phe Trp Gly
            100                 105                 110

Gln Gly Thr Leu Val Thr Val Ser Ser
        115                 120

<210> SEQ ID NO 66
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

```
Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys
                100                 105

<210> SEQ ID NO 67
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Gln Ala Pro Gly Gln Gly Leu Glu Trp Met
            35                  40                  45

Gly Asn Ile Asn Pro Ser Asn Gly Gly Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Asp Phe Ser Trp Phe Val Tyr Trp Gly Gln Gly
                100                 105                 110

Thr Leu Val Thr Val Ser Ser
        115

<210> SEQ ID NO 68
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Ile Ser Arg Leu His Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80
```

Asp Ile Ala Thr Tyr Tyr Cys Gln Gln Gly Asn Thr Leu Pro Leu Thr
                85                  90                  95

Phe Gly Gly Gly Thr Lys Val Glu Ile Lys
            100                 105

<210> SEQ ID NO 69
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Lys Gly Asn Tyr Gly Asn Tyr Gly Lys Leu Ala Tyr Trp Gly
            100                 105                 110

Gln Gly Thr Thr Val Thr Val Ser Ser
        115                 120

<210> SEQ ID NO 70
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Trp
                85                  90                  95

Thr Phe Gly Gln Gly Thr Lys Val Glu Ile Lys
            100                 105

<210> SEQ ID NO 71
<211> LENGTH: 120
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Phe Tyr Trp Thr Trp Ile Arg Gln His Pro Gly Lys Gly Leu Glu Trp
        35                  40                  45

Ile Gly Phe Ile Ser Tyr Asp Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Tyr Tyr Gly Asn Leu Phe Asp Tyr Trp Gly Gln
            100                 105                 110

Gly Thr Leu Val Thr Val Ser Ser
        115                 120

<210> SEQ ID NO 72
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Val Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Ile Thr Leu Pro Trp
                85                  90                  95

Thr Phe Gly Gln Gly Thr Lys Val Glu Ile Lys
            100                 105

<210> SEQ ID NO 73
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Tyr Ser Ile Thr Ser Ala
            20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Arg Asn Thr Tyr Asn Pro Ser Leu
 50                  55                  60

Lys Asn Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ser Arg Glu Gly Asp Tyr Gly Tyr Ser Asp Tyr Trp Gly Gln Gly Thr
                100                 105                 110

Leu Val Thr Val Ser Ser
            115

<210> SEQ ID NO 74
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Glu Thr Leu Pro Trp
                 85                  90                  95

Thr Phe Gly Gln Gly Thr Lys Val Glu Ile Lys
                100                 105
```

What is claimed is:

1. A method for treating cancer in a human patient, the method comprising administering to said patient an effective amount of an antibody composition comprising:
   a) an anti-epidermal growth factor receptor (EGFR) antibody comprising a heavy chain and a light chain that comprise the amino acid sequences of:
      SEQ ID NOs: 42 and 43, respectively,
      SEQ ID NOs: 38 and 39, respectively,
      SEQ ID NOs: 40 and 41, respectively,
      SEQ ID NOs: 44 and 45, respectively, or
      SEQ ID NOs: 46 and 47, respectively;
   b) an anti-human epidermal growth factor receptor 2 (HER2) antibody comprising a heavy chain and a light chain that comprise the amino acid sequences of:
      SEQ ID NOs: 50 and 51, respectively,
      SEQ ID NOs: 48 and 49, respectively, or
      SEQ ID NOs: 52 and 53, respectively; and
   c) an anti-human epidermal growth factor receptor 3 (HER3) antibody comprising a heavy chain and a light chain that comprise the amino acid sequences of:
      SEQ ID NOs: 54 and 55, respectively,
      SEQ ID NOs: 56 and 57, respectively,
      SEQ ID NOs: 58 and 59, respectively, or
      SEQ ID NOs: 60 and 61, respectively.

2. The method of claim 1, wherein said antibody composition comprises:
   a) an anti-epidermal growth factor receptor (EGFR) antibody comprising a heavy chain and a light chain that comprise the amino acid sequences of:
      SEQ ID NOs: 38 and 39, respectively,
      SEQ ID NOs: 40 and 41, respectively, or
      SEQ ID NOs: 42 and 43, respectively;
   b) an anti-EGFR antibody comprising a heavy chain and a light chain that comprise the amino acid sequences of:
      SEQ ID NOs: 44 and 45, respectively, or
      SEQ ID NOs: 46 and 47, respectively;

c) an anti-human epidermal growth factor receptor 2 (HER2) antibody comprising a heavy chain and a light chain that comprise the amino acid sequences of:
SEQ ID NOs: 48 and 49, respectively, or
SEQ ID NOs: 50 and 51, respectively;
d) an anti-HER2 antibody comprising a heavy chain that comprises the amino acid sequence of SEQ ID NO: 52 and a light chain that comprises the amino acid sequence of SEQ ID NO: 53;
e) an anti-human epidermal growth factor receptor 3 (HER3) antibody comprising a heavy chain and a light chain that comprise the amino acid sequences of:
SEQ ID NOs: 54 and 55, respectively, or
SEQ ID NOs: 56 and 57, respectively; and
f) an anti-HER3 antibody comprising a heavy chain and a light chain that comprise the amino acid sequences of:
SEQ ID NOs: 58 and 59, respectively, or
SEQ ID NOs: 60 and 61, respectively.

3. The method of claim 1, wherein said antibody composition has at least one of the following properties:
a) inhibits cancer growth in the patient;
b) reduces EGFR, HER2, or HER3 expression in cancer cells in the patient; and
c) prevents EGFR, HER2, or HER3 up-regulation in cancer cells in the patient.

4. The method of claim 1, wherein the patient has pancreatic cancer, lung cancer, head and neck cancer, breast cancer, gastric cancer, colorectal cancer, esophageal cancer, or ovarian cancer.

5. The method of claim 1, wherein the patient has pancreatic cancer and a KRAS mutation.

6. The method of claim 1, wherein at least one of the antibodies is conjugated to an anti-cancer agent.

7. The method of claim 1, wherein the patient has been treated for cancer previously.

8. The method of claim 1, wherein said patient has acquired resistance to treatment with an antibody and/or a tyrosine kinase inhibitor.

9. The method of claim 8, wherein the antibody is cetuximab, trastuzumab, or pertuzumab.

10. A method for treating cancer in a human patient, the method comprising administering to said patient an effective amount of an antibody composition comprising:
a) an anti-epidermal growth factor receptor (EGFR) antibody comprising the heavy chain variable region (VH) amino acid sequence of SEQ ID NO: 42 and the light chain variable region (VL) amino acid sequence of SEQ ID NO: 43;
b) an anti-EGFR antibody comprising the VH amino acid sequence of SEQ ID NO: 46 and the VL amino acid sequence of SEQ ID NO: 47;
c) an anti-human epidermal growth factor receptor 2 (HER2) antibody comprising the VH amino acid sequence of SEQ ID NO: 50 and the VL amino acid sequence of SEQ ID NO: 51;
d) an anti-HER2 antibody comprising the VH amino acid sequence of SEQ ID NO: 52 and the VL amino acid sequence of SEQ ID NO: 53;
e) an anti-human epidermal growth factor receptor 3 (HER3) antibody comprising the VH amino acid sequence of SEQ ID NO: 54 and the VL amino acid sequence of SEQ ID NO: 55; and
f) an anti-HER3 antibody comprising the VH amino acid sequence of SEQ ID NO: 60 and the VL amino acid sequence of SEQ ID NO: 61.

11. The method of claim 10, wherein said antibody composition has at least one of the following properties:
a) inhibits cancer growth in the patient;
b) reduces EGFR, HER2, or HER3 expression in cancer cells in the patient; and
c) prevents EGFR, HER2, or HER3 up-regulation in cancer cells in the patient.

12. The method of claim 10, wherein the patient has pancreatic cancer, lung cancer, head and neck cancer, breast cancer, gastric cancer, colorectal cancer, esophageal cancer, or ovarian cancer.

13. The method of claim 10, wherein the patient has pancreatic cancer and a KRAS mutation.

14. The method of claim 10, wherein at least one of the antibodies is conjugated to an anti-cancer agent.

15. The method of claim 10, wherein the patient has been treated for cancer previously.

16. The method of claim 10, wherein said patient has acquired resistance to treatment with an antibody and/or a tyrosine kinase inhibitor.

17. The method of claim 16, wherein the antibody is cetuximab, trastuzumab, or pertuzumab.

18. A method for treating a human patient with a disorder characterized by overexpression of EGFR, HER2, and/or HER3, the method comprising administering to said patient an effective amount of an antibody composition comprising:
a) an anti-epidermal growth factor receptor (EGFR) antibody comprising a heavy chain and a light chain that comprise the amino acid sequences of:
SEQ ID NOs: 42 and 43, respectively,
SEQ ID NOs: 38 and 39, respectively,
SEQ ID NOs: 40 and 41, respectively,
SEQ ID NOs: 44 and 45, respectively, or
SEQ ID NOs: 46 and 47, respectively;
b) an anti-human epidermal growth factor receptor 2 (HER2) antibody comprising a heavy chain and a light chain that comprise the amino acid sequences of:
SEQ ID NOs: 50 and 51, respectively,
SEQ ID NOs: 48 and 49, respectively, or
SEQ ID NOs: 52 and 53, respectively; and
c) an anti-human epidermal growth factor receptor 3 (HER3) antibody comprising a heavy chain and a light chain that comprise the amino acid sequences of:
SEQ ID NOs: 54 and 55, respectively,
SEQ ID NOs: 56 and 57, respectively,
SEQ ID NOs: 58 and 59, respectively, or
SEQ ID NOs: 60 and 61, respectively.

19. The method of claim 18, wherein said antibody composition comprises:
a) an anti-epidermal growth factor receptor (EGFR) antibody comprising the heavy chain variable region (VH) amino acid sequence of SEQ ID NO: 42 and the light chain variable region (VL) amino acid sequence of SEQ ID NO: 43;
b) an anti-EGFR antibody comprising the VH amino acid sequence of SEQ ID NO: 46 and the VL amino acid sequence of SEQ ID NO: 47;
c) an anti-human epidermal growth factor receptor 2 (HER2) antibody comprising the VH amino acid sequence of SEQ ID NO: 50 and the VL amino acid sequence of SEQ ID NO: 51;
d) an anti-HER2 antibody comprising the VH amino acid sequence of SEQ ID NO: 52 and the VL amino acid sequence of SEQ ID NO: 53;
e) an anti-human epidermal growth factor receptor 3 (HER3) antibody comprising the VH amino acid sequence of SEQ ID NO: 54 and the VL amino acid sequence of SEQ ID NO: 55; and f) an anti-HER3 antibody comprising the VH amino acid sequence of SEQ ID NO: 60 and the VL amino acid sequence of SEQ ID NO: 61.

20. The method of claim 18, wherein said antibody composition has at least one of the following properties:
   a) reduces EGFR, HER2, or HER3 expression in cancer cells in the patient; and
   b) prevents EGFR, HER2, or HER3 up-regulation in cancer cells in the patient.

* * * * *